(12) United States Patent
Xie et al.

(10) Patent No.: US 11,674,128 B2
(45) Date of Patent: Jun. 13, 2023

(54) ENGINEERING OF A MINIMAL SACAS9 CRISPR/CAS SYSTEM FOR GENE EDITING AND TRANSCRIPTIONAL REGULATION OPTIMIZED BY ENHANCED GUIDE RNA

(71) Applicant: Tsinghua University, Beijing (CN)

(72) Inventors: Zhen Xie, Beijing (CN); Dacheng Ma, Beijing (CN)

( * ) Notice: Subject to any disclaimer, the term of this patent is extended or adjusted under 35 U.S.C. 154(b) by 0 days.

(21) Appl. No.: 15/619,518

(22) Filed: Jun. 11, 2017

(65) Prior Publication Data

US 2018/0163188 A1    Jun. 14, 2018

Related U.S. Application Data

(63) Continuation-in-part of application No. 15/376,569, filed on Dec. 12, 2016.

(30) Foreign Application Priority Data

May 19, 2017  (WO) ................ PCT/CN2017/085202

(51) Int. Cl.
  *C12N 9/22*     (2006.01)
  *C12N 15/86*    (2006.01)
  *C12N 15/11*    (2006.01)

(52) U.S. Cl.
  CPC ............... *C12N 9/22* (2013.01); *C12N 15/86* (2013.01); *C12Y 301/21004* (2013.01); *C07K 2319/70* (2013.01); *C12N 15/111* (2013.01); *C12N 2310/20* (2017.05); *C12N 2310/344* (2013.01); *C12N 2310/3519* (2013.01); *C12N 2750/14143* (2013.01)

(58) Field of Classification Search
  None
  See application file for complete search history.

(56) References Cited

U.S. PATENT DOCUMENTS 8,865,406 B2 * 10/2014 Zhang .................... C12N 15/63
                                                    435/6.1
10,392,607 B2 * 8/2019 Sternberg ............... C12N 15/90

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Uniprot Accession No. J7RUAS, Sep. 18, 2019.*
Pdb Accession No. 5AXW_A, Sep. 2, 2015.*
Ma, Rational Design of Mini-Cas9 for Transcriptional Activation, ACS Synth. Biol. 2018, 7, 978-985 Mar. 21, 2018.
Ma, Integration and exchange of split dCas9 domains for transcriptional controls in mammalian cells, Nature Communications, DOI: 10.1038/ncomms13056 Oct. 3, 2016.

* cited by examiner

*Primary Examiner* — Richard G Hutson
(74) *Attorney, Agent, or Firm* — Bioinnovation Legal PLLC; James C. Schroeder

(57) ABSTRACT

The presently claimed invention offers programmable and precise regulation of Cas9 functions by utilizing a set of compact Cas9 derivatives created by deleting conserved HNH and/or REC-C domains based on the structural information across variant class 2 CRISPR effectors. In addition, a novel strategy for engineering the dimeric gRNA-guided nuclease by splitting the mini-dSaCas9 and fusing the FokI domain right after the split point is claimed to increase the on-target DNA cleavage efficiency and potentially reduce the off-target effect because of a closer proximity of dimeric FokI nuclease to the target sequence. By combining the optimized and compact gRNA expression cassette and the downsized SaCas9 derivatives, the entire CRISPR/Cas system with different effector domains for transactivation, DNA cleavage and base editing is loaded into a single AAV virus. Such an all-in-one AAV-CRISPR/Cas9 system will be particularly appealing in biomedical applications that require safe and efficient delivery in vivo.

2 Claims, 8 Drawing Sheets

Specification includes a Sequence Listing.

101

201                                              203

301                                              303

ENGINEERING OF A MINIMAL SACAS9 CRISPR/CAS SYSTEM FOR GENE EDITING AND TRANSCRIPTIONAL REGULATION OPTIMIZED BY ENHANCED GUIDE RNA

Related applications: This application is a continuation in part of and claims priority to U.S. application Ser. No. 15/376,569 filed Dec. 12, 2016 and PCT patent application PCT/CN2017/085202 filed in China on May 19, 2017.

TECHNICAL FIELD

The instant application is related to the biological arts, in particular the directed modification of genetic material. With greater particularity, the claimed invention is related to improvements upon the Cas9 CRISPR-associated protein and related products thereof.

BACKGROUND ART

The CRISPR-associated protein 9 (Cas9) discovered from *Streptococcus pyogenes* is a multi-domain protein, which has been widely used in genome editing and transcriptional control in mammalian cells due to its superior modularity and versatility. Delivering synthetic gene circuits in vivo has been limited due to size constraints particularly with smaller delivery systems with a payload capacity nearly equal to an entire Cas9 complex.

SUMMARY OF INVENTION

Technical Problem

Several strategies have been developed to engineer modular and layered gene circuits in mammalian cells by regulating dCas9 and gRNA expression. Transcriptional controls in mammalian cells can be achieved by directly fusing a transcriptional regulatory domain to the nuclease deactivated Cas9 (dCas9). Alternatively, multiple transcriptional regulatory domains can be recruited to the dCas9 by tagging the dCas9 with a repeating peptide scaffold, or by fusing repeating RNA motifs to the cognate gRNA. However, biomedical applications of the CRISPR/Cas system require the exploration of new platforms for engineering mammalian synthetic circuits that integrate and process multiple endogenous inputs. In addition, the application of CRISPR/Cas therapeutic circuits is also challenging due to the restrictive cargo size of existing viral delivery vehicles.

Solution to Problem

The split Cas9 system can be used in general to bypass the packing limit of the viral delivery vehicles and in the claimed invention dCas9 is split and reconstituted in human cells. One of the challenges of therapeutic applications is to find an optimal delivery system that can carry all CRISPR/Cas9 components to the desired organ or cell population for genetic manipulation. Using the CRISPR/Cas system to greatest potential has been greatly limited by its physical size when incorporated into a viral delivery system. When used for synthetic biology purposes in high value delivery systems with site specific integration such as the Adeno-Associated Virus/AAV, the entire cas9 complex is akin to a computer operating system taking up 95% of available memory leaving only a small portion for synthetic biology programming purposes. By splitting the CRISPR/CAS9 into smaller regions and delivering the regions in separate viral delivery vectors, the powerful genetic manipulation functionality is retained alongside substantial increases in space for cellular programming purposes. The claimed invention represents a substantial improvement over existing CAS9 delivery techniques and includes additional enhancements for genetic control and programming.

While a variety of viral delivery systems have been employed with mixed success, implementation of systems relying on alternate virus systems can lead to an undesired strong immune response. Using the recombinant adeno-associated virus (rAAV) offers high gene transfer efficiency and very low immune response. Unfortunately packaging capacity is confined to 4.7 kb to 5 kb which is problematic when compared with human optimized Cas9 size at over 4.2 kb with promoter sequences reaching over 5 kb. With intein-mediated split Cas9, inteins function as protein introns and are excised out of a sequence and join the remaining flaking regions (exteins) with a peptide bond without leaving a scar. In terms of split site selection particular attention is given to split sites which are surface exposed due to the sterical need for protein splicing. This system allows the coding sequence of Cas9 to be distributed on a dual-vector or multi-vector system and reconstituted post-translationally.

The claimed invention expands the reach of synthetic biology by targeting specific diagnostic and therapeutic applications through improvements in genetic circuitry and higher level genetic circuit delivery enhancements. The claimed embodiments of the invention overcome existing size limitations through optimal splitting of Cas9 allowing for higher level synthetic gene circuitry to be accommodated by smaller delivery systems.

The presently claimed invention utilizes downsized *Staphylococcus aureus* Cas9 variants (mini-SaCas9) which retain DNA binding activity by deleting conserved functional domains. In a preferred illustrative embodiment, FokI nuclease domain is fused to the middle of the split mini-SaCas9 to trigger efficient DNA cleavage. In another illustrative embodiment the genetic editing system is small enough to be housed within a single AAV containing the mini-SaCas9 fused with a downsized transactivation domain along with an optimized and compact gRNA expression cassette with an efficient transactivation activity. The claimed invention highlights a practical approach to generate an all in one AAV-CRISPR/Cas9 system with different effector domains for in-vivo applications.

To bypass the AAV payload limit, the 4.2-kb Cas9 from *Streptococcus pyogenes* (SpCas9) is split and packaged into two separate AAVs along with the guide RNA (gRNA) expression unit, which allows functional reconstitution of full-length SpCas9 in vivo. Another strategy is to search for natural class 2 CRISPR effectors with a diminished size, such as the 3.2-kb SaCas9 and ~3-kb CasX identified in uncultivated organisms by using metagenomic datasets. To further reduced the transgene size, the ~70-bp glutamine tRNA can be used to replace the ~250-bp RNA polymerase III promoter to drive expression of the tRNA:gRNA fusion transcript that is cleaved by endogenous tRNase Z to produce the active gRNA. These efforts facilitate the construction of an all-in-one AAV delivery vector for in vivo applications of the CRISPR/Cas technology.

Recent structural studies of SpCas9, SaCas9 and Acidaminococcus sp. Cpf1 (AsCpf1) have elucidated functions of conserved domains among these class 2 CRISPR effectors, including C and RuvC nuclease domains that respectively cleave complementary and non-complementary DNA strands, a recognition (REC) domain, and a protospacer adjacent motif (PAM) interacting (PI) domain. Interestingly, truncated SpCas9 mutant by deleting either the HNH or the REC2 domain retain nearly intact DNA binding activity or half of cleavage activity. These results highlight the possibility to further downsize the wild-type Cas9 to a minimal Cas9 (mini-Cas9) that has only DNA binding activity but no DNA cleavage activity, which allows accommodating additional DNA template, effector domains and control elements in a single AAV vector.

Advantageous Effects of Invention

Such a CRISPR/Cas9 system has particular utility in biomedical applications in which viral delivery vehicles with a restrictive cargo size are preferred. Foreseen variants include combination of the split Cas9/dCas9 system with rAAV delivery systems, Cas9/dCas9 activity can be controlled to edit and regulate endogenous genes in vivo.

BRIEF DESCRIPTION OF DRAWINGS

The accompanying drawings are included to better illustrate exemplary embodiments of the claimed invention.

DESCRIPTION OF EMBODIMENTS

In the following embodiments as detailed further in the corresponding figures, rational design of the compact CRISPR/Cas9 system is further detailed.

Figure 1:
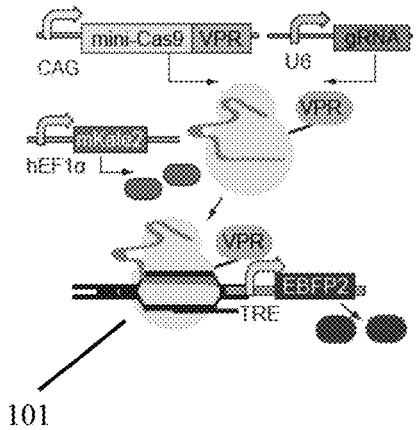
FIG. 1 is a diagram of EBFP2 transcription activation assay for the compact Cas9 derivatives fused with the VPR domain.

FIG. 1 is a diagram of EBFP2 transcription activation assay for the compact Cas9 derivatives (101) fused with the VPR domain. The constitutively expressed mKate2 is used as a transfection control. In the first illustrative example, the reporting system is utilized in cultured human embryonic kidney 293 (HEK293) cells. Two mini-dSpCas9 are created by respectively deleting the Cterminal region of REC1 domain (REC-C, Δ501-710) and the HNH domain (Δ777-891) that may be dispensable for DNA binding activity of the nuclease deactivated Cas9 (dCas9) and respectively fused to the VP64-p65-Rta (VPR) transactivation domain.

Figure 2:
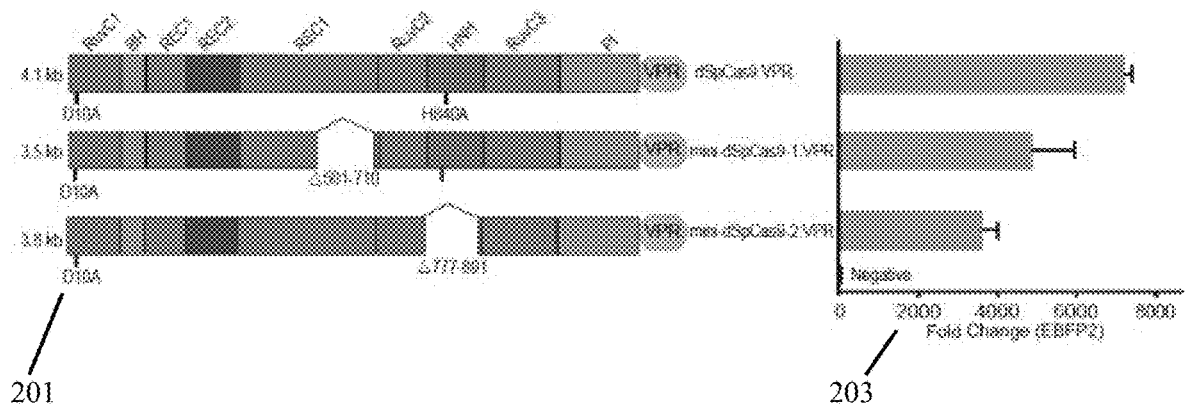
FIG. 2 is a diagram of dSpCas9, mini-dSpCas9-1 and mini-dSpCas9-2 domain organization and corresponding gene activation efficiency.

FIG. 2 is a diagram of dSpCas9, mini-dSpCas9-1 and mini-dSpCas9-2 domain organization (201) and graphical illustration of corresponding gene activation efficiency (203). In the illustrative example, the two mini-dSpCas9:VPR variants retain more than 50% of transactivation capacity compared to the dSpCas9:VPR.

Figure 3:
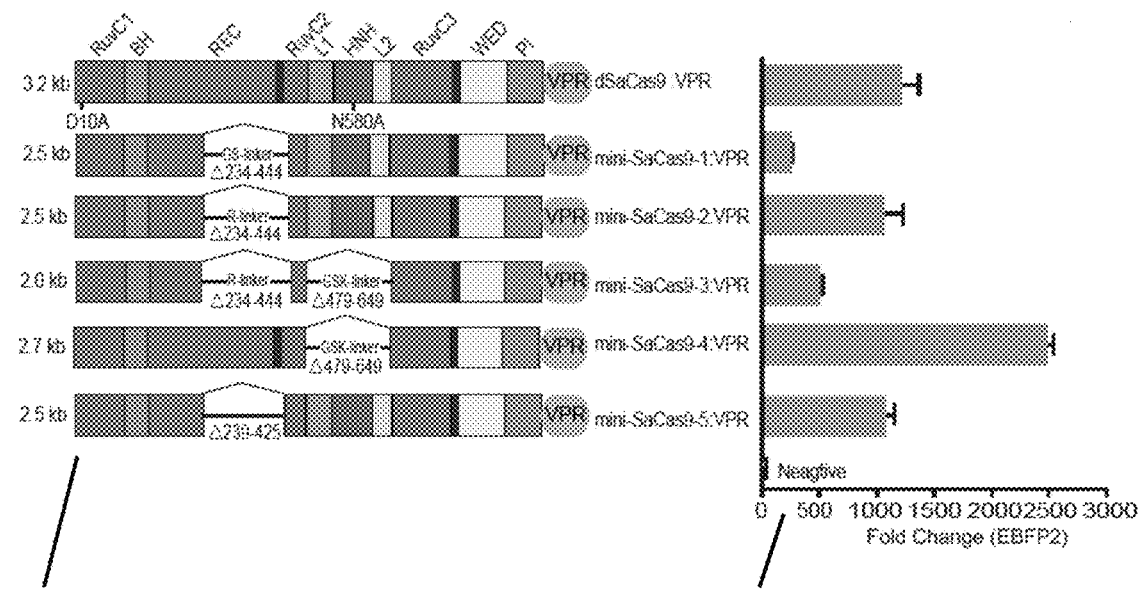
FIG. 3 is a schematic diagram of domain organization of dSaCas9 and its derivatives and results gene activation efficiency.

FIG. 3 is a schematic diagram of domain organization of dSaCas9 and its derivatives (301) and graphical illustration (303) depicting gene activation efficiency. Recently, the wildtype SaCas9 has been engineered to recognize an altered PAM ("NNNRRT") Seq ID NO: 35. Based on this mutant SaCas9, the disclosed embodiment constructs the mini-SaCas9-1:VPR by replacing the conserved REC-C domain (Δ234-444) with a "GGGGSGGGG" linker (GS-linker) Seq ID NO: 36, which only retained ~2.5% transactivation activity of the dSaCas9:VPR. Although the GS-linker is widely used as a flexible linker, it may still distort the SaCas9 structure. Inspired by a recent computational protocol called SEWING, an adjacent residue searching (ARS) protocol is used to search for existing structures between discontinued Cas9 fragments. Replacement of the GS-linker with a "KRRRRHR" (R-linker) SEQ ID NO: 37 from the SaCas9 BH domain that appropriately filled in the REC-C deletion gap by using the ARS protocol, results in a 11-fold increase in the transactivation capacity of mini-SaCas9-2. As an enhanced embodiment of the claimed invention, a "GSK" linker SEQ ID NO: 38 is used, derived from a putative gene (Accession number, O67859) in Aquifex aeolicus by using the SAR protocol, which fit the deletion gap of the HNH domain (Δ479-649). The 2-kb mini-SaCas9-3 is created by deleting both the REC-C domain and the HNH domain only retained 0.6% transactivation activity over the control.

Figure 4:
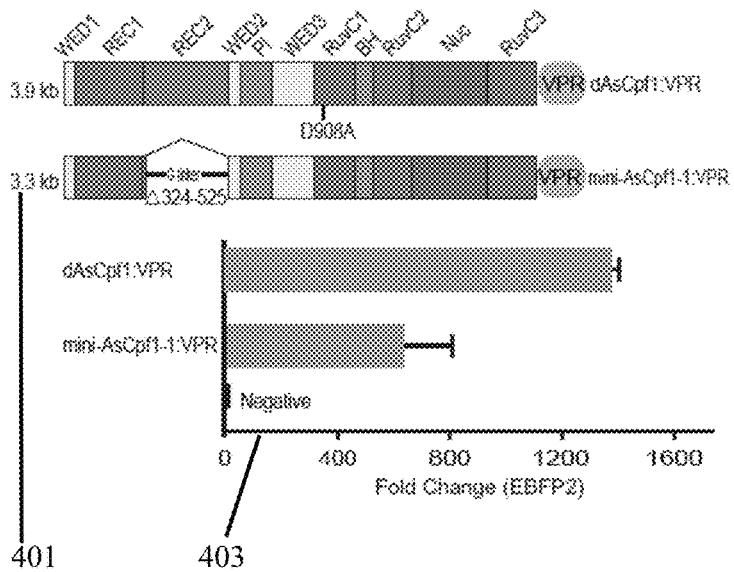
FIG. 4 is a diagram of dAsCpf1 and mini-AsCpf1-1 domain organization and corresponding gene activation efficiency.

FIG. 4 is a diagram of dAsCpf1 and mini-AsCpf1-1 domain organization (401) and graphical illustration (403) of corresponding gene activation efficiency. To evaluate the DNA cleavage efficiency of mini-SaCas9 variants in this illustrative embodiment, a reporter reconstitution assay is used where DNA cleavage can trigger the reconstitution of the active enhanced yellow fluorescent protein (EYFP) reporter gene from the inactive form. Either deleting the REC-C or deleting both the REC-C and HNH domains resulted in a background EYFP expression, suggesting that the domain deletion abolished the DNA cleavage activity of mini-SaCas9 variants. In this illustrative embodiment, by deleting REC2 domain (Δ324-525) retained 46% transactivation capacity of dAsCpf1:VPR, suggesting that this deletion strategy is applicable for distinct class 2 CRISPR effectors.

Figure 5:
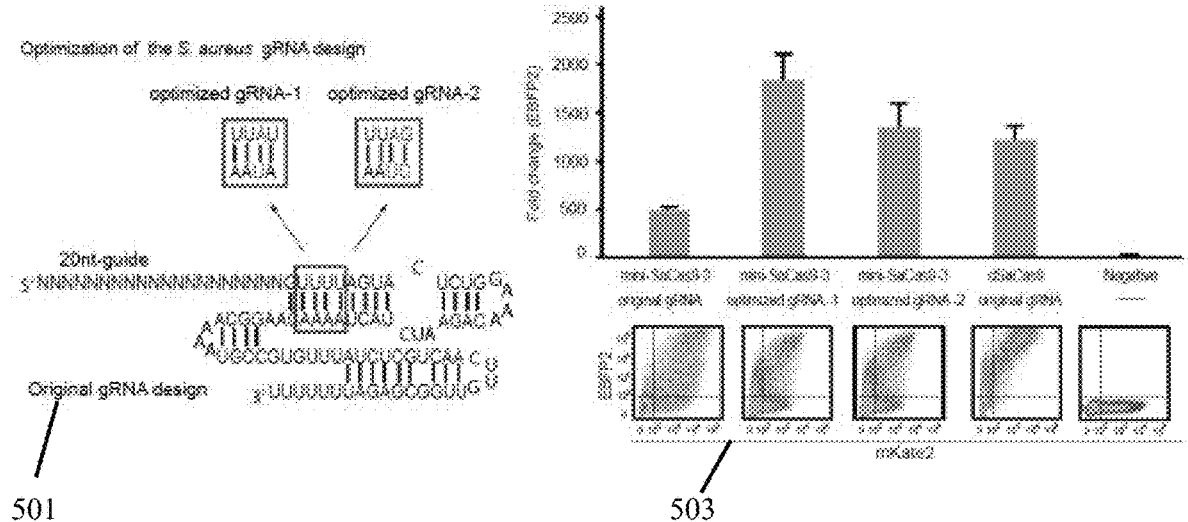
FIG. 5 is a schematic representation of optimized gRNAs and the corresponding gene activation efficiency.

FIG. 5 is a schematic representation of optimized gRNAs (501) and the corresponding graphical illustration (503) of gene activation efficiency. An A-U flip or a U-G conversion can be introduced to disrupt the putative RNA Pol III terminator sequences in the first stem loop of the gRNA scaffold to enhance the efficiency of the dCas9-mediated DNA labeling. The putative RNA Pol III terminator sequences are shown in the box, and the A-U and G-C mutations are labeled in shading at the third and fourth positions. Representative scatter plots of the flow cytometry data are also shown on the right. The constitutively expressed mKate2 is used as a transfection control. In a preferred illustrative embodiment, the transactivation efficiency of miniSaCas9-3 is increased ~100-fold by introducing either one or two point mutations in the putative RNA Pol III terminator sequences.

Figure 6:
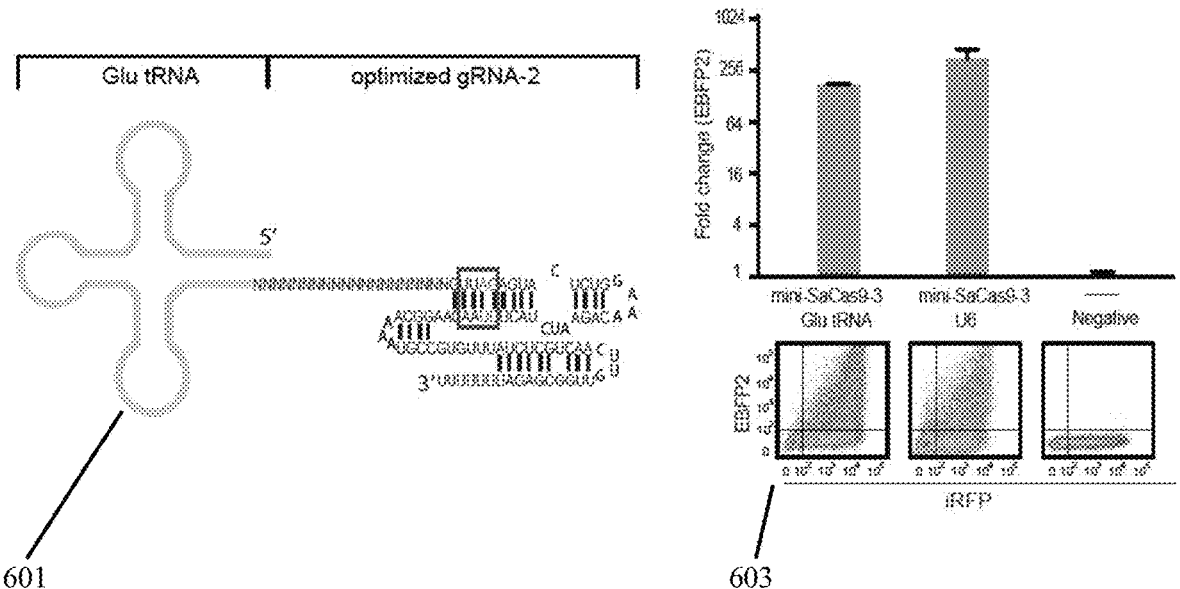
FIG. 6 is a diagram of Glutamine (Glu) tRNA used as the promoter to express the optimized gRNA-2.

FIG. 6 is a diagram of Glutamine (Glu) tRNA (601) used as the promoter to express the optimized gRNA-2. In this illustrative example, HEK293 cells are cotransfected with plasmids expressing the mini-SaCas9-3:VPR and gRNA-2 driven by either the Glu RNA or the U6 promoter. Representative flow cytometry scatter plots (603) are shown on the right. The constitutively expressed iRFP is used as a transfection control. Data are shown as the mean±SEM fold change of EBFP2 fluorescence from three independent replicates measured by using flow cytometer 48 h after transfection into HEK293 cells. In this illustrative embodiment, ~50% transactivation activity is obtained when using glutamine tRNA instead of the U6 promoter to drive gRNA expression.

Improving the DNA cleavage specificity of the CRISPR/Cas9 system is essential for future clinical applications. Dimerization of a hybrid protein in which FokI nuclease domain is fused to the N-terminal but not to the C-terminal of dSpCas9 improves the DNA cleavage specificity in the PAM-out orientation. Furthermore, truncated gRNAs with shorter regions of target complementarity decrease the off-target cleavage efficiency.

In the following illustrative embodiments, the effect of the compact SaCas9 derivatives on DNA cleavage and base editing is further disclosed.

Figure 7:
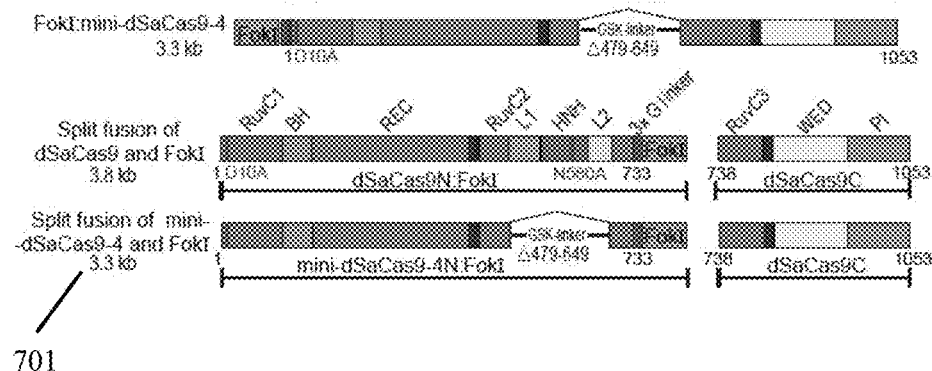
FIG. 7 is a diagram of domain organization of dSaCas9 variants including split dSaCas9 and split mini-dSaCas9-4 fused with the FokI domain.

FIG. 7 is a diagram of domain organization of dSaCas9 variants (701) including split dSaCas9 and split mini-dSaCas9-4 fused with the FokI domain and additionally includes FokI fused to the N terminal of dSaCas9 and mini-dSaCas9-4.

Figure 8:
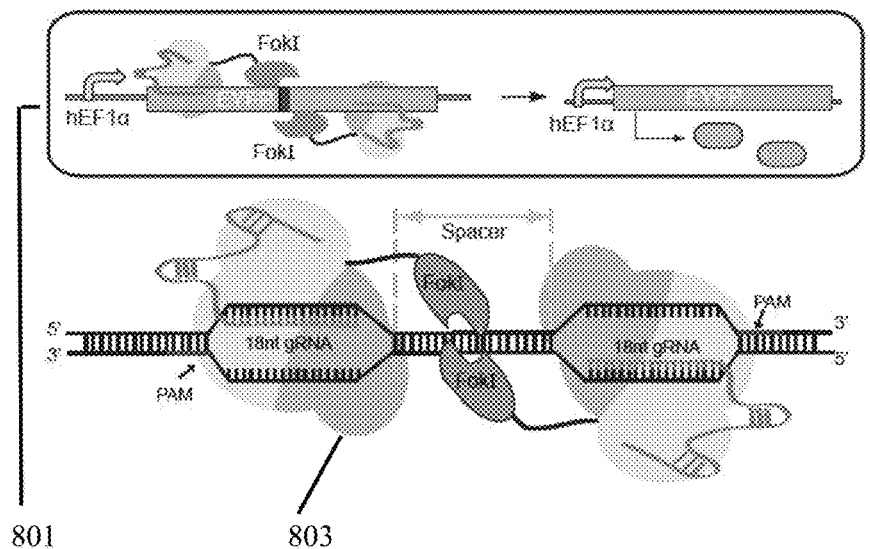
FIG. 8 is a diagram of the EYFP reconstitution assay to demonstrate the DNA cleavage efficiency and illustration of DNA cleavage by the dimeric FokI nuclease fused to split dSaCas9 and split minidSaCas9-4.

FIG. 8 is a diagram (801) of the EYFP reconstitution assay to demonstrate the DNA cleavage efficiency and illustration (803) of DNA cleavage by the dimeric FokI nuclease fused to split dSaCas9 or split minidSaCas9-4. EYFP reconstitution assay to evaluate the DNA cleavage efficiency of dSaCas9 derivatives fused with FokI along with two truncated gRNAs that respectively containing 18-nt sequences complementary to the target. In one illustrative embodiment, DNA cleavage activity is not detected when FokI is fused to the N-terminal of mini-SaCas9-2. One possible reason is that the FokI in this protein architecture may be distal to the target DNA. However, as the predicted distance between the N-terminal and the C-terminal of the FokI nuclease domain is 35 Å, which makes challenging to find an appropriate insertion position in the middle of the dSaCas9. In an alternate embodiment, dSaCas9 is split at residue 733 and fused the FokI after the splitting point with a triplicate C-linker ("GGGGS"). In an alternative illustrative embodiment the first four residues of the C-terminal fragment (Δ734-737) that might interfere with the reconstitution of two split fragments is removed. The split dSaCas9 or split mini-dSaCas9-4 without the HNH domain results in ~8% to 30% of the EYFP expression level induced by the wild-type SaCas9, with a spacer ranging from 12 bp to 24 bp in the PAM-out orientation.

Figure 9:
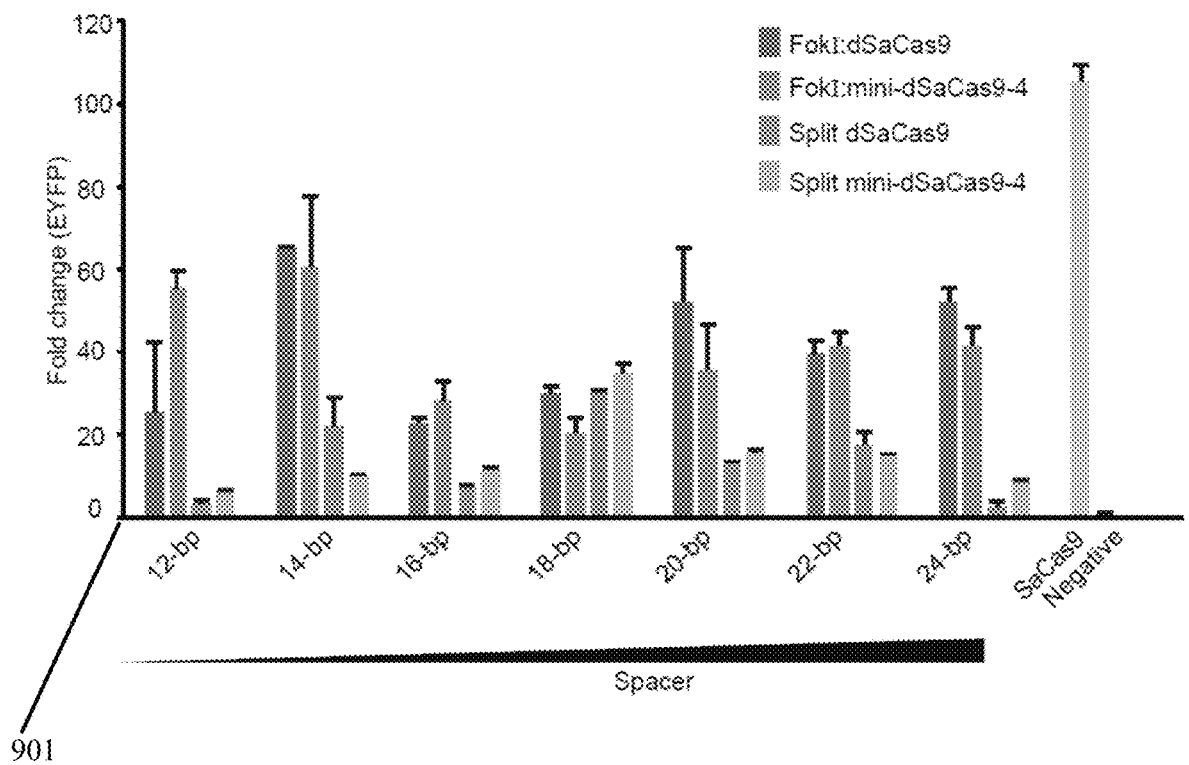
FIG. 9 is a graphical representation of DNA cleavage efficiency by the split dSaCas9 variants with a spacer length ranging from 12-bp to 24-bp.

FIG. 9 is a graphical representation (901) of DNA cleavage efficiency by the split dSaCas9 variants with a spacer length ranging from 12-bp to 24-bp. DNA cleavage efficiency by the split dSaCas9:FokI, the split mini-dSaCas9-4:FokI and FokI fused to the N terminal of dSaCas9 and mini-dSacas9-4 with a spacer length ranging from 12-bp to 24-bp. Each bar shows mean fold changes (mean±SEM; n=3) of EYFP fluorescence measured by using flow cytometer 48 h after transfection in HEK293 cells.

In the next illustrative embodiments, construction of the compact CRISPR/Cas system for transcription activation is further detailed.

Figure 10:
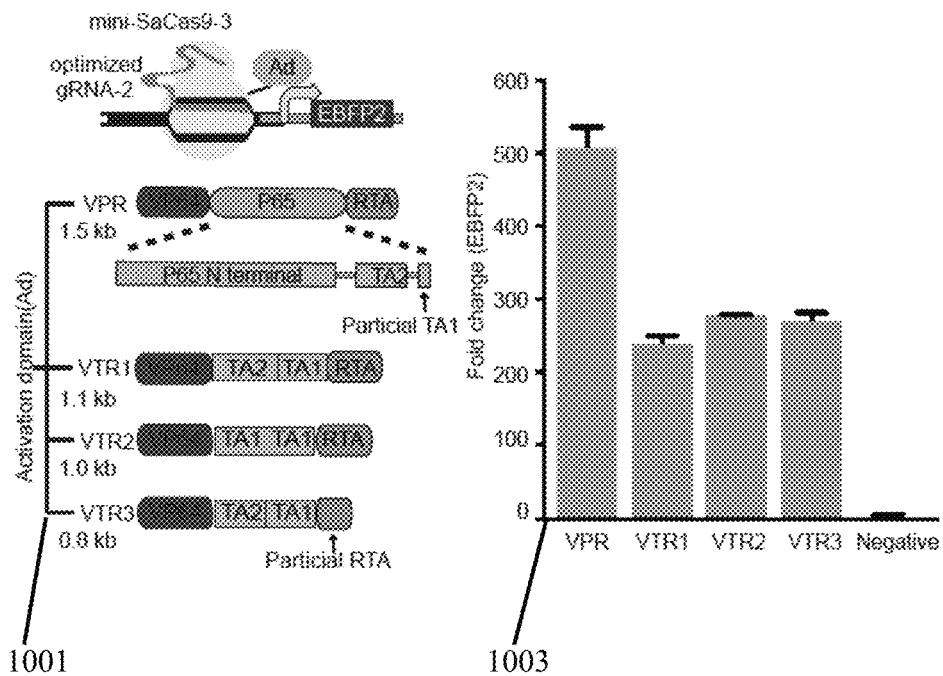
FIG. 10 is a schematic representation of VPR, VTR1, VTR2 and VTR3 transcription activation domain and their corresponding gene activation efficiency evaluated by using the EBFP2 reporting system.

FIG. 10 is a schematic representation (1001) of VPR, VTR1, VTR2 and VTR3 transcription activation domain and graphical representation (1003) of the corresponding gene activation efficiency evaluated by using the EBFP2 reporting system. In the illustrative embodiment, compact transcription activators based on dCas9-VPR are engineered. The entire P65 contains a DNA binding domain in the N-terminal, and two transactivation domains (TA1 and TA2) in the C-terminal. However, only the TA2 and the partial TA1 are included in the tripartite VPR domain. To reduce the size of dCas9-VPR, mini-SaCas9-3:VTR1 is constructed by replacing the P65 domain in the VPR with the TA1 and TA2 domains. In a further illustrative embodiment, the P65 domain in the VPR with two repeats of the TA1 domain is constructed and termed VTR2. The VTR1 and VTR2 domains retain 45% and 21% transactivation efficiency of the VPR domain respectively. VTR3 is additionally depicted and is approximately 200 bp shorter than VTR2 and VTR1 making it an optimal illustrative embodiment.

Figure 11:
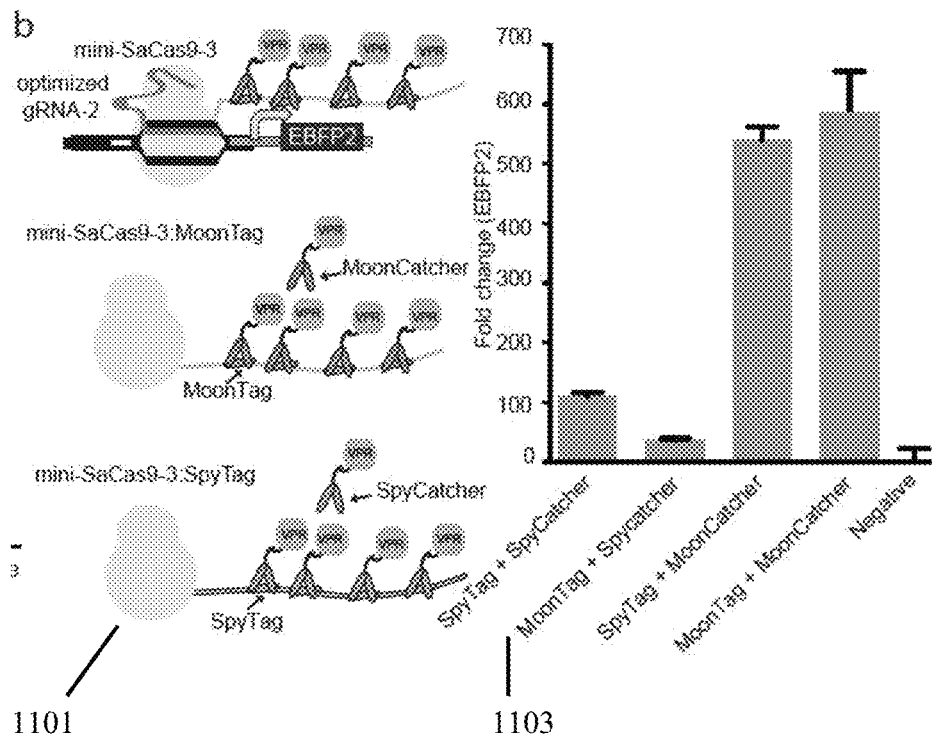
FIG. 11 is a schematic representation of the SpyTag and MoonTag repeating array for transcription activation with corresponding gene activation efficiency data.

FIG. 11 is a schematic representation (1101) of the SpyTag and MoonTag repeating array for transcription activation with graphical representation (1103) for corresponding gene activation efficiency data. The corresponding gene activation efficiency was evaluated by using the EBFP2 reporting system utilizing optimized gRNA-2 in the illustrative embodiments. Data are shown as the mean fold change (mean±SEM; n=3) of EBFP2 fluorescence measured by using flow cytometer 72 h after transfection into HEK293 cells.

Recently, a 13-residue peptide tag (SpyTag) derived from *Streptococcus pyogenes* fibronectin-binding protein (FbaB) has been shown to form a covalent bond with its 116-residue binding partner, called SpyCatcher.

In the illustrative embodiment, a repeating peptide array with a smaller size than the SunTag system is constructed by fusing four tandem repeats of SpyTag to the C-terminal of mini-SaCas9-3 and fusing the SpyCatcher with the VPR domain, allowing spontaneous assembly of a VPR transactivation scaffold in cells. The SpyTag system induces the expression of the enhanced blue fluorescent protein 2 (EBFP2) reporter gene to 100-fold compared to the negative control. In the illustrative embodiment, by searching for the homologue of SpyTag and SpyCatcher, a putative protein is found (accession No. WP_054278706) from *Streptococcus phocae* with 60% sequence similarity to the FbaB. In the illustrative embodiment, this protein is split similarly to SpyTag and SpyCatcher. As a direct and intended consequence of the illustrative embodiment, a similar scaffold system called the MoonTag system is hereby disclosed and implemented by fusing four tandem repeats of the 13-residue MoonTag to the mini-SaCas9-3 and making a hybrid of the MoonCatcher and VPR domains. Although the MoonTag system was not orthogonal to the SpyTag system, the MoonTag system is 5-fold more efficient to activate the EBFP2 expression.

Figure 12:
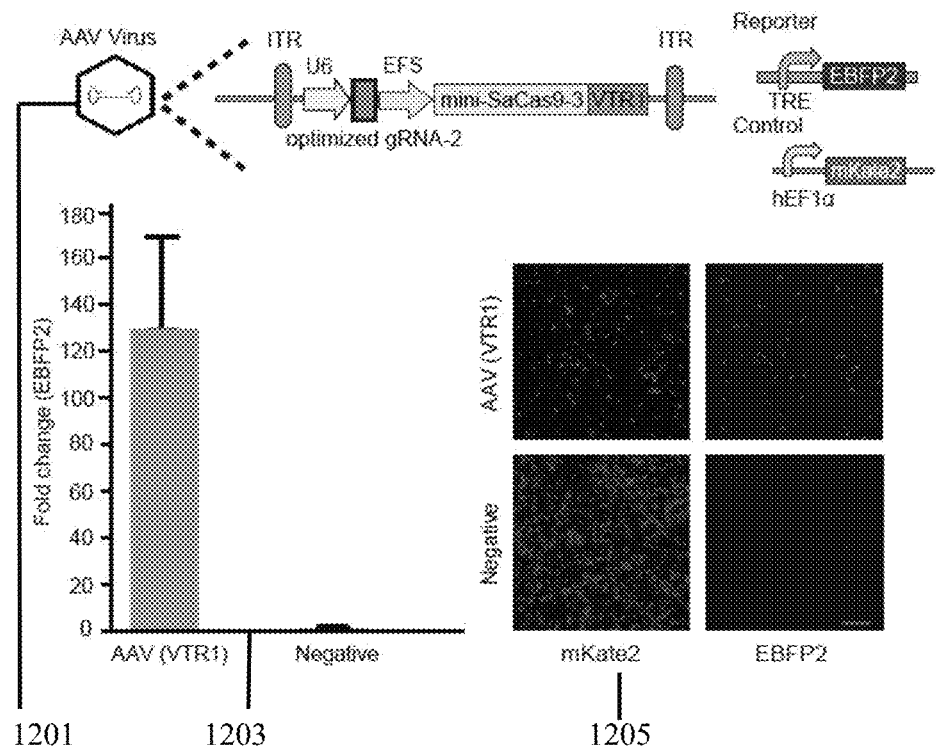
FIG. 12 is a schematic representation of transcription activation by using a single AAV loaded with the compact CRISPR/Cas9 system with a graphical illustration of an activation efficiency of EBFP2.

FIG. 12 is a schematic representation (1201) of transcription activation by using a single AAV loaded with the compact CRISPR/Cas9 system with a graphical illustration (1203) of an activation efficiency of EBFP2. In the illustrative example, transcription activation by using a single AAV loaded with the compact CRISPR/Cas9 system that contains the mini-SaCas9-3:VTR1 and U6-driven optimized gRNA-2 is depicted. The plasmid DNAs that encode the EBFP2 reporter gene and the mKate2 control gene are introduced into HEK293 cells by transient transfection, following by the AAV infection. The lower panel shows the activation efficiency of EBFP2 after infection of the AAV encoding the mini-SaCas9-3:VTR1 and the representative microscopic images (1205). Scale bar in images represents 200 μm. Data are shown as the mean fold change (mean±SEM; n=3) of EBFP2 fluorescence measured by using flow cytometer 72 hours after transfection and AAV infection. In this illustrative embodiment, a single. AAV virus is produced that encoded the constitutively expressed mini-SaCas9-3:VTR1 and the optimized gRNA that targeted the IRE promoter. A TREdriven EBFP2 reporter gene is introduced into HEK293 cells by transient transfection. In the illustrative embodiment, the AAV infection activated the EBFP2 expression up to ~130-fold over the negative control in the HEK293 cells, which was also more efficient than AAV virus loaded with the mini-SaCas9-3:VP64.

Figure 13:
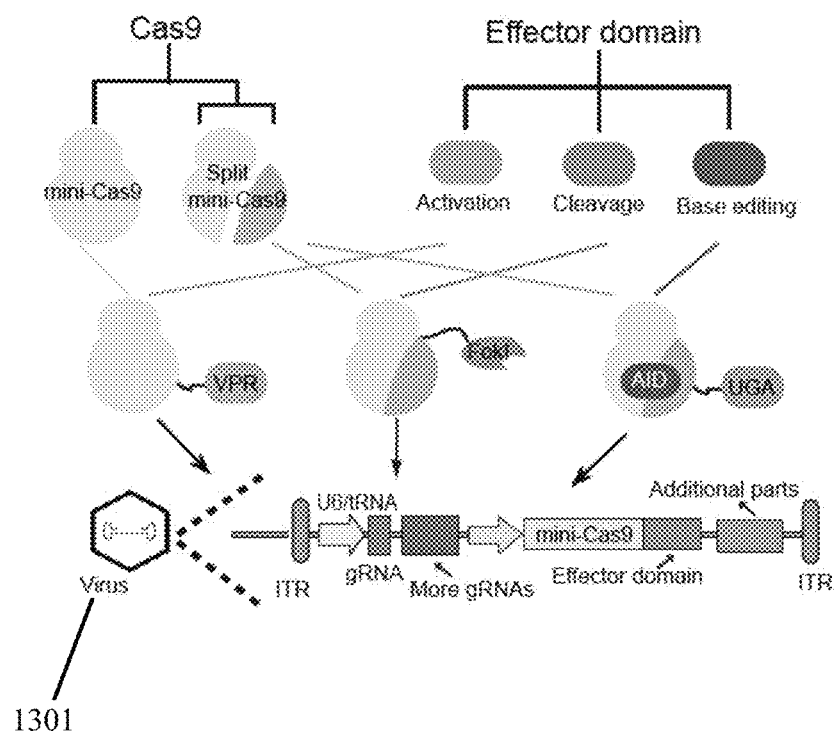
FIG. 13 is a schematic representation of packaging mini-Cas9, effector domain, gRNA expression cassette and additional parts in a single AAV vector for transcription activation, DNA cleavage and base editing.

FIG. 13 is a schematic representation (1301) of packaging mini-Cas9, effector domain, gRNA expression cassette and additional parts in a single AAV vector for transcription activation, DNA cleavage and base editing. By combining the illustrative embodiments to a broad working example, a set of compact Cas9 derivatives are engineered by deleting conserved HNH and/or REC-C domains based on the structural information across variant class 2 CRISPR effectors. In addition, a novel strategy to engineer the dimeric gRNA-guided nuclease by splitting the mini-dSaCas9 and fusing the FokI domain right after the split point is disclosed, which can increase the on-target DNA cleavage efficiency and potentially reduce the off-target effect because of a closer proximity of dimeric FokI nuclease to the target sequence. By combining the optimized and compact gRNA expression cassette and the downsized SaCas9 derivatives, a practical approach is disclosed to load the entire CRISPR/Cas system with different effector domains for transactivation, DNA cleavage and base editing into a single AAV virus. Such an all-in-one AAV-CRISPR/Cas9 system will be particularly appealing in biomedical applications that require safe and efficient delivery in vivo.

Figure 14:
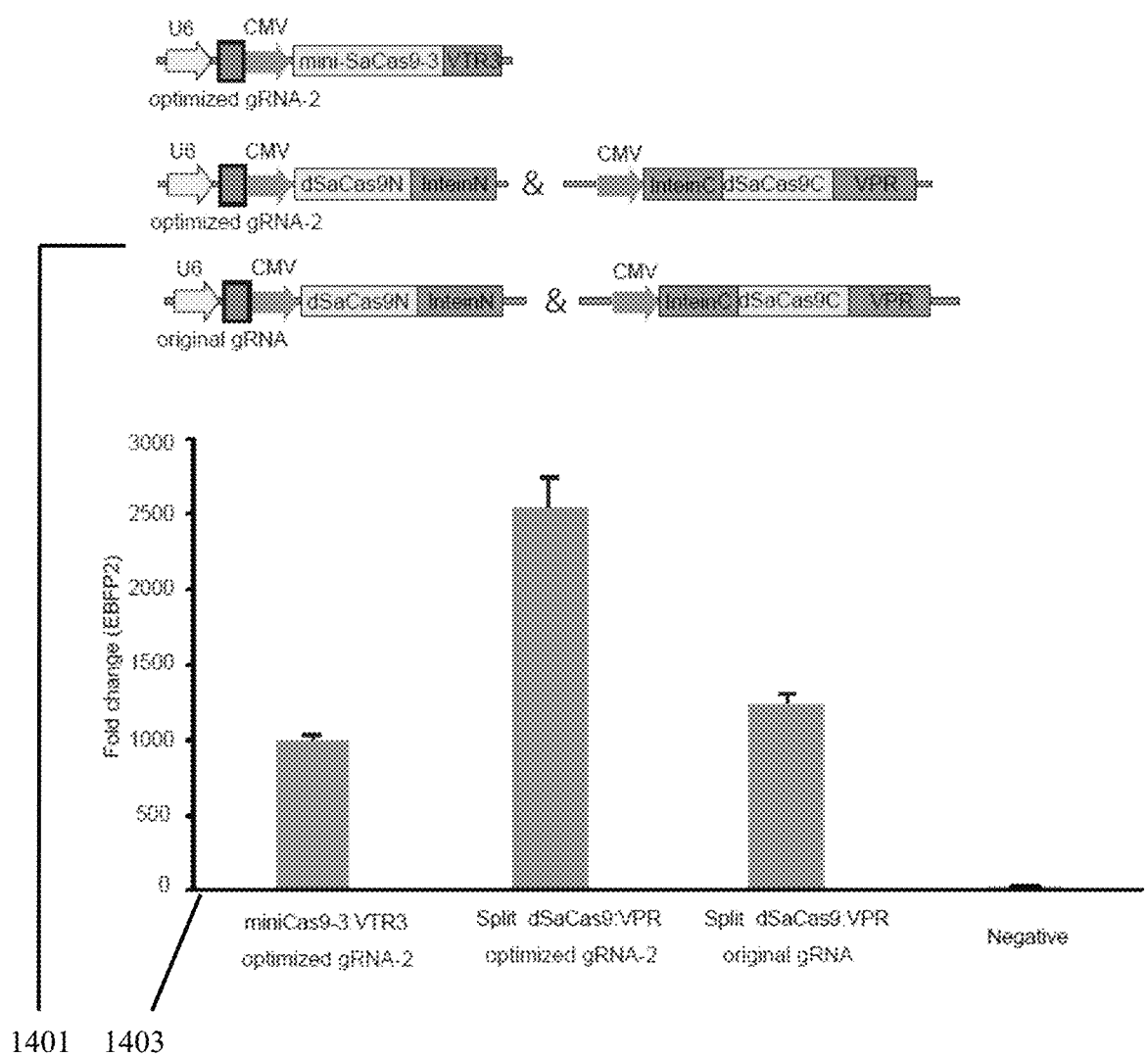
FIG. 14 is a schematic representation of miniSaCas9-3 and Split SaCas9 and the corresponding miniSaCas9-3 and Split SaCas9 activation efficiency.

FIG. 14 is a schematic representation (1401) of miniSaCas9-3 and Split SaCas9 and graphical data (1403) of the corresponding miniSaCas9-3 and Split SaCas9 activation efficiency.

Figure 15:
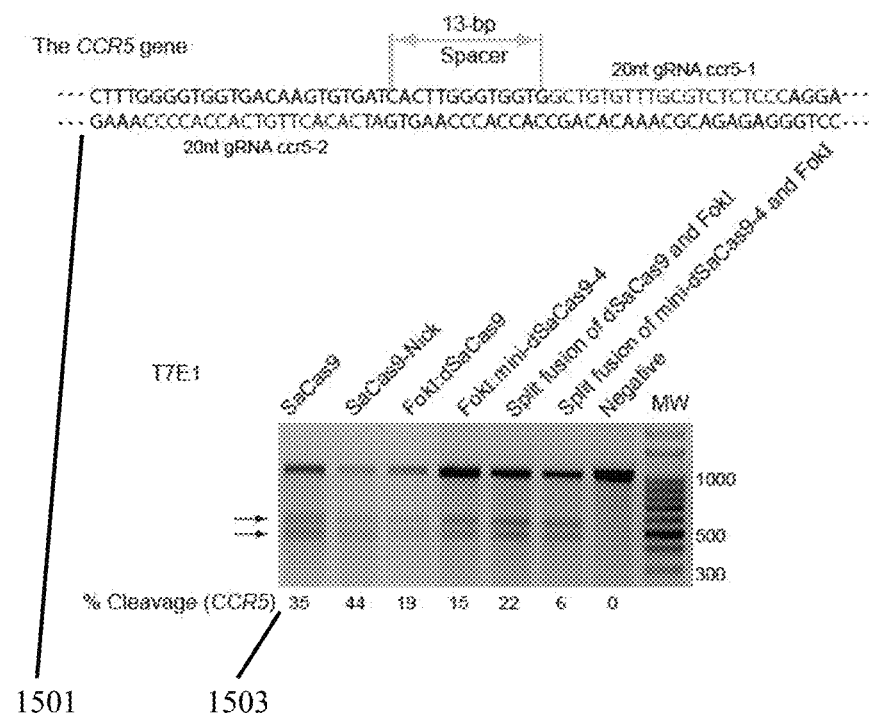
FIG. 15 is a genetic sequence illustration of CCR5 gene illustrating spacer region and corresponding gel agarose graphical data.

FIG. 15 is a genetic sequence illustration (1501) of CCR5 gene illustrating spacer region and gel electrophoresis graphical data (1503) illustrating CCR5 gene relative percentage of cleavage.

In the description, numerous specific details are set forth in order to provide a thorough understanding of the present embodiments. It will be apparent, however, to one having ordinary skill in the art that the specific detail need not be employed to practice the present embodiments. In other instances, well-known materials or methods have not been described in detail in order to avoid obscuring the present embodiments.

Reference throughout this specification to "one embodiment", "an embodiment", "one example" or "an example" means that a particular feature, structure or characteristic described in connection with the embodiment or example is included in at least one embodiment of the present embodiments. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus.

Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

INDUSTRIAL APPLICABILITY

The claimed invention has industrial applicability in biomedical and industrial biotechnology applications. With greater particularity, the improved Cas9 system provides greater gene editing and regulatory control capabilities over traditional Cas9 systems.

Sequence Listing Free Text

The instant application contains a Sequence Listing which has been submitted in ASCII format and is hereby incorporated by reference in its entirety. Said ASCII copy, created on Apr. 28, 2017, is named ZX2seqlist_ST25.txt and is 225 kbytes in size.

```
Sequence Listing
gRNAa
                                             SEQ ID NO: 1
TACGTTCTCTATCACTGATA gRNAb
                                             SEQ ID NO: 2
TACGTTCTCTATCACTGATA crRNAa
```

```
                                            -continued
                                                      SEQ ID NO: 3
CTCCCTATCAGTGATAGAGAACG gRNAc
                                                      SEQ ID NO: 4
CGTTCTCTATCACTGATA gRNAd
                                                      SEQ ID NO: 5
ACTAGAAATTCACCGAGC gRNA-15bp
                                                      SEQ ID NO: 6
CTCACTCAACAGTGATAGA gRNA-12bp
                                                      SEQ ID NO: 7
TTGCTCACTCAACAGTGATAG dSpCas9:VPR
                                                      SEQ ID NO: 8
MPKKKRKVGGGSPGMDKKYSIGLAIGTNSVGWAVITDEYKVPS
KKFKVLGNTDRHSIKKNLIGALLFDSGETAEATRLKRTARRRYT
RRKNRICYLQEIFSNEMAKVDDSFFHRLEESFLVEEDKKHERHPI
FGNIVDEVAYHEKYPTIYHLRKKLVDSTDKADLRLIYLALAHMI
KFRGHFLIEGDLNPDNSDVDKLFIQLVQTYNQLFEENPINASGVD
AKAILSARLSKSRRLENLIAQLPGEKKNGLFGNLIALSLGLTPNF
KSNFDLAEDAKLQLSKDTYDDDLDNLLAQIGDQYADLFLAAKN
LSDAILLSDILRVNTEITKAPLSASMIKRYDEHHQDLTLLKALVR
QQLPEKYKEIFFDQSKNGYAGYIDGGASQEEFYKFIKPILEKMDG
TEELLVKLNREDLLRKQRTFDNGSIPHQIHLGELHAILRRQEDFY
PFLKDNREKIEKILTFRIPYYVGPLARGNSRFAWMTRKSEETITP
WNFEEVVDKGASAQSFIERMTNFDKNLPNEKVLPKHSLLYEYFT
VYNELTKVKYVTEGMRKPAFLSGEQKKAIVDLLFKTNRKVTVK
QLKEDYFKKIECFDSVEISGVEDRFNASLGTYHDLLKIIKDKDFL
DNEENEDILEDIVLTLTLFEDREMIEERLKTYAHLFDDKVMKQL
KRRRYTGWGRLSRKLINGIRDKQSGKTILDFLKSDGFANRNFMQ
LIHDDSLTFKEDIQKAQVSGQGDSLHEHIANLAGSPAIKKGILQT
VKVVDELVKVMGRHKPENIVIEMARENQTTQKGQKNSRERMK
RIEEGIKELGSQILKEHPVENTQLQNEKLYLYYLQNGRDMYVDQ
ELDINRLSDYDVDAIVPQSFLKDDSIDNKVLTRSDKNRGKSDNV
PSEEVVKKMKNYWRQLLNAKLITQRKFDNLTKAERGGLSELDK
AGFIKRQLVETRQITKHVAQILDSRMNTKYDENDKLIREVKVITL
KSKLVSDFRKDFQFYKVREINNYHHAHDAYLNAVVGTALIKKY
PKLESEFVYGDYKVYDVRKMIAKSEQEIGKATAKYFFYSNIMNF
FKTEITLANGEIRKRPLIETNGETGEIVWDKGRDFATVRKVLSMP
QVNIVKKTEVQTGGFSKESILPKRNSDKLIARKKDWDPKKYGGF
DSPTVAYSVLVVAKVEKGKSKKLKSVKELLGITIMERSSFEKNPI
DFLEAKGYKEVKKDLIIKLPKYSLFELENGRKRMLASAGELQKG
NELALPSKYVNFLYLASHYEKLKGSPEDNEQKQLFVEQHKHYL
DEIIEQISEFSKRVILADANLDKVLSAYNKHRDKPIREQAENIIHL
```

```
                                            -continued
FTLTNLGAPAAFKYFDTTIDRKRYTSTKEVLDATLIHQSITGLYE
TRIDLSQLGGDTSRADPKKKRKVEASGSGRADALDDFDLDMLG
SDALDDFDLDMLGSDALDDFDLDMLGSDALDDFDLDMLINSRS
QYLPDTDDRHRIEEKRKRTYETFKSIMKKSPFSGPTDPRPPPRRIA
VPSRSSASVPKPAPQPYPFTSSLSTINYDEFPTMVFPSGQISQASA
LAPAPPQVLPQAPAPAPAPAMVSALAQAPAPVPVLAPGPPQAVA
PPAPKPTQAGEGTLSEALLQLQFDDEDLGALLGNSTDPAVFTDL
ASVDNSEFQQLLNQGIPVAPHTTEPMLMEYPEAITRLVTGAQRP
PDPAPAPLGAPGLPNGLLSGDEDFSSIADMDFSALLGSGSGSRDS
REGMFLPKPEAGSAISDVFEGREVCQPKRIRPFHPPGSPWANRPL
PASLAPTPTGPVHEPVGSLTPAPVPQPLDPAPAVTPEASHLLEDP
DEETSQAVKALREMADTVIPQKEEAAICGQMDLSHPPPRGHLDE
LTTTLESMTEDLNLDSPLTPELNEILDTFLNDECLLHAMHISTGLS
IFDTSLF mini-dSpCas9-1:VPR
                                                      SEQ ID NO: 9
MPKKKRKVGGGSPGMDKKYSIGLAIGTNSVGWAVITDEYKVPS
KKFKVLGNTDRHSIKKNLIGALLFDSGETAEATRLKRTARRRYT
RRKNRICYLQEIFSNEMAKVDDSFFHRLEESFLVEEDKKHERHPI
FGNIVDEVAYHEKYPTIYHLRKKLVDSTDKADLRLIYLALAHMI
KFRGHFLIEGDLNPDNSDVDKLFIQLVQTYNQLFEENPINASGVD
AKAILSARLSKSRRLENLIAQLPGEKKNGLFGNLIALSLGLTPNF
KSNFDLAEDAKLQLSKDTYDDDLDNLLAQIGDQYADLFLAAKN
LSDAILLSDILRVNTEITKAPLSASMIKRYDEHHQDLTLLKALVR
QQLPEKYKEIFFDQSKNGYAGYIDGGASQEEFYKFIKPILEKMDG
TEELLVKLNREDLLRKQRTFDNGSIPHQIHLGELHAILRRQEDFY
PFLKDNREKIEKILTFRIPYYVGPLARGNSRFAWMTRKSEETITP
WNFEEVVDKGASAQSFIERMTNFDKAQVSGQGDSLHEHIANLA
GSPAIKKGILQTVKVVDELVKVMGRHKPENIVIEMARENQTTQK
GQKNSRERMKRIEEGIKELGSQILKEHPVENTQLQNEKLYLYYL
QNGRDMYVDQELDINRLSDYDVDAIVPQSFLKDDSIDNKVLTRS
DKNRGKSDNVPSEEVVKKMKNYWRQLLNAKLITQRKFDNLTK
AERGGLSELDKAGFIKRQLVETRQITKHVAQILDSRMNTKYDEN
DKLIREVKVITLKSKLVSDFRKDFQFYKVREINNYHHAHDAYLN
AVVGTALIKKYPKLESEFVYGDYKVYDVRKMIAKSEQEIGKAT
AKYFFYSNIMNFFKTEITLANGEIRKRPLIETNGETGEIVWDKGR
DFATVRKVLSMPQVNIVKKTEVQTGGFSKESILPKRNSDKLIAR
KKDWDPKKYGGFDSPTVAYSVLVVAKVEKGKSKKLKSVKELL
GITIMERSSFEKNPIDFLEAKGYKEVKKDLIIKLPKYSLFELENGR
KRMLASAGELQKGNELALPSKYVNFLYLASHYEKLKGSPEDNE
QKQLFVEQHKHYLDEIIEQISEFSKRVILADANLDKVLSAYNKHR
DKPIREQAENIIHLFTLTNLGAPAAFKYFDTTIDRKRYTSTKEVL
```

```
DATLIHQSITGLYETRIDLSQLGGDTSRADPKKKRKVEASGSGRA
DALDDFDLDMLGSDALDDFDLDMLGSDALDDFDLDMLGSDAL
DDFDLDMLINSRSQYLPDTDDRHRIEEKRKRTYETFKSIMKKSPF
SGPTDPRPPPRRIAVPSRSSASVPKPAPQPYPFTSSLSTINYDEFPT
MVFPSGQISQASALAPAPPQVLPQAPAPAPAPAMVSALAQAPAP
VPVLAPGPPQAVAPPAPKPTQAGEGTLSEALLQLQFDDEDLGAL
LGNSTDPAVFTDLASVDNSEFQQLLNQGIPVAPHTTEPMLMEYP
EAITRLVTGAQRPPDPAPAPLGAPGLPNGLLSGDEDFSSIADMDF
SALLGSGSGSRDSREGMFLPKPEAGSAISDVFEGREVCQPKRIRP
FHPPGSPWANRPLPASLAPTPTGPVHEPVGSLTPAPVPQPLDPAP
AVTPEASHLLEDPDEETSQAVKALREMADTVIPQKEEAAICGQM
DLSHPPPRGHLDELTTTLESMTEDLNLDSPLTPELNEILDTFLNDE
CLLHAMHISTGLSIFDTSLF
mini-dSpCas9-2:VPR
                                           SEQ ID NO: 10
MPKKKRKVGGGSPGMDKKYSIGLAIGTNSVGWAVITDEYKVPS
KKFKVLGNTDRHSIKKNLIGALLFDSGETAEATRLKRTARRRYT
RRKNRICYLQEIFSNEMAKVDDSFFHRLEESFLVEEDKKHERHPI
FGNIVDEVAYHEKYPTIYHLRKKLVDSTDKADLRLIYLALAHMI
KFRGHFLIEGDLNPDNSDVDKLFIQLVQTYNQLFEENPINASGVD
AKAILSARLSKSRRLENLIAQLPGEKKNGLFGNLIALSLGLTPNF
KSNFDLAEDAKLQLSKDTYDDDLDNLLAQIGDQYADLFLAAKN
LSDAILLSDILRVNTEITKAPLSASMIKRYDEHHQDLTLLKALVR
QQLPEKYKEIFFDQSKNGYAGYIDGGASQEEFYKFIKPILEKMDG
TEELLVKLNREDLLRKQRTFDNGSIPHQIHLGELHAILRRQEDFY
PFLKDNREKIEKILTFRIPYYVGPLARGNSRFAWMTRKSEETITP
WNFEEVVDKGASAQSFIERMTNFDKNLPNEKVLPKHSLLYEYFT
VYNELTKVKYVTEGMRKPAFLSGEQKKAIVDLLFKTNRKVTVK
QLKEDYFKKIECFDSVEISGVEDRFNASLGTYHDLLKIIKDKDFL
DNEENEDILEDIVLTLTLFEDREMIEERLKTYAHLFDDKVMKQL
KRRRYTGWGRLSRKLINGIRDKQSGKTILDFLKSDGFANRNFMQ
LIHDDSLTFKEDIQKAQVSGQGDSLHEHIANLAGSPAIKKGILQT
VKVVDELVKVMGRHKPENIVIEMARENQTTQKGQKNITQRKFD
NLTKAERGGLSELDKAGFIKRQLVETRQITKHVAQILDSRMNTK
YDENDKLIREVKVITLKSKLVSDFRKDFQFYKVREINNYHHAHD
AYLNAVVGTALIKKYPKLESEFVYGDYKVYDVRKMIAKSEQEI
GKATAKYFFYSNIMNFFKTEITLANGEIRKRPLIETNGETGEIVW
DKGRDFATVRKVLSMPQVNIVKKTEVQTGGFSKESILPKRNSDK
LIARKKDWDPKKYGGFDSPTVAYSVLVVAKVEKGKSKKLKSV
KELLGITIMERSSFEKNPIDFLEAKGYKEVKKDLIIKLPKYSLFEL
ENGRKRMLASAGELQKGNELALPSKYVNFLYLASHYEKLKGSP
```

```
EDNEQKQLFVEQHKHYLDEIIEQISEFSKRVILADANLDKVLSAY
NKHRDKPIREQAENIIHLFTLTNLGAPAAFKYFDTTIDRKRYTST
KEVLDATLIHQSITGLYETRIDLSQLGGDTSRADPKKKRKVEASG
SGRADALDDFDLDMLGSDALDDFDLDMLGSDALDDFDLDMLG
SDALDDFDLDMLINSRSQYLPDTDDRHRIEEKRKRTYETFKSIM
KKSPFSGPTDPRPPPRRIAVPSRSSASVPKPAPQPYPFTSSLSTINY
DEFPTMVFPSGQISQASALAPAPPQVLPQAPAPAPAPAMVSALA
QAPAPVPVLAPGPPQAVAPPAPKPTQAGEGTLSEALLQLQFDDE
DLGALLGNSTDPAVFTDLASVDNSEFQQLLNQGIPVAPHTTEPM
LMEYPEAITRLVTGAQRPPDPAPAPLGAPGLPNGLLSGDEDFSSI
ADMDFSALLGSGSGSRDSREGMFLPKPEAGSAISDVFEGREVCQ
PKRIRPFHPPGSPWANRPLPASLAPTPTGPVHEPVGSLTPAPVPQP
LDPAPAVTPEASHLLEDPDEETSQAVKALREMADTVIPQKEEAA
ICGQMDLSHPPPRGHLDELTTTLESMTEDLNLDSPLTPELNEILD
TFLNDECLLHAMHISTGLSIFDTSLF
dSaCas9:VPR
                                           SEQ ID NO: 11
MPKKKRKVGGGSPGKRNYILGLAIGITSVGYGIIDYETRDVIDAG
VRLFKEANVENNEGRRSKRGARRLKRRRHRIQRVKKLLFDYN
LLTDHSELSGINPYEARVKGLSQKLSEEEFSAALLHLAKRRGVH
NVNEVEEDTGNELSTKEQISRNSKALEEKYVAELQLERLKKDGE
VRGSINRFKTSDYVKEAKQLLKVQKAYHQLDQSFIDTYIDLLET
RRTYYEGPGEGSPFGWKDIKEWYEMLMGHCTYFPEELRSVKYA
YNADLYNALNDLNNLVITRDENEKLEYYEKFQIIENVFKQKKKP
TLKQIAKEILVNEEDIKGYRVTSTGKPEFTNLKVYHDIKDITARK
EIIENAELLDQIAKILTIYQSSEDIQEELTNLNSELTQEEIEQISNLK
GYTGTHNLSLKAINLILDELWHTNDNQIAIFNRLKLVPKKVDLS
QQKEIPTTLVDDFILSPVVKRSFIQSIKVINAIIKKYGLPNDIIIELA
REKNSKDAQKMINEMQKRNRQTNERIEEIIRTTGKENAKYLIEKI
KLHDMQEGKCLYSLEAIPLEDLLNNPFNYEVDHIIPRSVSFDNSF
NNKVLVKQEEASKKGNRTPFQYLSSSDSKISYETFKKHILNLAK
GKGRISKTKKEYLLEERDINRFSVQKDFINRNLVDTRYATRGLM
NLLRSYFRVNNLDVKVKSINGGFTSFLRRKWKFKKERNKGYKH
HAEDALIIANADFIFKEWKKLDKAKKVMENQMFEEKQAESMPE
IETEQEYKEIFITPHQIKHIKDFKDYKYSHRVDKKPNRKLINDTLY
STRKDDKGNTLIVNNLNGLYDKDNDKLKKLINKSPEKLLMYHH
DPQTYQKLKLIMEQYGDEKNPLYKYYEETGNYLTKYSKKDNGP
VIKKIKYYGNKLNAHLDITDDYPNSRNKVVKLSLKPYRFDVYLD
NGVYKFVTVKNLDVIKKENYYEVNSKCYEEAKKLKKISNQAEFI
ASFYKNDLIKINGELYRVIGVNNDLLNRIEVNMIDITYREYLENM
NDKRPPHIIKTIASKTQSIKKYSTDILGNLYEVKSKKHPQIIKKGT
SRADPKKKRKVEASGSGRADALDDFDLDMLGSDALDDFDLDM
```

-continued

LGSDALDDFDLDMLGSDALDDFDLDMLINSRSQYLPDTDDRHRI

EEKRKRTYETFKSIMKKSPFSGPTDPRPPPRRIAVPSRSSASVPKP

APQPYPFTSSLSTINYDEFPTMVFPSGQISQASALAPAPPQVLPQA

PAPAPAPAMVSALAQAPAPVPVLAPGPPQAVAPPAPKPTQAGEG

TLSEALLQLQFDDEDLGALLGNSTDPAVFTDLASVDNSEFQQLL

NQGIPVAPHTTEPMLMEYPEAITRLVTGAQRPPDPAPAPLGAPG

LPNGLLSGDEDFSSIADMDFSALLGSGSGSRDSREGMFLPKPEAG

SAISDVFEGREVCQPKRIRPFHPPGSPWANRPLPASLAPTPTGPV

HEPVGSLTPAPVPQPLDPAPAVTPEASHLLEDPDEETSQAVKALR

EMADTVIPQKEEAAICGQMDLSHPPPRGHLDELTTTLESMTEDL

NLDSPLTPELNEILDTFLNDECLLHAMHISTGLSIFDTSLF mini-SaCas9-1:VPR
                                           SEQ ID NO: 12
MPKKKRKVGGGSPGKRNYILGLDIGITSVGYGIIDYETRDVIDAG

VRLFKEANVENNEGRRSKRGARRLKRRRRHRIQRVKKLLFDYN

LLTDHSELSGINPYEARVKGLSQKLSEEEFSAALLHLAKRRGVH

NVNEVEEDTGNELSTKEQISRNSKALEEKYVAELQLERLKKDGE

VRGSINRFKTSDYVKEAKQLLKVQKAYHQLDQSFIDTYIDLLET

RRTYYEGPGEGSPFGWKDIKEWYEMLGGGSGGGILSPVVKRSFI

QSIKVINAIIKKYGLPNDIIIELAREKNSKDAQKMINEMQKRNRQ

TNERIEEIIRTTGKENAKYLIEKIKLHDMQEGKCLYSLEAIPLEDL

LNNPFNYEVDHIIPRSVSFDNSFNNKVLVKQEENSKKGNRTPFQ

YLSSSDSKISYETFKKHILNLAKGKGRISKTKKEYLLEERDINRFS

VQKDFINRNLVDTRYATRGLMNLLRSYFRVNNLDVKVKSINGG

FTSFLRRKWKFKKERNKGYKHHAEDALIIANADFIFKEWKKLD

KAKKVMENQMFEEKQAESMPEIETEQEYKEIFITPHQIKHIKDFK

DYKYSHRVDKKPNRKLINDTLYSTRKDDKGNTLIVNNLNGLYD

KDNDKLKKLINKSPEKLLMYHHDPQTYQKLKLIMEQYGDEKNP

LYKYYEETGNYLTKYSKKDNGPVIKKIKYYGNKLNAHLDITDD

YPNSRNKVVKLSLKPYRFDVYLDNGVYKFVTVKNLDVIKKENY

YEVNSKCYEEAKKLKKISNQAEFIASFYKNDLIKINGELYRVIGV

NNDLLNRIEVNMIDITYREYLENMNDKRPPHIIKTIASKTQSIKKY

STDILGNLYEVKSKKHPQIIKKGTSRADPKKKRKVEASGSGRAD

ALDDFDLDMLGSDALDDFDLDMLGSDALDDFDLDMLGSDALD

DFDLDMLINSRSQYLPDTDDRHRIEEKRKRTYETFKSIMKKSPFS

GPTDPRPPPRRIAVPSRSSASVPKPAPQPYPFTSSLSTINYDEFPTM

VFPSGQISQASALAPAPPQVLPQAPAPAPAPAMVSALAQAPAPV

PVLAPGPPQAVAPPAPKPTQAGEGTLSEALLQLQFDDEDLGALL

GNSTDPAVFTDLASVDNSEFQQLLNQGIPVAPHTTEPMLMEYPE

AITRLVTGAQRPPDPAPAPLGAPGLPNGLLSGDEDFSSIADMDFS

ALLGSGSGSRDSREGMFLPKPEAGSAISDVFEGREVCQPKRIRPF

-continued

HPPGSPWANRPLPASLAPTPTGPVHEPVGSLTPAPVPQPLDPAPA

VTPEASHLLEDPDEETSQAVKALREMADTVIPQKEEAAICGQMD

LSHPPPRGHLDELTTTLESMTEDLNLDSPLTPELNEILDTFLNDEC

LLHAMHISTGLSIFDTSLF mini-SaCas9-2:VPR
                                           SEQ ID NO: 13
MPKKKRKVGGGSPGKRNYILGLDIGITSVGYGIIDYETRDVIDAG

VRLFKEANVENNEGRRSKRGARRLKRRRRHRIQRVKKLLFDYN

LLTDHSELSGINPYEARVKGLSQKLSEEEFSAALLHLAKRRGVH

NVNEVEEDTGNELSTKEQISRNSKALEEKYVAELQLERLKKDGE

VRGSINRFKTSDYVKEAKQLLKVQKAYHQLDQSFIDTYIDLLET

RRTYYEGPGEGSPFGWKDIKEWYEMLKRRRRHRILSPVVKRSFI

QSIKVINAIIKKYGLPNDIIIELAREKNSKDAQKMINEMQKRNRQ

TNERIEEIIRTTGKENAKYLIEKIKLHDMQEGKCLYSLEAIPLEDL

LNNPFNYEVDHIIPRSVSFDNSFNNKVLVKQEENSKKGNRTPFQ

YLSSSDSKISYETFKKHILNLAKGKGRISKTKKEYLLEERDINRFS

VQKDFINRNLVDTRYATRGLMNLLRSYFRVNNLDVKVKSINGG

FTSFLRRKWKFKKERNKGYKHHAEDALIIANADFIFKEWKKLD

KAKKVMENQMFEEKQAESMPEIETEQEYKEIFITPHQIKHIKDFK

DYKYSHRVDKKPNRKLINDTLYSTRKDDKGNTLIVNNLNGLYD

KDNDKLKKLINKSPEKLLMYHHDPQTYQKLKLIMEQYGDEKNP

LYKYYEETGNYLTKYSKKDNGPVIKKIKYYGNKLNAHLDITDD

YPNSRNKVVKLSLKPYRFDVYLDNGVYKFVTVKNLDVIKKENY

YEVNSKCYEEAKKLKKISNQAEFIASFYKNDLIKINGELYRVIGV

NNDLLNRIEVNMIDITYREYLENMNDKRPPHIIKTIASKTQSIKKY

STDILGNLYEVKSKKHPQIIKKGTSRADPKKKRKVEASGSGRAD

ALDDFDLDMLGSDALDDFDLDMLGSDALDDFDLDMLGSDALD

DFDLDMLINSRSQYLPDTDDRHRIEEKRKRTYETFKSIMKKSPFS

GPTDPRPPPRRIAVPSRSSASVPKPAPQPYPFTSSLSTINYDEFPTM

VFPSGQISQASALAPAPPQVLPQAPAPAPAPAMVSALAQAPAPV

PVLAPGPPQAVAPPAPKPTQAGEGTLSEALLQLQFDDEDLGALL

GNSTDPAVFTDLASVDNSEFQQLLNQGIPVAPHTTEPMLMEYPE

AITRLVTGAQRPPDPAPAPLGAPGLPNGLLSGDEDFSSIADMDFS

ALLGSGSGSRDSREGMFLPKPEAGSAISDVFEGREVCQPKRIRPF

HPPGSPWANRPLPASLAPTPTGPVHEPVGSLTPAPVPQPLDPAPA

VTPEASHLLEDPDEETSQAVKALREMADTVIPQKEEAAICGQMD

LSHPPPRGHLDELTTTLESMTEDLNLDSPLTPELNEILDTFLNDEC

LLHAMHISTGLSIFDTSLF mini-SaCas9-3:VPR
                                           SEQ ID NO: 14
MPKKKRKVGGGSPGKRNYILGLDIGITSVGYGIIDYETRDVIDAG

VRLFKEANVENNEGRRSKRGARRLKRRRRHRIQRVKKLLFDYN

LLTDHSELSGINPYEARVKGLSQKLSEEEFSAALLHLAKRRGVH

-continued

NVNEVEEDTGNELSTKEQISRNSKALEEKYVAELQLERLKKDGE
VRGSINRFKTSDYVKEAKQLLKVQKAYHQLDQSFIDTYIDLLET
RRTYYEGPGEGSPFGWKDIKEWYEMLKRRRRHRILSPVVKRSFI
QSIKVINAIIKKYGLPNDIIIELGSKRYATRGLMNLLRSYFRVNNL
DVKVKSINGGFTSFLRRKWKFKKERNKGYKHHAEDALIIANAD
FIFKEWKKLDKAKKVMENQMFEEKQAESMPEIETEQEYKEIFIT
PHQIKHIKDFKDYKYSHRVDKKPNRKLINDTLYSTRKDDKGNTL
IVNNLNGLYDKDNDKLKKLINKSPEKLLMYHHDPQTYQKLKLI
MEQYGDEKNPLYKYYEETGNYLTKYSKKDNGPVIKKIKYYGN
KLNAHLDITDDYPNSRNKVVKLSLKPYRFDVYLDNGVYKFVTV
KNLDVIKKENYYEVNSKCYEEAKKLKKISNQAEFIASFYKNDLI
KINGELYRVIGVNNDLLNRIEVNMIDITYREYLENMNDKRPPHII
KTIASKTQSIKKYSTDILGNLYEVKSKKHPQIIKKGTSRADPKKK
RKVEASGSGRADALDDFDLDMLGSDALDDFDLDMLGSDALDD
FDLDMLGSDALDDFDLDMLINSRSQYLPDTDDRHRIEEKRKRTY
ETFKSIMKKSPFSGPTDPRPPPRRIAVPSRSSASVPKPAPQPYPFTS
SLSTINYDEFPTMVFPSGQISQASALAPAPPQVLPQAPAPAPAPA
MVSALAQAPAPVPVLAPGPPQAVAPPAPKPTQAGEGTLSEALLQ
LQFDDEDLGALLGNSTDPAVFTDLASVDNSEFQQLLNQGIPVAP
HTTEPMLMEYPEAITRLVTGAQRPPDPAPAPLGAPGLPNGLLSG
DEDFSSIADMDFSALLGSGSGSRDSREGMFLPKPEAGSAISDVFE
GREVCQPKRIRPFHPPGSPWANRPLPASLAPTPTGPVHEPVGSLT
PAPVPQPLDPAPAVTPEASHLLEDPDEETSQAVKALREMADTVI
PQKEEAAICGQMDLSHPPPRGHLDELTTTLESMTEDLNLDSPLTP
ELNEILDTFLNDECLLHAMHISTGLSIFDTSLF dAsCpf1:VPR
SEQ ID NO: 15
MPKKKRKVGGGSPGMTQFEGFTNLYQVSKTLRFELIPQGKTLK
HIQEQGFIEEDKARNDHYKELKPIIDRIYKTYADQCLQLVQLDW
ENLSAAIDSYRKEKTEETRNALIEEQATYRNAIHDYFIGRTDNLT
DAINKRHAEIYKGLFKAELFNGKVLKQLGTVTTTEHENALLRSF
DKFTTYFSGFYENRKNVFSAEDISTAIPHRIVQDNFPKFKENCHIF
TRLITAVPSLREHFENVKKAIGIFVSTSIEEVFSFPFYNQLLTQTQI
DLYNQLLGGISREAGTEKIKGLNEVLNLAIQKNDETAHIIASLPH
RFIPLFKQILSDRNTLSFILEEFKSDEEVIQSFCKYKTLLRNENVLE
TAEALFNELNSIDLTHIFISHKKLETISSALCDHWDTLRNALYERR
ISELTGKITKSAKEKVQRSLKHEDINLQEIISAAGKELSEAFKQKT
SEILSHAHAALDQPLPTTLKKQEEKEILKSQLDSLLGLYHLLDWF
AVDESNEVDPEFSARLTGIKLEMEPSLSFYNKARNYATKKPYSV
EKFKLNFQMPTLASGWDVNKEKNNGAILFVKNGLYYLGIMPKQ
KGRYKALSFEPTEKTSEGFDKMYYDYFPDAAKMIPKCSTQLKA

-continued

VTAHFQTHTHTTPILLSNNFIEPLEITKEIYDLNNPEKEPKKFQTAYA
KKTGDQKGYREALCKWIDFTRDFLSKYTKTTSIDLSSLRPSSQY
KDLGEYYAELNPLLYHISFQRIAEKEIMDAVETGKLYLFQIYNK
DFAKGHHGKPNLHTLYWTGLFSPENLAKTSIKLNGQAELFYRPK
SRMKRMAHRLGEKMLNKKLKDQKTPIPDTLYQELYDYVNHRL
SHDLSDEARALLPNVITKEVSHEIIKDRRFTSDKFFFHVPITLNYQ
AANSPSKFNQRVNAYLKEHPETPIIGIARGERNLIYITVIDSTGKIL
EQRSLNTIQQFDYQKKLDNREKERVAARQAWSVVGTIKDLKQG
YLSQVIHEIVDLMIHYQAVVVLENLNFGFKSKRTGIAEKAVYQQ
FEKMLIDKLNCLVLKDYPAEKVGGVLNPYQLTDQFTSFAKMGT
QSGFLFYVPAPYTSKIDPLTGFVDPFVWKTIKNHESRKHFLEGFD
FLHYDVKTGDFILHFKMNRNLSFQRGLPGFMPAWDIVFEKNET
QFDAKGTPFIAGKRIVPVIENHRFTGRYRDLYPANELIALLEEKGI
VFRDGSNILPKLLENDDSHAIDTMVALIRSVLQMRNSNAATGED
YINSPVRDLNGVCFDSRFQNPEWPMDADANGAYHIALKGQLLL
NHLKESKDLKLQNGISNQDWLAYIQELRNTSRADPKKKRKVEA
SGSGRADALDDFDLDMLGSDALDDFDLDMLGSDALDDFDLDM
LGSDALDDFDLDMLINSRSQYLPDTDDRHRIEEKRKRTYETFKSI
MKKSPFSGPTDPRPPPRRIAVPSRSSASVPKPAPQPYPFTSSLSTIN
YDEFPTMVFPSGQISQASALAPAPPQVLPQAPAPAPAPAMVSAL
AQAPAPVPVLAPGPPQAVAPPAPKPTQAGEGTLSEALLQLQFDD
EDLGALLGNSTDPAVFTDLASVDNSEFQQLLNQGIPVAPHTTEP
MLMEYPEAITRLVTGAQRPPDPAPAPLGAPGLPNGLLSGDEDFS
SIADMDFSALLGSGSGSRDSREGMFLPKPEAGSAISDVFEGREVC
QPKRIRPFHPPGSPWANRPLPASLAPTPTGPVHEPVGSLTPAPVP
QPLDPAPAVTPEASHLLEDPDEETSQAVKALREMADTVIPQKEE
AAICGQMDLSHPPPRGHLDELTTTLESMTEDLNLDSPLTPELNEI
LDTFLNDECLLHAMHISTGLSIFDTSLF mini-AsCpf1-1:VPR
SEQ ID NO: 16
MPKKKRKVGGGSPGMTQFEGFTNLYQVSKTLRFELIPQGKTLK
HIQEQGFIEEDKARNDHYKELKPIIDRIYKTYADQCLQLVQLDW
ENLSAAIDSYRKEKTEETRNALIEEQATYRNAIHDYFIGRTDNLT
DAINKRHAEIYKGLFKAELFNGKVLKQLGTVTTTEHENALLRSF
DKFTTYFSGFYENRKNVFSAEDISTAIPHRIVQDNFPKFKENCHIF
TRLITAVPSLREHFENVKKAIGIFVSTSIEEVFSFPFYNQLLTQTQI
DLYNQLLGGISREAGTEKIKGLNEVLNLAIQKNDETAHIIASLPH
RFIPLFKQILSDRNTLSFILEEFGGGSYSVEKFKLNFQMPTLASGW
DVNKEKNNGAILFVKNGLYYLGIMPKQKGRYKALSFEPTEKTSE
GFDKMYYDYFPDAAKMIPKCSTQLKAVTAHFQTHTHTTPILLSNNF
IEPLEITKEIYDLNNPEKEPKKFQTAYAKKTGDQKGYREALCKW
IDFTRDFLSKYTKTTSIDLSSLRPSSQYKDLGEYYAELNPLLYHIS -continued FQRIAEKEIMDAVETGKLYLFQIYNKDFAKGHHGKPNLHTLYW
TGLFSPENLAKTSIKLNGQAELFYRPKSRMKRMAHRLGEKMLN
KKLKDQKTPIPDTLYQELYDYVNHRLSHDLSDEARALLPNVITK
EVSHEIIKDRRFTSDKFFFHVPITLNYQAANSPSKFNQRVNAYLK
EHPETPIIGIDRGERNLIYITVIDSTGKILEQRSLNTIQQFDYQKKL
DNREKERVAARQAWSVVGTIKDLKQGYLSQVIHEIVDLMIHYQ
AVVVLENLNFGFKSKRTGIAEKAVYQQFEKMLIDKLNCLVLKD
YPAEKVGGVLNPYQLTDQFTSFAKMGTQSGFLFYVPAPYTSKID
PLTGFVDPFVWKTIKNHESRKHFLEGFDFLHYDVKTGDFILHFK
MNRNLSFQRGLPGFMPAWDIVFEKNETQFDAKGTPFIAGKRIVP
VIENHRFTGRYRDLYPANELIALLEEKGIVFRDGSNILPKLLEND
DSHAIDTMVALIRSVLQMRNSNAATGEDYINSPVRDLNGVCFDS
RFQNPEWPMDADANGAYHIALKGQLLLNHLKESKDLKLQNGIS
NQDWLAYIQELRNTSRADPKKKRKVEASGSGRADALDDFDLD
MLGSDALDDFDLDMLGSDALDDFDLDMLGSDALDDFDLDMLI
NSRSQYLPDTDDRHRIEEKRKRTYETFKSIMKKSPFSGPTDPRPP
PRRIAVPSRSSASVPKPAPQPYPFTSSLSTINYDEFPTMVFPSGQIS
QASALAPAPPQVLPQAPAPAPAPAMVSALAQAPAPVPVLAPGPP
QAVAPPAPKPTQAGEGTLSEALLQLQFDDEDLGALLGNSTDPAV
FTDLASVDNSEFQQLLNQGIPVAPHTTEPMLMEYPEAITRLVTG
AQRPPDPAPAPLGAPGLPNGLLSGDEDFSSIADMDFSALLGSGSG
SRDSREGMFLPKPEAGSAISDVFEGREVCQPKRIRPFHPPGSPWA
NRPLPASLAPTPTGPVHEPVGSLTPAPVPQPLDPAPAVTPEASHL
LEDPDEETSQAVKALREMADTVIPQKEEAAICGQMDLSHPPPRG
HLDELTTTLESMTEDLNLDSPLTPELNEILDTFLNDECLLHAMHI
STGLSIFDTSLF dSaCas9N:FokI
SEQ ID NO: 17
MPKKKRKVGGGSPGKRNYILGLAIGITSVGYGIIDYETRDVIDAG
VRLFKEANVENNEGRRSKRGARRLKRRRHRIQRVKKLLFDYN
LLTDHSELSGINPYEARVKGLSQKLSEEEFSAALLHLAKRRGVH
NVNEVEEDTGNELSTKEQISRNSKALEEKYVAELQLERLKKDGE
VRGSINRFKTSDYVKEAKQLLKVQKAYHQLDQSFIDTYIDLLET
RRTYYEGPGEGSPFGWKDIKEWYEMLMGHCTYFPEELRSVKYA
YNADLYNALNDLNNLVITRDENEKLEYYEKFQIIENVFKQKKKP
TLKQIAKEILVNEEDIKGYRVTSTGKPEFTNLKVYHDIKDITARK
EIIENAELLDQIAKILTIYQSSEDIQEELTNLNSELTQEEIEQISNLK
GYTGTHNLSLKAINLILDELWHTNDNQIAIFNRLKLVPKKVDLS
QQKEIPTTLVDDFILSPVVKRSFIQSIKVINAIIKKYGLPNDIIIELA
REKNSKDAQKMINEMQKRNRQTNERIEEIIRTTGKENAKYLIEKI
KLHDMQEGKCLYSLEAIPLEDLLNNPFNYEVDHIIPRSVSFDNSF NNKVLVKQEEASKKGNRTPFQYLSSSDSKISYETFKKHILNLAK
GKGRISKTKKEYLLEERDINRFSVQKDFINRNLVDTRYATRGLM
NLLRSYFRVNNLDVKVKSINGGFTSFLRRKWKFKKERNKGYKH
HAEDALIIANADFIFKEWKKLDKAKKVMENQMFGGGSGGGSG
GGSLVKSELEEKKSELRHKLYVPHEYIELIEIARNSTQDRILEM
KVMEFFMKVYGYRGKHLGGSRKPDGAIYTVGSPIDYGVIVDTK
AYSGGYNLPIGQADEMQRYVEENQTRNKHINPNEWWKVYPSS
VTEFKFLFVSGHFKGNYKAQLTRLNHITNCNGAVLSVEELLIGG
EMIKAGTLTLEEVRRKFNNGEINFTSGGGSKRPAATKKAGQAK
KKKSR dSaCas9C
SEQ ID NO: 18
MPKKKRKVGGGSPGAESMPEIETEQEYKEIFITPHQIKHIKDFKD
YKYSHRVDKKPNRKLINDTLYSTRKDDKGNTLIVNNLNGLYDK
DNDKLKKLINKSPEKLLMYHHDPQTYQKLKLIMEQYGDEKNPL
YKYYEETGNYLTKYSKKDNGPVIKKIKYYGNKLNAHLDITDDY
PNSRNKVVKLSLKPYRFDVYLDNGVYKFVTVKNLDVIKKENYY
EVNSKCYEEAKKLKKISNQAEFIASFYKNDLIKINGELYRVIGVN
NDLLNRIEVNMIDITYREYLENMNDKRPPHIIKTIASKTQSIKKYS
TDILGNLYEVKSKKHPQIIKKGTSGGGSKRPAATKKAGQAKKK
KSR mini-dSaCas9-4N:FokI
SEQ ID NO: 19
MPKKKRKVGGGSPGKRNYILGLAIGITSVGYGIIDYETRDVIDAG
VRLFKEANVENNEGRRSKRGARRLKRRRHRIQRVKKLLFDYN
LLTDHSELSGINPYEARVKGLSQKLSEEEFSAALLHLAKRRGVH
NVNEVEEDTGNELSTKEQISRNSKALEEKYVAELQLERLKKDGE
VRGSINRFKTSDYVKEAKQLLKVQKAYHQLDQSFIDTYIDLLET
RRTYYEGPGEGSPFGWKDIKEWYEMLMGHCTYFPEELRSVKYA
YNADINNALNDLNNLVITRDENEKLEYYEKFQIIENVFKQKKKP
TLKQIAKEILVNEEDIKGYRVTSTGKPEFTNLKVYHDIKDITARK
EIIENAELLDQIAKILTIYQSSEDIQEELTNLNSELTQEEIEQISNLK
GYTGTHNLSLKAINLILDELWHTNDNQIAIFNRLKLVPKKVDLS
QQKEIPTTLVDDFILSPVVKRSFIQSIKVINAIIKKYGLPNDIIIELG
SKRYATRGLMNLLRSYFRVNNLDVKVKSINGGFTSFLRRKWKF
KKERNKGYKHHAEDALIIANADFIFKEWKKLDKAKKVMENQM
FGGGSGGGSGGGSLVKSELEEKKSELRHKLYVPHEYIELIEIAR
NSTQDRILEMKVMEFFMKVYGYRGKHLGGSRKPDGAIYTVGSP
IDYGVIVDTKAYSGGYNLPIGQADEMQRYVEENQTRNKHINPNE
WWKVYPSSVTEFKFLFVSGHFKGNYKAQLTRLNHITNCNGAVL
SVEELLIGGEMIKAGTLTLEEVRRKFNNGEINFTSGGGSKRPAAT
KKAGQAKKKKSR AID:dSaCas9:UGI

SEQ ID NO: 20

MPKKKRKVGGGSPGMSSETGPVAVDPTLRRRIEPHEFEVFFDPR
ELRKETCLLYEINWGGRHSIWRHTSQNTNKHVEVNFIEKFTTER
YFCPNTRCSITWFLSWSPCGECSRAITEFLSRYPHVTLFIYIARLY
HHADPRNRQGLRDLISSGVTIQIMTEQESGYCWRNFVNYSPSNE
AHWPRYPHLWVRLYVLELYCIILGLPPCLNILRRKQPQLTFFTIA
LQSCHYQRLPPHILWATGLKSGSETPGTSESATPEKRNYILGLAI
GITSVGYGIIDYETRDVIDAGVRLFKEANVENNEGRRSKRGARR
LKRRRRHRIQRVKKLLFDYNLLTDHSELSGINPYEARVKGLSQK
LSEEEFSAALLHLAKRRGVHNVNEVEEDTGNELSTKEQISRNSK
ALEEKYVAELQLERLKKDGEVRGSINRFKTSDYVKEAKQLLKV
QKAYHQLDQSFIDTYIDLLETRRTYYEGPGEGSPFGWKDIKEWY
EMLMGHCTYFPEELRSVKYAYNADLYNALNDLNNLVITRDENE
KLEYYEKFQIIENVFKQKKKPTLKQIAKEILVNEEDIKGYRVTST
GKPEFTNLKVYHDIKDITARKEIIENAELLDQIAKILTIYQSSEDIQ
EELTNLNSELTQEEIEQISNLKGYTGTHNLSLKAINLILDELWHTN
DNQIAIFNRLKLVPKKVDLSQQKEIPTTLVDDFILSPVVKRSFIQSI
KVINAIIKKYGLPNDIIIELAREKNSKDAQKMINEMQKRNRQTNE
RIEEIIRTTGKENAKYLIEKIKLHDMQEGKCLYSLEAIPLEDLLNN
PFNYEVDHIIPRSVSFDNSFNNKVLVKQEEASKKGNRTPFQYLSS
SDSKISYETFKKHILNLAKGKGRISKTKKEYLLEERDINRFSVQK
DFINRNLVDTRYATRGLMNLLRSYFRVNNLDVKVKSINGGFTSF
LRRKWKFKKERNKGYKHHAEDALIIANADFIFKEWKKLDKAKK
VMENQMFEEKQAESMPEIETEQEYKEIFITPHQIKHIKDFKDYKY
SHRVDKKPNRKLINDTLYSTRKDDKGNTLIVNNLNGLYDKDND
KLKKLINKSPEKLLMYHHDPQTYQKLKLIMEQYGDEKNPLYKY
YEETGNYLTKYSKKDNGPVIKKIKYYGNKLNAHLDITDDYPNSR
NKVVKLSLKPYRFDVYLDNGVYKFVTVKNLDVIKKENYYEVNS
KCYEEAKKLKKISNQAEFIASFYKNDLIKINGELYRVIGVNNDLL
NRIEVNMIDITYREYLENMNDKRPPHIIKTIASKTQSIKKYSTDIL
GNLYEVKSKKHPQIIKKGSGGSTNLSDIIEKETGKQLVIQESILML
PEEVEEVIGNKPESDILVHTAYDESTDENVMLLTSDAPEYKPWA
LVIQDSNGENKIKMLSGGSPPKKKRKV

AID:mini-dSaCas9-5:UGI

SEQ ID NO: 21

MPKKKRKVGGGSPGMSSETGPVAVDPTLRRRIEPHEFEVFFDPR
ELRKETCLLYEINWGGRHSIWRHTSQNTNKHVEVNFIEKFTTER
YFCPNTRCSITWFLSWSPCGECSRAITEFLSRYPHVTLFIYIARLY
HHADPRNRQGLRDLISSGVTIQIMTEQESGYCWRNFVNYSPSNE
AHWPRYPHLWVRLYVLELYCIILGLPPCLNILRRKQPQLTFFTIA
LQSCHYQRLPPHILWATGLKSGSETPGTSESATPEKRNYILGLAI
GITSVGYGIIDYETRDVIDAGVRLFKEANVENNEGRRSKRGARR
LKRRRRHRIQRVKKLLFDYNLLTDHSELSGINPYEARVKGLSQK
LSEEEFSAALLHLAKRRGVHNVNEVEEDTGNELSTKEQISRNSK
ALEEKYVAELQLERLKKDGEVRGSINRFKTSDYVKEAKQLLKV
QKAYHQLDQSFIDTYIDLLETRRTYYEGPGEGSPFGWKDIKEWY
EMLMGHCTYFPEELRSVKYAYNADLYNALNDLNNLVITRDENE
KLEYYEKFQIIENVFKQKKKPTLKQIAKEILVNEEDIKGYRVTST
GKPEFTNLKVYHDIKDITARKEIIENAELLDQIAKILTIYQSSEDIQ
EELTNLNSELTQEEIEQISNLKGYTGTHNLSLKAINLILDELWHTN
DNQIAIFNRLKLVPKKVDLSQQKEIPTTLVDDFILSPVVKRSFIQSI
KVINAIIKKYGLPNDIIIELGSKRYATRGLMNLLRSYFRVNNLDV
KVKSINGGFTSFLRRKWKFKKERNKGYKHHAEDALIIANADFIF
KEWKKLDKAKKVMENQMFEEKQAESMPEIETEQEYKEIFITPH
QIKHIKDFKDYKYSHRVDKKPNRKLINDTLYSTRKDDKGNTLIV
NNLNGLYDKDNDKLKKLINKSPEKLLMYHHDPQTYQKLKLIME
QYGDEKNPLYKYYEETGNYLTKYSKKDNGPVIKKIKYYGNKLN
AHLDITDDYPNSRNKVVKLSLKPYRFDVYLDNGVYKFVTVKNL
DVIKKENYYEVNSKCYEEAKKLKKISNQAEFIASFYKNDLIKING
ELYRVIGVNNDLLNRIEVNMIDITYREYLENMNDKRPPHIIKTIAS
KTQSIKKYSTDILGNLYEVKSKKHPQIIKKGSGGSTNLSDIIEKET
GKQLVIQESILMLPEEVEEVIGNKPESDILVHTAYDESTDENVML
LTSDAPEYKPWALVIQDSNGENKIKMLSGGSPPKKKRKV mini-dSaCas9-6N:AID

SEQ ID NO: 22

MPKKKRKVGGGSPGKRNYILGLAIGITSVGYGIIDYETRDVIDAG
VRLFKEANVENNEGRRSKRGARRLKRRRRHRIQRVKKLLFDYN
LLTDHSELSGINPYEARVKGLSQKLSEEEFSAALLHLAKRRGVH
NVNEVEEDTGNELSTKEQISRNSKALEEKYVAELQLERLKKDGE
VRGSINRFKTSDYVKEAKQLLKVQKAYHQLDQSFIDTYIDLLET
RRTYYEGPGEGSPFGWKDIKEWYEMLMGHCTYFPEELRSVKYA
YNADLYNALNDLNNLVITRDENEKLEYYEKFQIIENVFKQKKKP
TLKQIAKEILVNEEDIKGYRVTSTGKPEFTNLKVYHDIKDITARK
EIIENAELLDQIAKILTIYQSSEDIQEELTNLNSELTQEEIEQISNLK
GYTGTHNLSLKAINLILDELWHTNDNQIAIFNRLKLVPKKVDLS
QQKEIPTTLVDDFILSPVVKRSFIQSIKVINAIIKKYGLPNDIIIELA
REKGGGSGGGSMSSETGPVAVDPTLRRRIEPHEFEVFFDPRELRK
ETCLLYEINWGGRHSIWRHTSQNTNKHVEVNFIEKFTTERYFCP
NTRCSITWFLSWSPCGECSRAITEFLSRYPHVTLFIYIARLYHHAD
PRNRQGLRDLISSGVTIQIMTEQESGYCWRNFVNYSPSNEAHWP
RYPHLWVRLYVLELYCIILGLPPCLNILRRKQPQLTFFTIALQSCH
YQRLPPHILWATGLKSGSETPGTSESATPETSGGGSKRPAATKK
AGQAKKKKSR mini-dSaCas9-6C:UGI
SEQ ID NO: 23
MPKKKRKVGGGSPGTRYATRGLMNLLRSYFRVNNLDVKVKSI
NGGFTSFLRRKWFKKERNKGYKHHAEDALIIANADFIFKEWK
KLDKAKKVMENQMFEEKQAESMPEIETEQEYKEIFITPHQIKHIK
DFKDYKYSHRVDKKPNRKLINDTLYSTRKDDKGNTLIVNNLNG
LYDKDNDKLKKLINKSPEKLLMYHHDPQTYQKLKLIMEQYGDE
KNPLYKYYEETGNYLTKYSKKDNGPVIKKIKYYGNKLNAHLDI
TDDYPNSRNKVVKLSLKPYRFDVYLDNGVYKFVTVKNLDVIKK
ENYYEVNSKCYEEAKKLKKISNQAEFIASFYKNDLIKINGELYRV
IGVNNDLLNRIEVNMIDITYREYLENMNDKRPPHIIKTIASKTQSI
KKYSTDILGNLYEVKSKKHPQIIKKGSGGSTNLSDIIEKETGKQL
VIQESILMLPEEVEEVIGNKPESDILVHTAYDESTDENVMLLTSD
APEYKPWALVIQDSNGENKIKMLSGGSPPKKKRKV VTR1
SEQ ID NO: 24
GSGRADALDDFDLDMLGSDALDDFDLDMLGSDALDDFDLDML
GSDALDDFDLDMLINSALLQLQFDDEDLGALLGNSTDPAVFTDL
ASVDNSEFQQLLNQGIPVAPHTTEPMLMEYPEAITRLVTGAQRP
PDPAPAPLGAPGLPNGLLSGDEDFSSIADMDFSALLSQISSGSGSG
SRDSREGMFLPKPEAGSAISDVFEGREVCQPKRIRPFHPPGSPWA
NRPLPASLAPTPTGPVHEPVGSLTPAPVPQPLDPAPAVTPEASHL
LEDPDEETSQAVKALREMADTVIPQKEEAAICGQMDLSHPPPRG
HLDELTTTLESMTEDLNLDSPLTPELNEILDTFLNDECLLHAMHI
STGLSIFDTSLFTSGGGSKRPAATKKAGQAKKKKSR VTR2
SEQ ID NO: 25
GSGRADALDDFDLDMLGSDALDDFDLDMLGSDALDDFDLDML
GSDALDDFDLDMLINSRLVTGAQRPPDPAPAPLGAPGLPNGLLS
GDEDFSSIADMDFSALLSQISSGGGSRLVTGAQRPPDPAPAPLGA
PGLPNGLLSGDEDFSSIADMDFSALLSQISSGSGSGSRDSREGMF
LPKPEAGSAISDVFEGREVCQPKRIRPFHPPGSPWANRPLPASLA
PTPTGPVHEPVGSLTPAPVPQPLDPAPAVTPEASHLLEDPDEETS
QAVKALREMADTVIPQKEEAAICGQMDLSHPPPRGHLDELTTTL
ESMTEDLNLDSPLTPELNEILDTFLNDECLLHAMHISTGLSIFDTS
LFTSGGGSKRPAATKKAGQAKKKKSR SpyCatcher:VPR
SEQ ID NO: 26
MPKKKRKVGGGSPGGAMVDTLSGLSSEQGQSGDMTIEEDSATH
IKFSKRDEDGKELAGATMELRDSSGKTISTWISDGQVKDFYLYP
GKYTFVETAAPDGYEVATAITFTVNEQGQVTVNGKATKGDAHI
TGTSRADPKKKRKVEASGSGRADALDDFDLDMLGSDALDDFDL
DMLGSDALDDFDLDMLGSDALDDFDLDMLINSRSQYLPDTDDR
HRIEEKRKRTYETFKSIMKKSPFSGPTDPRPPPRRIAVPSRSSASV
PKPAPQPYPFTSSLSTINYDEFPTMVFPSGQISQASALAPAPPQVL
PQAPAPAPAPAMVSALAQAPAPVPVLAPGPPQAVAPPAPKPTQA
GEGTLSEALLQLQFDDEDLGALLGNSTDPAVFTDLASVDNSEFQ
QLLNQGIPVAPHTTEPMLMEYPEAITRLVTGAQRPPDPAPAPLG
APGLPNGLLSGDEDFSSIADMDFSALLGSGSGSRDSREGMFLPKP
EAGSAISDVFEGREVCQPKRIRPFHPPGSPWANRPLPASLAPTPT
GPVHEPVGSLTPAPVPQPLDPAPAVTPEASHLLEDPDEETSQAVK
ALREMADTVIPQKEEAAICGQMDLSHPPPRGHLDELTTTLESMT
EDLNLDSPLTPELNEILDTFLNDECLLHAMHISTGLSIFDTSLF 4x SpyTag
SEQ ID NO: 27
GGGSGGAHIVMVDAYKPTKGGSGGGGSGGAHIVMVDAYKYTK
GGSGGGGSGGAHIVMVDAYKPTKGGSGGGGSGGAHIVMVDAY
KPTK MoonCatcher:VPR
SEQ ID NO: 28
MPKKKRKVGGGSPGNHVIETEQNLPNEDGQSGNIIEQEDSKTLV
KFSKRDIKGNELAGATIELRDLSGKSIQSWVSDGKAKDFYLLPG
SYEFVETAAPEGYQIATKIMFTISTDGRITVDGQLVTGTGSGRAD
ALDDFDLDMLGSDALDDFDLDMLGSDALDDFDLDMLGSDALD
DFDLDMLINSRSQYLPDTDDRHRIEEKRKRTYETFKSIMKKSPFS
GPTDPRPPPRRIAVPSRSSASVPKPAPQPYPFTSSLSTINYDEFPTM
VFPSGQISQASALAPAPPQVLPQAPAPAPAPAMVSALAQAPAPV
PVLAPGPPQAVAPPAPKPTQAGEGTLSEALLQLQFDDEDLGALL
GNSTDPAVFTDLASVDNSEFQQLLNQGIPVAPHTTEPMLMEYPE
AITRLVTGAQRPPDPAPAPLGAPGLPNGLLSGDEDFSSIADMDFS
ALLGSGSGSRDSREGMFLPKPEAGSAISDVFEGREVCQPKRIRPF
HPPGSPWANRPLPASLAPTPTGPVHEPVGSLTPAPVPQPLDPAPA
VTPEASHLLEDPDEETSQAVKALREMADTVIPQKEEAAICGQMD
LSHPPPRGHLDELTTTLESMTEDLNLDSPLTPELNEILDTFLNDEC
LLHAMHISTGLSIFDTSLF 4x MoonTag
SEQ ID NO: 29
GGGSGGAHIVMVDNYKPIVGGSGGAHIVMVDNYKPIVGGSGGA
HIVMVDNYKPIVGGSGGGGSGGAHIVMVDNYKPIV VTR3 SEQUENCE
SEQ ID NO: 30
GSGRADALDDFDLDMLGSDALDDFDLDMLGSDALDDFDLDMLGSDA
LDDFDLDMLINSRLVTGAQRPPDPAPAPLGAPGLPNGLLSGDEDFS
SIADMDFSALLSQISSGGGSRLVTGAQRPPDPAPAPLGAPGLPNGL
LSGDEDFSSIADMDFSALLSQISSGSGSQPLDPAPAVTPEASHLLE
DPDEETSQAVKALREMADTVIPQKEEAAICGQMDLSHPPPRGHLDE
LTTTLESMTEDLNLDSPLTPELNEILDTFLNDECLLHAMHISTGLS
IFDTSLFTS gRNA-ccr5-1

SEQ ID NO: 31

GCTGTGTTTGCGTCTCTCCC gRNA-ccr5-2

SEQ ID NO: 32

GGGGTGGTGACAAGTGTGAT

Mini-saCas9-4:VPR

SEQ ID NO: 33

MPKKKRKVGGGSPGGGGSKRNYILGLDIGITSVGYGIIDYETRDVI
DAGVRLFKEANVENNEGRRSKRGARRLKRRRRHRIQRVKKLLFDYN
LLTDHSELSGINPYEARVKGLSQKLSEEEFSAALLHLAKRRGVHNV
NEVEEDTGNELSTKEQISRNSKALEEKYVAELQLERLKKDGEVRGS
INRFKTSDYVKEAKQLLKVQKAYHQLDQSFIDTYIDLLETRRTYYE
GPGEGSPFGWKDIKEWYEMLMGHCTYFPEELRSVKYAYNADLYNAL
NDLNNLVITRDENEKLEYYEKFQIIENVFKQKKKPTLKQIAKEILV
NEEDIKGYRVTSTGKPEFTNLKVYHDIKDITARKEIIENAELLDQI
AKILTIYQSSEDIQEELTNLNSELTQEEIEQISNLKGYTGTHNLSL
KAINLILDELWHTNDNQIAIFNRLKLVPKKVDLSQQKEIPTTLVDD
FILSPVVKRSFIQSIKVINAIIKKYGLPNDIIIELGSKRYATRGLM
NLLRSYFRVNNLDVKVKSINGGFTSFLRRKWFKKERNKGYKHHAE
DALIIANADFIFKEWKKLDKAKKVMENQMFEEKQAESMPEIETEQE
YKEIFITPHQIKHEKDFKDYKYSHRVDKKPNRKLINDTLYSTRKDD
KGNTLIVNNLNGLYDKDNDKLKKLINKSPEKLLMYHHDPQTYQKLK
LIMEQYGDEKNPLYKYYEETGNYLTKYSKKDNGPVIKKIKYYGNKL
NAHLDITDDYPNSRNKVVKLSLKPYRFDVYLDNGVYKFVTVKNLDV
IKKENYYEVNSKCYEEAKKLKKISNQAEFIASFYKNDLIKINGELY
RVIGVNNDLLNRIEVNMIDITYREYLENMNDKRPPHIIKTIASKTQ
SIKKYSTDILGNLYEVKSKKHPQIIKKGTSRADPKKKRKVEASGSG
RADALDDFDLDMLGSDALDDFDLDMLGSDALDDFDLDMLGSDALDD
FDLDMLINSRSQYLPDTDDRHRIEEKRKRTYETFKSIMKKSPFSGP
TDPRPPPRRIAVPSRSSASVPKPAPQPYPFTSSLSTINYDEFPTMV
FPSGQISQASALAPAPPQVLPQAPAPAPAPAMVSALAQAPAPVPVL
APGPPQAVAPPAPKPTQAGEGTLSEALLQLQFDDEDLGALLGNSTD
PAVFTDLASVDNSEFQQLLNQGIPVAPHTTEPMLMEYPEAITRLVT
GAQRPPDPAPAPLGAPGLPNGLLSGDEDFSSIADMDFSALLGSGSG
SRDSREGMFLPKPEAGSAISDVFEGREVCQPKRIRPFHPPGSPWAN
RPLPASLAPTPTGPVHEPVGSLTPAPVPQPLDPAPAVTPEASHLLE
DPDEETSQAVKALREMADTVIPQKEEAAICGQMDLSHPPPRGHLDE
LTTTLESMTEDLNLDSPLTPELNEILDTFLNDECLLHAMHISTGLS
IFDTSLF

Mini-saCas9-5:VPR

SEQ ID NO: 34

MPKKKRKVGGGSPGGGGSKRNYILGLDIGITSVGYGIIDYETRDVI
DAGVRLFKEANVENNEGRRSKRGARRLKRRRRHRIQRVKKLLFDYN
LLTDHSELSGINPYEARVKGLSQKLSEEEFSAALLHLAKRRGVHNV
NEVEEDTGNELSTKEQISRNSKALEEKYVAELQLERLKKDGEVRGS
INRFKTSDYVKEAKQLLKVQKAYHQLDQSFIDTYIDLLETRRTYYE
GPGEGSPFGWKDIKEWYEMLMGHCTKKVDLSQQKEIPTTLVDDFIL
SPVVKRSFIQSIKVINAIIKKYGLPNDIIIELAREKNSKDAQKMIN
EMQKRNRQTNERIEEIIRTTGKENAKYLIEKIKLHDMQEGKCLYSL
EAIPLEDLLNNPFNYEVDHIIPRSVSFDNSFNNKVLVKQEENSKKG
NRTPFQYLSSSDSKISYETFKKHILNLAKGKGRISKTKKEYLLEER
DINRFSVQKDFINRNLVDTRYATRGLMNLLRSYFRVNNLDVKVKSI
NGGFTSFLRRKWFKKERNKGYKHHAEDALIIANKADFIFKEWKKLD
KAKKVMENQMFEEKQAESMPEIETEQEYKEIFITPHQIKHIKDFKD
YKYSHRVDKKPNRKLINDTLYSTRKDDKGNTLIVNNLNGLYDKDND
KLKKLINKSPEKLLMYHHDPQTYQKLKLIMEQYGDEKNPLYKYYEE
TGNYLTKYSKKDNGPVIKKIKYYGNKLNAHLDITDDYPNSRNKVVK
LSLKPYRFDVYLDNGVYKFVTVKNLDVIKKENYYEVNSKCYEEAKK
LKKISNQAEFIASFYKNDLIKINGELYRVIGVNNDLLNRIEVNMID
ITYREYLENMNDKRPPHIIKTIASKTQSIKKYSTDILGNLYEVKSK
KHPQIIKKGTSRADPKKKRKVEASGSGRADALDDFDLDMLGSDALD
DFDLDMLGSDALDDFDLDMLGSDALDDFDLDMLINSRSQYLPDTDD
RHRIEEKRKRTYETFKSIMKKSPFSGPTDPRPPPRRIAVPSRSSAS
VPKPAPQPYPFTSSLSTINYDEFPTMVFPSGQISQASALAPAPPQV
LPQAPAPAPAPAMVSALAQAPAPVPVLAPGPPQAVAPPAPKPTQAG
EGTLSEALLQLQFDDEDLGALLGNSTDPAVFTDLASVDNSEFQQLL
NQGIPVAPHTTEPMLMEYPEAITRLVTGAQRPPDPAPAPLGAPGLP
NGLLSGDEDFSSIADMDFSALLGSGSGSRDSREGMFLPKPEAGSAI
SDVFEGREVCQPKRIRPFHPPGSPWANRPLPASLAPTPTGPVHEPV
GSLTPAPVPQPLDPAPAVTPEASHLLEDPDEETSQAVKALREMADT
VIPQKEEAAICGQMDLSHPPPRGHLDELTTTLESMTEDLNLDSPLT
PELNEILDTFLNDECLLHAMHISTGLSIFDTSLF altered PAM

SEQ ID NO: 36

NNNRRT

GS-linker

SEQ ID NO: 37

GGGGSGGGG

R-linker

SEQ ID NO: 38

KRRRRHR

GSK Linker

SEQ ID NO: 39

GSK

We claim:

1. A non-naturally occurring Cas9 protein comprising a *Staphylococcus aureus* (SaCas9) protein wherein the HNH region has been deleted in full and replaced with a protein sequence consisting of "GSK".

2. The non-naturally occurring Cas9 protein of claim 1 comprising the amino acid sequence of SEQ ID NO: 33.

* * * * *

SEQUENCE LISTING

<160> NUMBER OF SEQ ID NOS: 37

<210> SEQ ID NO 1
<211> LENGTH: 20
<212> TYPE: DNA
<213> ORGANISM: Artificial Sequence
<220> FEATURE:
<223> OTHER INFORMATION: Synthetic construct created by rational design

<400> SEQUENCE: 1
tacgttctct atcactgata                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic construct created by rational design

<400> SEQUENCE: 2
tacgttctct atcactgata                                               20

<210> SEQ ID NO 3
<211> LENGTH: 23
<212> TYPE: DNA
<213> ORGANISM: Artificial Sequence
<220> FEATURE:
<223> OTHER INFORMATION: Synthetic construct created by rational design

<400> SEQUENCE: 3
ctccctatca gtgatagaga acg                                           23

<210> SEQ ID NO 4
<211> LENGTH: 18
<212> TYPE: DNA
<213> ORGANISM: Artificial Sequence
<220> FEATURE:
<223> OTHER INFORMATION: Synthetic construct created by rational design

<400> SEQUENCE: 4
cgttctctat cactgata                                                 18

<210> SEQ ID NO 5
<211> LENGTH: 18
<212> TYPE: DNA
<213> ORGANISM: Artificial Sequence
<220> FEATURE:
<223> OTHER INFORMATION: Synthetic construct created by rational design

<400> SEQUENCE: 5
actagaaatt caccgagc                                                 18

<210> SEQ ID NO 6
<211> LENGTH: 21
<212> TYPE: DNA
<213> ORGANISM: Artificial Sequence
<220> FEATURE:
<223> OTHER INFORMATION: Synthetic construct created by rational design

<400> SEQUENCE: 6
ctcactcaac agtgatagag a                                             21

<210> SEQ ID NO 7
<211> LENGTH: 21
<212> TYPE: DNA
<213> ORGANISM: Artificial Sequence

```
<220> FEATURE:
<223> OTHER INFORMATION: Synthetic construct created by rational design

<400> SEQUENCE: 7
ttgctcactc aacagtgata g                                              21

<210> SEQ ID NO 8
<211> LENGTH: 1913
<212> TYPE: PRT
<213> ORGANISM: Artificial Sequence
<220> FEATURE:
<223> OTHER INFORMATION: Synthetic construct created by rational design

<400> SEQUENCE: 8
```

Met Pro Lys Lys Arg Lys Val Gly Gly Ser Pro Gly Met Asp
1               5                   10                  15

Lys Lys Tyr Ser Ile Gly Leu Ala Ile Gly Thr Asn Ser Val Gly Trp
            20                  25                  30

Ala Val Ile Thr Asp Glu Tyr Lys Val Pro Ser Lys Lys Phe Lys Val
        35                  40                  45

Leu Gly Asn Thr Asp Arg His Ser Ile Lys Lys Asn Leu Ile Gly Ala
    50                  55                  60

Leu Leu Phe Asp Ser Gly Glu Thr Ala Glu Ala Thr Arg Leu Lys Arg
65                  70                  75                  80

Thr Ala Arg Arg Arg Tyr Thr Arg Arg Lys Asn Arg Ile Cys Tyr Leu
                85                  90                  95

Gln Glu Ile Phe Ser Asn Glu Met Ala Lys Val Asp Asp Ser Phe Phe
            100                 105                 110

His Arg Leu Glu Glu Ser Phe Leu Val Glu Glu Asp Lys Lys His Glu
        115                 120                 125

Arg His Pro Ile Phe Gly Asn Ile Val Asp Glu Val Ala Tyr His Glu
    130                 135                 140

Lys Tyr Pro Thr Ile Tyr His Leu Arg Lys Lys Leu Val Asp Ser Thr
145                 150                 155                 160

Asp Lys Ala Asp Leu Arg Leu Ile Tyr Leu Ala Leu Ala His Met Ile
                165                 170                 175

Lys Phe Arg Gly His Phe Leu Ile Glu Gly Asp Leu Asn Pro Asp Asn
            180                 185                 190

Ser Asp Val Asp Lys Leu Phe Ile Gln Leu Val Gln Thr Tyr Asn Gln
        195                 200                 205

Leu Phe Glu Glu Asn Pro Ile Asn Ala Ser Gly Val Asp Ala Lys Ala
    210                 215                 220

Ile Leu Ser Ala Arg Leu Ser Lys Ser Arg Arg Leu Glu Asn Leu Ile
225                 230                 235                 240

Ala Gln Leu Pro Gly Glu Lys Lys Asn Gly Leu Phe Gly Asn Leu Ile
                245                 250                 255

Ala Leu Ser Leu Gly Leu Thr Pro Asn Phe Lys Ser Asn Phe Asp Leu
            260                 265                 270

Ala Glu Asp Ala Lys Leu Gln Leu Ser Lys Asp Thr Tyr Asp Asp Asp
        275                 280                 285

Leu Asp Asn Leu Leu Ala Gln Ile Gly Asp Gln Tyr Ala Asp Leu Phe
    290                 295                 300

Leu Ala Ala Lys Asn Leu Ser Asp Ala Ile Leu Leu Ser Asp Ile Leu
305                 310                 315                 320

Arg Val Asn Thr Glu Ile Thr Lys Ala Pro Leu Ser Ala Ser Met Ile
                325                 330                 335

```
Lys Arg Tyr Asp Glu His His Gln Asp Leu Thr Leu Leu Lys Ala Leu
            340                 345                 350

Val Arg Gln Gln Leu Pro Glu Lys Tyr Lys Glu Ile Phe Phe Asp Gln
            355                 360                 365

Ser Lys Asn Gly Tyr Ala Gly Tyr Ile Asp Gly Gly Ala Ser Gln Glu
            370                 375                 380

Glu Phe Tyr Lys Phe Ile Lys Pro Ile Leu Glu Lys Met Asp Gly Thr
385                 390                 395                 400

Glu Glu Leu Leu Val Lys Leu Asn Arg Glu Asp Leu Leu Arg Lys Gln
                    405                 410                 415

Arg Thr Phe Asp Asn Gly Ser Ile Pro His Gln Ile His Leu Gly Glu
            420                 425                 430

Leu His Ala Ile Leu Arg Arg Gln Glu Asp Phe Tyr Pro Phe Leu Lys
            435                 440                 445

Asp Asn Arg Glu Lys Ile Glu Lys Ile Leu Thr Phe Arg Ile Pro Tyr
            450                 455                 460

Tyr Val Gly Pro Leu Ala Arg Gly Asn Ser Arg Phe Ala Trp Met Thr
465                 470                 475                 480

Arg Lys Ser Glu Glu Thr Ile Thr Pro Trp Asn Phe Glu Glu Val Val
                    485                 490                 495

Asp Lys Gly Ala Ser Ala Gln Ser Phe Ile Glu Arg Met Thr Asn Phe
            500                 505                 510

Asp Lys Asn Leu Pro Asn Glu Lys Val Leu Pro Lys His Ser Leu Leu
            515                 520                 525

Tyr Glu Tyr Phe Thr Val Tyr Asn Glu Leu Thr Lys Val Lys Tyr Val
            530                 535                 540

Thr Glu Gly Met Arg Lys Pro Ala Phe Leu Ser Gly Glu Gln Lys Lys
545                 550                 555                 560

Ala Ile Val Asp Leu Leu Phe Lys Thr Asn Arg Lys Val Thr Val Lys
                    565                 570                 575

Gln Leu Lys Glu Asp Tyr Phe Lys Lys Ile Glu Cys Phe Asp Ser Val
            580                 585                 590

Glu Ile Ser Gly Val Glu Asp Arg Phe Asn Ala Ser Leu Gly Thr Tyr
            595                 600                 605

His Asp Leu Leu Lys Ile Ile Lys Asp Lys Asp Phe Leu Asp Asn Glu
            610                 615                 620

Glu Asn Glu Asp Ile Leu Glu Asp Ile Val Leu Thr Leu Thr Leu Phe
625                 630                 635                 640

Glu Asp Arg Glu Met Ile Glu Glu Arg Leu Lys Thr Tyr Ala His Leu
                    645                 650                 655

Phe Asp Asp Lys Val Met Lys Gln Leu Lys Arg Arg Arg Tyr Thr Gly
            660                 665                 670

Trp Gly Arg Leu Ser Arg Lys Leu Ile Asn Gly Ile Arg Asp Lys Gln
            675                 680                 685

Ser Gly Lys Thr Ile Leu Asp Phe Leu Lys Ser Asp Gly Phe Ala Asn
            690                 695                 700

Arg Asn Phe Met Gln Leu Ile His Asp Asp Ser Leu Thr Phe Lys Glu
705                 710                 715                 720

Asp Ile Gln Lys Ala Gln Val Ser Gly Gln Gly Asp Ser Leu His Glu
                    725                 730                 735

His Ile Ala Asn Leu Ala Gly Ser Pro Ala Ile Lys Lys Gly Ile Leu
            740                 745                 750
```

-continued

```
Gln Thr Val Lys Val Asp Glu Leu Val Lys Val Met Gly Arg His
        755                 760                 765
Lys Pro Glu Asn Ile Val Ile Glu Met Ala Arg Glu Asn Gln Thr Thr
770                 775                 780
Gln Lys Gly Gln Lys Asn Ser Arg Glu Arg Met Lys Arg Ile Glu Glu
785                 790                 795                 800
Gly Ile Lys Glu Leu Gly Ser Gln Ile Leu Lys Glu His Pro Val Glu
                805                 810                 815
Asn Thr Gln Leu Gln Asn Glu Lys Leu Tyr Leu Tyr Tyr Leu Gln Asn
            820                 825                 830
Gly Arg Asp Met Tyr Val Asp Gln Glu Leu Asp Ile Asn Arg Leu Ser
            835                 840                 845
Asp Tyr Asp Val Asp Ala Ile Val Pro Gln Ser Phe Leu Lys Asp Asp
        850                 855                 860
Ser Ile Asp Asn Lys Val Leu Thr Arg Ser Asp Lys Asn Arg Gly Lys
865                 870                 875                 880
Ser Asp Asn Val Pro Ser Glu Glu Val Val Lys Met Lys Asn Tyr
                885                 890                 895
Trp Arg Gln Leu Leu Asn Ala Lys Leu Ile Thr Gln Arg Lys Phe Asp
                900                 905                 910
Asn Leu Thr Lys Ala Glu Arg Gly Gly Leu Ser Glu Leu Asp Lys Ala
            915                 920                 925
Gly Phe Ile Lys Arg Gln Leu Val Glu Thr Arg Gln Ile Thr Lys His
        930                 935                 940
Val Ala Gln Ile Leu Asp Ser Arg Met Asn Thr Lys Tyr Asp Glu Asn
945                 950                 955                 960
Asp Lys Leu Ile Arg Glu Val Lys Val Ile Thr Leu Lys Ser Lys Leu
                965                 970                 975
Val Ser Asp Phe Arg Lys Asp Phe Gln Phe Tyr Lys Val Arg Glu Ile
            980                 985                 990
Asn Asn Tyr His His Ala His Asp Ala Tyr Leu Asn Ala Val Val Gly
            995                 1000                1005
Thr Ala Leu Ile Lys Lys Tyr Pro Lys Leu Glu Ser Glu Phe Val
        1010                1015                1020
Tyr Gly Asp Tyr Lys Val Tyr Asp Val Arg Lys Met Ile Ala Lys
        1025                1030                1035
Ser Glu Gln Glu Ile Gly Lys Ala Thr Ala Lys Tyr Phe Phe Tyr
        1040                1045                1050
Ser Asn Ile Met Asn Phe Phe Lys Thr Glu Ile Thr Leu Ala Asn
        1055                1060                1065
Gly Glu Ile Arg Lys Arg Pro Leu Ile Glu Thr Asn Gly Glu Thr
        1070                1075                1080
Gly Glu Ile Val Trp Asp Lys Gly Arg Asp Phe Ala Thr Val Arg
        1085                1090                1095
Lys Val Leu Ser Met Pro Gln Val Asn Ile Val Lys Lys Thr Glu
        1100                1105                1110
Val Gln Thr Gly Gly Phe Ser Lys Glu Ser Ile Leu Pro Lys Arg
        1115                1120                1125
Asn Ser Asp Lys Leu Ile Ala Arg Lys Lys Asp Trp Asp Pro Lys
        1130                1135                1140
Lys Tyr Gly Gly Phe Asp Ser Pro Thr Val Ala Tyr Ser Val Leu
        1145                1150                1155
Val Val Ala Lys Val Glu Lys Gly Lys Ser Lys Lys Leu Lys Ser
```

-continued

```
                    1160                1165                1170

Val Lys Glu Leu Leu Gly Ile Thr Ile Met Glu Arg Ser Ser Phe
    1175                1180                1185

Glu Lys Asn Pro Ile Asp Phe Leu Glu Ala Lys Gly Tyr Lys Glu
    1190                1195                1200

Val Lys Lys Asp Leu Ile Ile Lys Leu Pro Lys Tyr Ser Leu Phe
    1205                1210                1215

Glu Leu Glu Asn Gly Arg Lys Arg Met Leu Ala Ser Ala Gly Glu
    1220                1225                1230

Leu Gln Lys Gly Asn Glu Leu Ala Leu Pro Ser Lys Tyr Val Asn
    1235                1240                1245

Phe Leu Tyr Leu Ala Ser His Tyr Glu Lys Leu Lys Gly Ser Pro
    1250                1255                1260

Glu Asp Asn Glu Gln Lys Gln Leu Phe Val Glu Gln His Lys His
    1265                1270                1275

Tyr Leu Asp Glu Ile Ile Glu Gln Ile Ser Glu Phe Ser Lys Arg
    1280                1285                1290

Val Ile Leu Ala Asp Ala Asn Leu Asp Lys Val Leu Ser Ala Tyr
    1295                1300                1305

Asn Lys His Arg Asp Lys Pro Ile Arg Glu Gln Ala Glu Asn Ile
    1310                1315                1320

Ile His Leu Phe Thr Leu Thr Asn Leu Gly Ala Pro Ala Ala Phe
    1325                1330                1335

Lys Tyr Phe Asp Thr Thr Ile Asp Arg Lys Arg Tyr Thr Ser Thr
    1340                1345                1350

Lys Glu Val Leu Asp Ala Thr Leu Ile His Gln Ser Ile Thr Gly
    1355                1360                1365

Leu Tyr Glu Thr Arg Ile Asp Leu Ser Gln Leu Gly Gly Asp Thr
    1370                1375                1380

Ser Arg Ala Asp Pro Lys Lys Lys Arg Lys Val Glu Ala Ser Gly
    1385                1390                1395

Ser Gly Arg Ala Asp Ala Leu Asp Asp Phe Asp Leu Asp Met Leu
    1400                1405                1410

Gly Ser Asp Ala Leu Asp Asp Phe Asp Leu Asp Met Leu Gly Ser
    1415                1420                1425

Asp Ala Leu Asp Asp Phe Asp Leu Asp Met Leu Gly Ser Asp Ala
    1430                1435                1440

Leu Asp Asp Phe Asp Leu Asp Met Leu Ile Asn Ser Arg Ser Gln
    1445                1450                1455

Tyr Leu Pro Asp Thr Asp Asp Arg His Arg Ile Glu Glu Lys Arg
    1460                1465                1470

Lys Arg Thr Tyr Glu Thr Phe Lys Ser Ile Met Lys Lys Ser Pro
    1475                1480                1485

Phe Ser Gly Pro Thr Asp Pro Arg Pro Pro Arg Arg Ile Ala
    1490                1495                1500

Val Pro Ser Arg Ser Ser Ala Ser Val Pro Lys Pro Ala Pro Gln
    1505                1510                1515

Pro Tyr Pro Phe Thr Ser Ser Leu Ser Thr Ile Asn Tyr Asp Glu
    1520                1525                1530

Phe Pro Thr Met Val Phe Pro Ser Gly Gln Ile Ser Gln Ala Ser
    1535                1540                1545

Ala Leu Ala Pro Ala Pro Pro Gln Val Leu Pro Gln Ala Pro Ala
    1550                1555                1560
```

```
Pro Ala Pro Ala Pro Ala Met Val Ser Ala Leu Ala Gln Ala Pro
    1565                1570                1575
Ala Pro Val Pro Val Leu Ala Pro Gly Pro Pro Gln Ala Val Ala
1580                1585                1590
Pro Pro Ala Pro Lys Pro Thr Gln Ala Gly Glu Gly Thr Leu Ser
1595                1600                1605
Glu Ala Leu Leu Gln Leu Gln Phe Asp Asp Glu Asp Leu Gly Ala
1610                1615                1620
Leu Leu Gly Asn Ser Thr Asp Pro Ala Val Phe Thr Asp Leu Ala
1625                1630                1635
Ser Val Asp Asn Ser Glu Phe Gln Gln Leu Leu Asn Gln Gly Ile
1640                1645                1650
Pro Val Ala Pro His Thr Thr Glu Pro Met Leu Met Glu Tyr Pro
1655                1660                1665
Glu Ala Ile Thr Arg Leu Val Thr Gly Ala Gln Arg Pro Pro Asp
1670                1675                1680
Pro Ala Pro Ala Pro Leu Gly Ala Pro Gly Leu Pro Asn Gly Leu
1685                1690                1695
Leu Ser Gly Asp Glu Asp Phe Ser Ser Ile Ala Asp Met Asp Phe
1700                1705                1710
Ser Ala Leu Leu Gly Ser Gly Ser Gly Ser Arg Asp Ser Arg Glu
1715                1720                1725
Gly Met Phe Leu Pro Lys Pro Glu Ala Gly Ser Ala Ile Ser Asp
1730                1735                1740
Val Phe Glu Gly Arg Glu Val Cys Gln Pro Lys Arg Ile Arg Pro
1745                1750                1755
Phe His Pro Pro Gly Ser Pro Trp Ala Asn Arg Pro Leu Pro Ala
1760                1765                1770
Ser Leu Ala Pro Thr Pro Thr Gly Pro Val His Glu Pro Val Gly
1775                1780                1785
Ser Leu Thr Pro Ala Pro Val Pro Gln Pro Leu Asp Pro Ala Pro
1790                1795                1800
Ala Val Thr Pro Glu Ala Ser His Leu Leu Glu Asp Pro Asp Glu
1805                1810                1815
Glu Thr Ser Gln Ala Val Lys Ala Leu Arg Glu Met Ala Asp Thr
1820                1825                1830
Val Ile Pro Gln Lys Glu Glu Ala Ala Ile Cys Gly Gln Met Asp
1835                1840                1845
Leu Ser His Pro Pro Pro Arg Gly His Leu Asp Glu Leu Thr Thr
1850                1855                1860
Thr Leu Glu Ser Met Thr Glu Asp Leu Asn Leu Asp Ser Pro Leu
1865                1870                1875
Thr Pro Glu Leu Asn Glu Ile Leu Asp Thr Phe Leu Asn Asp Glu
1880                1885                1890
Cys Leu Leu His Ala Met His Ile Ser Thr Gly Leu Ser Ile Phe
1895                1900                1905
Asp Thr Ser Leu Phe
    1910

<210> SEQ ID NO 9
<211> LENGTH: 1703
<212> TYPE: PRT
<213> ORGANISM: Artificial Sequence
<220> FEATURE:
```

<223> OTHER INFORMATION: Synthetic construct created by rational design

<400> SEQUENCE: 9

```
Met Pro Lys Lys Lys Arg Lys Val Gly Gly Ser Pro Gly Met Asp
1               5                   10                  15

Lys Lys Tyr Ser Ile Gly Leu Ala Ile Gly Thr Asn Ser Val Gly Trp
            20                  25                  30

Ala Val Ile Thr Asp Glu Tyr Lys Val Pro Ser Lys Lys Phe Lys Val
            35                  40                  45

Leu Gly Asn Thr Asp Arg His Ser Ile Lys Lys Asn Leu Ile Gly Ala
50              55                  60

Leu Leu Phe Asp Ser Gly Glu Thr Ala Glu Ala Thr Arg Leu Lys Arg
65              70                  75                  80

Thr Ala Arg Arg Arg Tyr Thr Arg Arg Lys Asn Arg Ile Cys Tyr Leu
                85                  90                  95

Gln Glu Ile Phe Ser Asn Glu Met Ala Lys Val Asp Asp Ser Phe Phe
            100                 105                 110

His Arg Leu Glu Glu Ser Phe Leu Val Glu Glu Asp Lys Lys His Glu
            115                 120                 125

Arg His Pro Ile Phe Gly Asn Ile Val Asp Glu Val Ala Tyr His Glu
130                 135                 140

Lys Tyr Pro Thr Ile Tyr His Leu Arg Lys Lys Leu Val Asp Ser Thr
145                 150                 155                 160

Asp Lys Ala Asp Leu Arg Leu Ile Tyr Leu Ala Leu Ala His Met Ile
            165                 170                 175

Lys Phe Arg Gly His Phe Leu Ile Glu Gly Asp Leu Asn Pro Asp Asn
            180                 185                 190

Ser Asp Val Asp Lys Leu Phe Ile Gln Leu Val Gln Thr Tyr Asn Gln
            195                 200                 205

Leu Phe Glu Glu Asn Pro Ile Asn Ala Ser Gly Val Asp Ala Lys Ala
210                 215                 220

Ile Leu Ser Ala Arg Leu Ser Lys Ser Arg Arg Leu Glu Asn Leu Ile
225                 230                 235                 240

Ala Gln Leu Pro Gly Glu Lys Lys Asn Gly Leu Phe Gly Asn Leu Ile
            245                 250                 255

Ala Leu Ser Leu Gly Leu Thr Pro Asn Phe Lys Ser Asn Phe Asp Leu
            260                 265                 270

Ala Glu Asp Ala Lys Leu Gln Leu Ser Lys Asp Thr Tyr Asp Asp Asp
            275                 280                 285

Leu Asp Asn Leu Leu Ala Gln Ile Gly Asp Gln Tyr Ala Asp Leu Phe
290                 295                 300

Leu Ala Ala Lys Asn Leu Ser Asp Ala Ile Leu Leu Ser Asp Ile Leu
305                 310                 315                 320

Arg Val Asn Thr Glu Ile Thr Lys Ala Pro Leu Ser Ala Ser Met Ile
            325                 330                 335

Lys Arg Tyr Asp Glu His His Gln Asp Leu Thr Leu Leu Lys Ala Leu
            340                 345                 350

Val Arg Gln Gln Leu Pro Glu Lys Tyr Lys Glu Ile Phe Phe Asp Gln
            355                 360                 365

Ser Lys Asn Gly Tyr Ala Gly Tyr Ile Asp Gly Gly Ala Ser Gln Glu
            370                 375                 380

Glu Phe Tyr Lys Phe Ile Lys Pro Ile Leu Glu Lys Met Asp Gly Thr
385                 390                 395                 400
```

-continued

Glu Glu Leu Leu Val Lys Leu Asn Arg Glu Asp Leu Leu Arg Lys Gln
                405                 410                 415

Arg Thr Phe Asp Asn Gly Ser Ile Pro His Gln Ile His Leu Gly Glu
            420                 425                 430

Leu His Ala Ile Leu Arg Arg Gln Glu Asp Phe Tyr Pro Phe Leu Lys
        435                 440                 445

Asp Asn Arg Glu Lys Ile Glu Lys Ile Leu Thr Phe Arg Ile Pro Tyr
    450                 455                 460

Tyr Val Gly Pro Leu Ala Arg Gly Asn Ser Arg Phe Ala Trp Met Thr
465                 470                 475                 480

Arg Lys Ser Glu Glu Thr Ile Thr Pro Trp Asn Phe Glu Glu Val Val
            485                 490                 495

Asp Lys Gly Ala Ser Ala Gln Ser Phe Ile Glu Arg Met Thr Asn Phe
        500                 505                 510

Asp Lys Ala Gln Val Ser Gly Gln Gly Asp Ser Leu His Glu His Ile
    515                 520                 525

Ala Asn Leu Ala Gly Ser Pro Ala Ile Lys Lys Gly Ile Leu Gln Thr
530                 535                 540

Val Lys Val Val Asp Glu Leu Val Lys Val Met Gly Arg His Lys Pro
545                 550                 555                 560

Glu Asn Ile Val Ile Glu Met Ala Arg Glu Asn Gln Thr Thr Gln Lys
            565                 570                 575

Gly Gln Lys Asn Ser Arg Glu Arg Met Lys Arg Ile Glu Glu Gly Ile
        580                 585                 590

Lys Glu Leu Gly Ser Gln Ile Leu Lys Glu His Pro Val Glu Asn Thr
    595                 600                 605

Gln Leu Gln Asn Glu Lys Leu Tyr Leu Tyr Tyr Leu Gln Asn Gly Arg
610                 615                 620

Asp Met Tyr Val Asp Gln Glu Leu Asp Ile Asn Arg Leu Ser Asp Tyr
625                 630                 635                 640

Asp Val Asp Ala Ile Val Pro Gln Ser Phe Leu Lys Asp Asp Ser Ile
            645                 650                 655

Asp Asn Lys Val Leu Thr Arg Ser Asp Lys Asn Arg Gly Lys Ser Asp
        660                 665                 670

Asn Val Pro Ser Glu Glu Val Val Lys Lys Met Lys Asn Tyr Trp Arg
    675                 680                 685

Gln Leu Leu Asn Ala Lys Leu Ile Thr Gln Arg Lys Phe Asp Asn Leu
690                 695                 700

Thr Lys Ala Glu Arg Gly Gly Leu Ser Glu Leu Asp Lys Ala Gly Phe
705                 710                 715                 720

Ile Lys Arg Gln Leu Val Glu Thr Arg Gln Ile Thr Lys His Val Ala
            725                 730                 735

Gln Ile Leu Asp Ser Arg Met Asn Thr Lys Tyr Asp Glu Asn Asp Lys
        740                 745                 750

Leu Ile Arg Glu Val Lys Val Ile Thr Leu Lys Ser Lys Leu Val Ser
    755                 760                 765

Asp Phe Arg Lys Asp Phe Gln Phe Tyr Lys Val Arg Glu Ile Asn Asn
770                 775                 780

Tyr His His Ala His Asp Ala Tyr Leu Asn Ala Val Val Gly Thr Ala
785                 790                 795                 800

Leu Ile Lys Lys Tyr Pro Lys Leu Glu Ser Glu Phe Val Tyr Gly Asp
            805                 810                 815

Tyr Lys Val Tyr Asp Val Arg Lys Met Ile Ala Lys Ser Glu Gln Glu

-continued

```
              820                 825                 830
Ile Gly Lys Ala Thr Ala Lys Tyr Phe Phe Tyr Ser Asn Ile Met Asn
              835                 840                 845
Phe Phe Lys Thr Glu Ile Thr Leu Ala Asn Gly Glu Ile Arg Lys Arg
              850                 855                 860
Pro Leu Ile Glu Thr Asn Gly Glu Thr Gly Glu Ile Val Trp Asp Lys
865                 870                 875                 880
Gly Arg Asp Phe Ala Thr Val Arg Lys Val Leu Ser Met Pro Gln Val
                  885                 890                 895
Asn Ile Val Lys Lys Thr Glu Val Gln Thr Gly Gly Phe Ser Lys Glu
                  900                 905                 910
Ser Ile Leu Pro Lys Arg Asn Ser Asp Lys Leu Ile Ala Arg Lys Lys
                  915                 920                 925
Asp Trp Asp Pro Lys Lys Tyr Gly Gly Phe Asp Ser Pro Thr Val Ala
              930                 935                 940
Tyr Ser Val Leu Val Val Ala Lys Val Glu Lys Gly Lys Ser Lys Lys
945                 950                 955                 960
Leu Lys Ser Val Lys Glu Leu Leu Gly Ile Thr Ile Met Glu Arg Ser
                  965                 970                 975
Ser Phe Glu Lys Asn Pro Ile Asp Phe Leu Glu Ala Lys Gly Tyr Lys
              980                 985                 990
Glu Val Lys Lys Asp Leu Ile Ile Lys Leu Pro Lys Tyr Ser Leu Phe
              995                1000                1005
Glu Leu Glu Asn Gly Arg Lys Arg Met Leu Ala Ser Ala Gly Glu
             1010                1015                1020
Leu Gln Lys Gly Asn Glu Leu Ala Leu Pro Ser Lys Tyr Val Asn
             1025                1030                1035
Phe Leu Tyr Leu Ala Ser His Tyr Glu Lys Leu Lys Gly Ser Pro
             1040                1045                1050
Glu Asp Asn Glu Gln Lys Gln Leu Phe Val Glu Gln His Lys His
             1055                1060                1065
Tyr Leu Asp Glu Ile Ile Glu Gln Ile Ser Glu Phe Ser Lys Arg
             1070                1075                1080
Val Ile Leu Ala Asp Ala Asn Leu Asp Lys Val Leu Ser Ala Tyr
             1085                1090                1095
Asn Lys His Arg Asp Lys Pro Ile Arg Glu Gln Ala Glu Asn Ile
             1100                1105                1110
Ile His Leu Phe Thr Leu Thr Asn Leu Gly Ala Pro Ala Ala Phe
             1115                1120                1125
Lys Tyr Phe Asp Thr Thr Ile Asp Arg Lys Arg Tyr Thr Ser Thr
             1130                1135                1140
Lys Glu Val Leu Asp Ala Thr Leu Ile His Gln Ser Ile Thr Gly
             1145                1150                1155
Leu Tyr Glu Thr Arg Ile Asp Leu Ser Gln Leu Gly Gly Asp Thr
             1160                1165                1170
Ser Arg Ala Asp Pro Lys Lys Lys Arg Lys Val Glu Ala Ser Gly
             1175                1180                1185
Ser Gly Arg Ala Asp Ala Leu Asp Asp Phe Asp Leu Asp Met Leu
             1190                1195                1200
Gly Ser Asp Ala Leu Asp Asp Phe Asp Leu Asp Met Leu Gly Ser
             1205                1210                1215
Asp Ala Leu Asp Asp Phe Asp Leu Asp Met Leu Gly Ser Asp Ala
             1220                1225                1230
```

```
Leu Asp Asp Phe Asp Leu Asp Met Leu Ile Asn Ser Arg Ser Gln
    1235            1240                1245

Tyr Leu Pro Asp Thr Asp Asp Arg His Arg Ile Glu Glu Lys Arg
    1250            1255                1260

Lys Arg Thr Tyr Glu Thr Phe Lys Ser Ile Met Lys Lys Ser Pro
    1265            1270                1275

Phe Ser Gly Pro Thr Asp Pro Arg Pro Pro Arg Arg Ile Ala
    1280            1285                1290

Val Pro Ser Arg Ser Ser Ala Ser Val Pro Lys Pro Ala Pro Gln
    1295            1300                1305

Pro Tyr Pro Phe Thr Ser Ser Leu Ser Thr Ile Asn Tyr Asp Glu
    1310            1315                1320

Phe Pro Thr Met Val Phe Pro Ser Gly Gln Ile Ser Gln Ala Ser
    1325            1330                1335

Ala Leu Ala Pro Ala Pro Pro Gln Val Leu Pro Gln Ala Pro Ala
    1340            1345                1350

Pro Ala Pro Ala Pro Ala Met Val Ser Ala Leu Ala Gln Ala Pro
    1355            1360                1365

Ala Pro Val Pro Val Leu Ala Pro Gly Pro Pro Gln Ala Val Ala
    1370            1375                1380

Pro Pro Ala Pro Lys Pro Thr Gln Ala Gly Glu Gly Thr Leu Ser
    1385            1390                1395

Glu Ala Leu Leu Gln Leu Gln Phe Asp Asp Glu Asp Leu Gly Ala
    1400            1405                1410

Leu Leu Gly Asn Ser Thr Asp Pro Ala Val Phe Thr Asp Leu Ala
    1415            1420                1425

Ser Val Asp Asn Ser Glu Phe Gln Gln Leu Leu Asn Gln Gly Ile
    1430            1435                1440

Pro Val Ala Pro His Thr Thr Glu Pro Met Leu Met Glu Tyr Pro
    1445            1450                1455

Glu Ala Ile Thr Arg Leu Val Thr Gly Ala Gln Arg Pro Pro Asp
    1460            1465                1470

Pro Ala Pro Ala Pro Leu Gly Ala Pro Gly Leu Pro Asn Gly Leu
    1475            1480                1485

Leu Ser Gly Asp Glu Asp Phe Ser Ser Ile Ala Asp Met Asp Phe
    1490            1495                1500

Ser Ala Leu Leu Gly Ser Gly Ser Gly Ser Arg Asp Ser Arg Glu
    1505            1510                1515

Gly Met Phe Leu Pro Lys Pro Glu Ala Gly Ser Ala Ile Ser Asp
    1520            1525                1530

Val Phe Glu Gly Arg Glu Val Cys Gln Pro Lys Arg Ile Arg Pro
    1535            1540                1545

Phe His Pro Pro Gly Ser Pro Trp Ala Asn Arg Pro Leu Pro Ala
    1550            1555                1560

Ser Leu Ala Pro Thr Pro Thr Gly Pro Val His Glu Pro Val Gly
    1565            1570                1575

Ser Leu Thr Pro Ala Pro Val Pro Gln Pro Leu Asp Pro Ala Pro
    1580            1585                1590

Ala Val Thr Pro Glu Ala Ser His Leu Leu Glu Asp Pro Asp Glu
    1595            1600                1605

Glu Thr Ser Gln Ala Val Lys Ala Leu Arg Glu Met Ala Asp Thr
    1610            1615                1620
```

```
Val Ile Pro Gln Lys Glu Ala Ala Ile Cys Gly Gln Met Asp
    1625                1630                1635

Leu Ser His Pro Pro Pro Arg Gly His Leu Asp Glu Leu Thr Thr
    1640                1645                1650

Thr Leu Glu Ser Met Thr Glu Asp Leu Asn Leu Asp Ser Pro Leu
    1655                1660                1665

Thr Pro Glu Leu Asn Glu Ile Leu Asp Thr Phe Leu Asn Asp Glu
    1670                1675                1680

Cys Leu Leu His Ala Met His Ile Ser Thr Gly Leu Ser Ile Phe
    1685                1690                1695

Asp Thr Ser Leu Phe
    1700

<210> SEQ ID NO 10
<211> LENGTH: 1798
<212> TYPE: PRT
<213> ORGANISM: Artificial Sequence
<220> FEATURE:
<223> OTHER INFORMATION: Synthetic construct created by rational design

<400> SEQUENCE: 10

Met Pro Lys Lys Arg Lys Val Gly Gly Ser Pro Gly Met Asp
1               5                   10                  15

Lys Lys Tyr Ser Ile Gly Leu Ala Ile Gly Thr Asn Ser Val Gly Trp
            20                  25                  30

Ala Val Ile Thr Asp Glu Tyr Lys Val Pro Ser Lys Lys Phe Lys Val
        35                  40                  45

Leu Gly Asn Thr Asp Arg His Ser Ile Lys Lys Asn Leu Ile Gly Ala
50                  55                  60

Leu Leu Phe Asp Ser Gly Glu Thr Ala Glu Ala Thr Arg Leu Lys Arg
65                  70                  75                  80

Thr Ala Arg Arg Arg Tyr Thr Arg Arg Lys Asn Arg Ile Cys Tyr Leu
                85                  90                  95

Gln Glu Ile Phe Ser Asn Glu Met Ala Lys Val Asp Asp Ser Phe Phe
            100                 105                 110

His Arg Leu Glu Glu Ser Phe Leu Val Glu Glu Asp Lys Lys His Glu
        115                 120                 125

Arg His Pro Ile Phe Gly Asn Ile Val Asp Glu Val Ala Tyr His Glu
    130                 135                 140

Lys Tyr Pro Thr Ile Tyr His Leu Arg Lys Lys Leu Val Asp Ser Thr
145                 150                 155                 160

Asp Lys Ala Asp Leu Arg Leu Ile Tyr Leu Ala Leu Ala His Met Ile
                165                 170                 175

Lys Phe Arg Gly His Phe Leu Ile Glu Gly Asp Leu Asn Pro Asp Asn
            180                 185                 190

Ser Asp Val Asp Lys Leu Phe Ile Gln Leu Val Gln Thr Tyr Asn Gln
        195                 200                 205

Leu Phe Glu Glu Asn Pro Ile Asn Ala Ser Gly Val Asp Ala Lys Ala
    210                 215                 220

Ile Leu Ser Ala Arg Leu Ser Lys Ser Arg Arg Leu Glu Asn Leu Ile
225                 230                 235                 240

Ala Gln Leu Pro Gly Glu Lys Lys Asn Gly Leu Phe Gly Asn Leu Ile
                245                 250                 255

Ala Leu Ser Leu Gly Leu Thr Pro Asn Phe Lys Ser Asn Phe Asp Leu
            260                 265                 270
```

```
Ala Glu Asp Ala Lys Leu Gln Leu Ser Lys Asp Thr Tyr Asp Asp Asp
            275                 280                 285

Leu Asp Asn Leu Leu Ala Gln Ile Gly Asp Gln Tyr Ala Asp Leu Phe
    290                 295                 300

Leu Ala Ala Lys Asn Leu Ser Asp Ala Ile Leu Leu Ser Asp Ile Leu
305                 310                 315                 320

Arg Val Asn Thr Glu Ile Thr Lys Ala Pro Leu Ser Ala Ser Met Ile
                325                 330                 335

Lys Arg Tyr Asp Glu His His Gln Asp Leu Thr Leu Leu Lys Ala Leu
            340                 345                 350

Val Arg Gln Gln Leu Pro Glu Lys Tyr Lys Glu Ile Phe Phe Asp Gln
        355                 360                 365

Ser Lys Asn Gly Tyr Ala Gly Tyr Ile Asp Gly Gly Ala Ser Gln Glu
    370                 375                 380

Glu Phe Tyr Lys Phe Ile Lys Pro Ile Leu Glu Lys Met Asp Gly Thr
385                 390                 395                 400

Glu Glu Leu Leu Val Lys Leu Asn Arg Glu Asp Leu Leu Arg Lys Gln
                405                 410                 415

Arg Thr Phe Asp Asn Gly Ser Ile Pro His Gln Ile His Leu Gly Glu
            420                 425                 430

Leu His Ala Ile Leu Arg Arg Gln Glu Asp Phe Tyr Pro Phe Leu Lys
        435                 440                 445

Asp Asn Arg Glu Lys Ile Glu Lys Ile Leu Thr Phe Arg Ile Pro Tyr
    450                 455                 460

Tyr Val Gly Pro Leu Ala Arg Gly Asn Ser Arg Phe Ala Trp Met Thr
465                 470                 475                 480

Arg Lys Ser Glu Glu Thr Ile Thr Pro Trp Asn Phe Glu Glu Val Val
                485                 490                 495

Asp Lys Gly Ala Ser Ala Gln Ser Phe Ile Glu Arg Met Thr Asn Phe
            500                 505                 510

Asp Lys Asn Leu Pro Asn Glu Lys Val Leu Pro Lys His Ser Leu Leu
        515                 520                 525

Tyr Glu Tyr Phe Thr Val Tyr Asn Glu Leu Thr Lys Val Lys Tyr Val
    530                 535                 540

Thr Glu Gly Met Arg Lys Pro Ala Phe Leu Ser Gly Glu Gln Lys Lys
545                 550                 555                 560

Ala Ile Val Asp Leu Leu Phe Lys Thr Asn Arg Lys Val Thr Val Lys
                565                 570                 575

Gln Leu Lys Glu Asp Tyr Phe Lys Lys Ile Glu Cys Phe Asp Ser Val
            580                 585                 590

Glu Ile Ser Gly Val Glu Asp Arg Phe Asn Ala Ser Leu Gly Thr Tyr
        595                 600                 605

His Asp Leu Leu Lys Ile Ile Lys Asp Lys Asp Phe Leu Asp Asn Glu
    610                 615                 620

Glu Asn Glu Asp Ile Leu Glu Asp Ile Val Leu Thr Leu Thr Leu Phe
625                 630                 635                 640

Glu Asp Arg Glu Met Ile Glu Glu Arg Leu Lys Thr Tyr Ala His Leu
                645                 650                 655

Phe Asp Asp Lys Val Met Lys Gln Leu Lys Arg Arg Arg Tyr Thr Gly
            660                 665                 670

Trp Gly Arg Leu Ser Arg Lys Leu Ile Asn Gly Ile Arg Asp Lys Gln
        675                 680                 685

Ser Gly Lys Thr Ile Leu Asp Phe Leu Lys Ser Asp Gly Phe Ala Asn
```

```
                690             695             700
Arg Asn Phe Met Gln Leu Ile His Asp Asp Ser Leu Thr Phe Lys Glu
705                 710             715                 720

Asp Ile Gln Lys Ala Gln Val Ser Gly Gln Gly Asp Ser Leu His Glu
            725             730                 735

His Ile Ala Asn Leu Ala Gly Ser Pro Ala Ile Lys Lys Gly Ile Leu
                740             745             750

Gln Thr Val Lys Val Val Asp Glu Leu Val Lys Val Met Gly Arg His
            755             760             765

Lys Pro Glu Asn Ile Val Ile Glu Met Ala Arg Glu Asn Gln Thr Thr
        770             775             780

Gln Lys Gly Gln Lys Asn Ile Thr Gln Arg Lys Phe Asp Asn Leu Thr
785             790             795                 800

Lys Ala Glu Arg Gly Gly Leu Ser Glu Leu Asp Lys Ala Gly Phe Ile
                805             810             815

Lys Arg Gln Leu Val Glu Thr Arg Gln Ile Thr Lys His Val Ala Gln
            820             825             830

Ile Leu Asp Ser Arg Met Asn Thr Lys Tyr Asp Glu Asn Asp Lys Leu
            835             840             845

Ile Arg Glu Val Lys Val Ile Thr Leu Lys Ser Lys Leu Val Ser Asp
            850             855             860

Phe Arg Lys Asp Phe Gln Phe Tyr Lys Val Arg Glu Ile Asn Asn Tyr
865             870             875                 880

His His Ala His Asp Ala Tyr Leu Asn Ala Val Val Gly Thr Ala Leu
                885             890             895

Ile Lys Lys Tyr Pro Lys Leu Glu Ser Glu Phe Val Tyr Gly Asp Tyr
                900             905             910

Lys Val Tyr Asp Val Arg Lys Met Ile Ala Lys Ser Glu Gln Glu Ile
            915             920             925

Gly Lys Ala Thr Ala Lys Tyr Phe Phe Tyr Ser Asn Ile Met Asn Phe
        930             935             940

Phe Lys Thr Glu Ile Thr Leu Ala Asn Gly Glu Ile Arg Lys Arg Pro
945             950             955                 960

Leu Ile Glu Thr Asn Gly Glu Thr Gly Glu Ile Val Trp Asp Lys Gly
                965             970             975

Arg Asp Phe Ala Thr Val Arg Lys Val Leu Ser Met Pro Gln Val Asn
            980             985             990

Ile Val Lys Lys Thr Glu Val Gln Thr Gly Gly Phe Ser Lys Glu Ser
        995             1000            1005

Ile Leu Pro Lys Arg Asn Ser Asp Lys Leu Ile Ala Arg Lys Lys
        1010            1015            1020

Asp Trp Asp Pro Lys Lys Tyr Gly Gly Phe Asp Ser Pro Thr Val
        1025            1030            1035

Ala Tyr Ser Val Leu Val Val Ala Lys Val Glu Lys Gly Lys Ser
        1040            1045            1050

Lys Lys Leu Lys Ser Val Lys Glu Leu Leu Gly Ile Thr Ile Met
        1055            1060            1065

Glu Arg Ser Ser Phe Glu Lys Asn Pro Ile Asp Phe Leu Glu Ala
        1070            1075            1080

Lys Gly Tyr Lys Glu Val Lys Lys Asp Leu Ile Ile Lys Leu Pro
        1085            1090            1095

Lys Tyr Ser Leu Phe Glu Leu Glu Asn Gly Arg Lys Arg Met Leu
        1100            1105            1110
```

-continued

Ala Ser Ala Gly Glu Leu Gln Lys Gly Asn Glu Leu Ala Leu Pro
1115             1120                 1125

Ser Lys Tyr Val Asn Phe Leu Tyr Leu Ala Ser His Tyr Glu Lys
1130             1135                 1140

Leu Lys Gly Ser Pro Glu Asp Asn Glu Gln Lys Gln Leu Phe Val
1145             1150                 1155

Glu Gln His Lys His Tyr Leu Asp Glu Ile Ile Glu Gln Ile Ser
1160             1165                 1170

Glu Phe Ser Lys Arg Val Ile Leu Ala Asp Ala Asn Leu Asp Lys
1175             1180                 1185

Val Leu Ser Ala Tyr Asn Lys His Arg Asp Lys Pro Ile Arg Glu
1190             1195                 1200

Gln Ala Glu Asn Ile Ile His Leu Phe Thr Leu Thr Asn Leu Gly
1205             1210                 1215

Ala Pro Ala Ala Phe Lys Tyr Phe Asp Thr Thr Ile Asp Arg Lys
1220             1225                 1230

Arg Tyr Thr Ser Thr Lys Glu Val Leu Asp Ala Thr Leu Ile His
1235             1240                 1245

Gln Ser Ile Thr Gly Leu Tyr Glu Thr Arg Ile Asp Leu Ser Gln
1250             1255                 1260

Leu Gly Gly Asp Thr Ser Arg Ala Asp Pro Lys Lys Lys Arg Lys
1265             1270                 1275

Val Glu Ala Ser Gly Ser Gly Arg Ala Asp Ala Leu Asp Asp Phe
1280             1285                 1290

Asp Leu Asp Met Leu Gly Ser Asp Ala Leu Asp Asp Phe Asp Leu
1295             1300                 1305

Asp Met Leu Gly Ser Asp Ala Leu Asp Asp Phe Asp Leu Asp Met
1310             1315                 1320

Leu Gly Ser Asp Ala Leu Asp Phe Asp Leu Asp Met Leu Ile
1325             1330                 1335

Asn Ser Arg Ser Gln Tyr Leu Pro Asp Thr Asp Asp Arg His Arg
1340             1345                 1350

Ile Glu Glu Lys Arg Lys Arg Thr Tyr Glu Thr Phe Lys Ser Ile
1355             1360                 1365

Met Lys Lys Ser Pro Phe Ser Gly Pro Thr Asp Pro Arg Pro Pro
1370             1375                 1380

Pro Arg Arg Ile Ala Val Pro Ser Arg Ser Ser Ala Ser Val Pro
1385             1390                 1395

Lys Pro Ala Pro Gln Pro Tyr Pro Phe Thr Ser Ser Leu Ser Thr
1400             1405                 1410

Ile Asn Tyr Asp Glu Phe Pro Thr Met Val Phe Pro Ser Gly Gln
1415             1420                 1425

Ile Ser Gln Ala Ser Ala Leu Ala Pro Ala Pro Gln Val Leu
1430             1435                 1440

Pro Gln Ala Pro Ala Pro Ala Pro Ala Pro Ala Met Val Ser Ala
1445             1450                 1455

Leu Ala Gln Ala Pro Ala Pro Val Pro Val Leu Ala Pro Gly Pro
1460             1465                 1470

Pro Gln Ala Val Ala Pro Pro Ala Pro Lys Pro Thr Gln Ala Gly
1475             1480                 1485

Glu Gly Thr Leu Ser Glu Ala Leu Leu Gln Leu Gln Phe Asp Asp
1490             1495                 1500

```
Glu Asp Leu Gly Ala Leu Leu Gly Asn Ser Thr Asp Pro Ala Val
    1505                1510                1515

Phe Thr Asp Leu Ala Ser Val Asp Asn Ser Glu Phe Gln Gln Leu
    1520                1525                1530

Leu Asn Gln Gly Ile Pro Val Ala Pro His Thr Thr Glu Pro Met
    1535                1540                1545

Leu Met Glu Tyr Pro Glu Ala Ile Thr Arg Leu Val Thr Gly Ala
    1550                1555                1560

Gln Arg Pro Pro Asp Pro Ala Pro Ala Pro Leu Gly Ala Pro Gly
    1565                1570                1575

Leu Pro Asn Gly Leu Leu Ser Gly Asp Glu Asp Phe Ser Ser Ile
    1580                1585                1590

Ala Asp Met Asp Phe Ser Ala Leu Leu Gly Ser Gly Ser Gly Ser
    1595                1600                1605

Arg Asp Ser Arg Glu Gly Met Phe Leu Pro Lys Pro Glu Ala Gly
    1610                1615                1620

Ser Ala Ile Ser Asp Val Phe Glu Gly Arg Glu Val Cys Gln Pro
    1625                1630                1635

Lys Arg Ile Arg Pro Phe His Pro Pro Gly Ser Pro Trp Ala Asn
    1640                1645                1650

Arg Pro Leu Pro Ala Ser Leu Ala Pro Thr Pro Thr Gly Pro Val
    1655                1660                1665

His Glu Pro Val Gly Ser Leu Thr Pro Ala Pro Val Pro Gln Pro
    1670                1675                1680

Leu Asp Pro Ala Pro Ala Val Thr Pro Glu Ala Ser His Leu Leu
    1685                1690                1695

Glu Asp Pro Asp Glu Glu Thr Ser Gln Ala Val Lys Ala Leu Arg
    1700                1705                1710

Glu Met Ala Asp Thr Val Ile Pro Gln Lys Glu Glu Ala Ala Ile
    1715                1720                1725

Cys Gly Gln Met Asp Leu Ser His Pro Pro Pro Arg Gly His Leu
    1730                1735                1740

Asp Glu Leu Thr Thr Thr Leu Glu Ser Met Thr Glu Asp Leu Asn
    1745                1750                1755

Leu Asp Ser Pro Leu Thr Pro Glu Leu Asn Glu Ile Leu Asp Thr
    1760                1765                1770

Phe Leu Asn Asp Glu Cys Leu Leu His Ala Met His Ile Ser Thr
    1775                1780                1785

Gly Leu Ser Ile Phe Asp Thr Ser Leu Phe
    1790                1795

<210> SEQ ID NO 11
<211> LENGTH: 1597
<212> TYPE: PRT
<213> ORGANISM: Artificial Sequence
<220> FEATURE:
<223> OTHER INFORMATION: Synthetic construct created by rational design

<400> SEQUENCE: 11

Met Pro Lys Lys Lys Arg Lys Val Gly Gly Gly Ser Pro Gly Lys Arg
1               5                   10                  15

Asn Tyr Ile Leu Gly Leu Ala Ile Gly Ile Thr Ser Val Gly Tyr Gly
                20                  25                  30

Ile Ile Asp Tyr Glu Thr Arg Asp Val Ile Asp Ala Gly Val Arg Leu
            35                  40                  45
```

```
Phe Lys Glu Ala Asn Val Glu Asn Asn Glu Gly Arg Ser Lys Arg
    50                  55                  60
Gly Ala Arg Arg Leu Lys Arg Arg Arg His Arg Ile Gln Arg Val
 65              70                  75                  80
Lys Lys Leu Leu Phe Asp Tyr Asn Leu Leu Thr Asp His Ser Glu Leu
                    85                  90                  95
Ser Gly Ile Asn Pro Tyr Glu Ala Arg Val Lys Gly Leu Ser Gln Lys
                100                 105                 110
Leu Ser Glu Glu Glu Phe Ser Ala Leu Leu His Leu Ala Lys Arg
            115                 120                 125
Arg Gly Val His Asn Val Asn Glu Val Glu Glu Asp Thr Gly Asn Glu
    130                 135                 140
Leu Ser Thr Lys Glu Gln Ile Ser Arg Asn Ser Lys Ala Leu Glu Glu
145                 150                 155                 160
Lys Tyr Val Ala Glu Leu Gln Leu Glu Arg Leu Lys Lys Asp Gly Glu
                165                 170                 175
Val Arg Gly Ser Ile Asn Arg Phe Lys Thr Ser Asp Tyr Val Lys Glu
                180                 185                 190
Ala Lys Gln Leu Leu Lys Val Gln Lys Ala Tyr His Gln Leu Asp Gln
            195                 200                 205
Ser Phe Ile Asp Thr Tyr Ile Asp Leu Leu Glu Thr Arg Arg Thr Tyr
    210                 215                 220
Tyr Glu Gly Pro Gly Glu Gly Ser Pro Phe Gly Trp Lys Asp Ile Lys
225                 230                 235                 240
Glu Trp Tyr Glu Met Leu Met Gly His Cys Thr Tyr Phe Pro Glu Glu
                245                 250                 255
Leu Arg Ser Val Lys Tyr Ala Tyr Asn Ala Asp Leu Tyr Asn Ala Leu
            260                 265                 270
Asn Asp Leu Asn Asn Leu Val Ile Thr Arg Asp Glu Asn Glu Lys Leu
    275                 280                 285
Glu Tyr Tyr Glu Lys Phe Gln Ile Ile Glu Asn Val Phe Lys Gln Lys
                290                 295                 300
Lys Lys Pro Thr Leu Lys Gln Ile Ala Lys Glu Ile Leu Val Asn Glu
305                 310                 315                 320
Glu Asp Ile Lys Gly Tyr Arg Val Thr Ser Thr Gly Lys Pro Glu Phe
                325                 330                 335
Thr Asn Leu Lys Val Tyr His Asp Ile Lys Asp Ile Thr Ala Arg Lys
            340                 345                 350
Glu Ile Ile Glu Asn Ala Glu Leu Leu Asp Gln Ile Ala Lys Ile Leu
    355                 360                 365
Thr Ile Tyr Gln Ser Ser Glu Asp Ile Gln Glu Glu Leu Thr Asn Leu
370                 375                 380
Asn Ser Glu Leu Thr Gln Glu Glu Ile Glu Gln Ile Ser Asn Leu Lys
            385                 390                 395                 400
Gly Tyr Thr Gly Thr His Asn Leu Ser Leu Lys Ala Ile Asn Leu Ile
                405                 410                 415
Leu Asp Glu Leu Trp His Thr Asn Asp Asn Gln Ile Ala Ile Phe Asn
            420                 425                 430
Arg Leu Lys Leu Val Pro Lys Lys Val Asp Leu Ser Gln Gln Lys Glu
    435                 440                 445
Ile Pro Thr Thr Leu Val Asp Asp Phe Ile Leu Ser Pro Val Val Lys
450                 455                 460
Arg Ser Phe Ile Gln Ser Ile Lys Val Ile Asn Ala Ile Ile Lys Lys
```

```
            465                 470                 475                 480
Tyr Gly Leu Pro Asn Asp Ile Ile Glu Leu Ala Arg Glu Lys Asn
                485                 490                 495

Ser Lys Asp Ala Gln Lys Met Ile Asn Glu Met Gln Lys Arg Asn Arg
                500                 505                 510

Gln Thr Asn Glu Arg Ile Glu Glu Ile Ile Arg Thr Thr Gly Lys Glu
                515                 520                 525

Asn Ala Lys Tyr Leu Ile Glu Lys Ile Lys Leu His Asp Met Gln Glu
                530                 535                 540

Gly Lys Cys Leu Tyr Ser Leu Glu Ala Ile Pro Leu Glu Asp Leu Leu
545                 550                 555                 560

Asn Asn Pro Phe Asn Tyr Glu Val Asp His Ile Ile Pro Arg Ser Val
                565                 570                 575

Ser Phe Asp Asn Ser Phe Asn Asn Lys Val Leu Val Lys Gln Glu Glu
                580                 585                 590

Ala Ser Lys Lys Gly Asn Arg Thr Pro Phe Gln Tyr Leu Ser Ser Ser
                595                 600                 605

Asp Ser Lys Ile Ser Tyr Glu Thr Phe Lys Lys His Ile Leu Asn Leu
                610                 615                 620

Ala Lys Gly Lys Gly Arg Ile Ser Lys Thr Lys Lys Glu Tyr Leu Leu
625                 630                 635                 640

Glu Glu Arg Asp Ile Asn Arg Phe Ser Val Gln Lys Asp Phe Ile Asn
                645                 650                 655

Arg Asn Leu Val Asp Thr Arg Tyr Ala Thr Arg Gly Leu Met Asn Leu
                660                 665                 670

Leu Arg Ser Tyr Phe Arg Val Asn Asn Leu Asp Val Lys Val Lys Ser
                675                 680                 685

Ile Asn Gly Gly Phe Thr Ser Phe Leu Arg Arg Lys Trp Lys Phe Lys
                690                 695                 700

Lys Glu Arg Asn Lys Gly Tyr Lys His His Ala Glu Asp Ala Leu Ile
705                 710                 715                 720

Ile Ala Asn Ala Asp Phe Ile Phe Lys Glu Trp Lys Lys Leu Asp Lys
                725                 730                 735

Ala Lys Lys Val Met Glu Asn Gln Met Phe Glu Glu Lys Gln Ala Glu
                740                 745                 750

Ser Met Pro Glu Ile Glu Thr Glu Gln Glu Tyr Lys Glu Ile Phe Ile
                755                 760                 765

Thr Pro His Gln Ile Lys His Ile Lys Asp Phe Lys Asp Tyr Lys Tyr
                770                 775                 780

Ser His Arg Val Asp Lys Lys Pro Asn Arg Lys Leu Ile Asn Asp Thr
785                 790                 795                 800

Leu Tyr Ser Thr Arg Lys Asp Asp Lys Gly Asn Thr Leu Ile Val Asn
                805                 810                 815

Asn Leu Asn Gly Leu Tyr Asp Lys Asp Asn Asp Lys Leu Lys Lys Leu
                820                 825                 830

Ile Asn Lys Ser Pro Glu Lys Leu Leu Met Tyr His His Asp Pro Gln
                835                 840                 845

Thr Tyr Gln Lys Leu Lys Leu Ile Met Glu Gln Tyr Gly Asp Glu Lys
                850                 855                 860

Asn Pro Leu Tyr Lys Tyr Tyr Glu Glu Thr Gly Asn Tyr Leu Thr Lys
865                 870                 875                 880

Tyr Ser Lys Lys Asp Asn Gly Pro Val Ile Lys Lys Ile Lys Tyr Tyr
                885                 890                 895
```

```
Gly Asn Lys Leu Asn Ala His Leu Asp Ile Thr Asp Tyr Pro Asn
            900                 905                 910

Ser Arg Asn Lys Val Val Lys Leu Ser Leu Lys Pro Tyr Arg Phe Asp
            915                 920                 925

Val Tyr Leu Asp Asn Gly Val Tyr Lys Phe Val Thr Val Lys Asn Leu
            930                 935                 940

Asp Val Ile Lys Lys Glu Asn Tyr Tyr Glu Val Asn Ser Lys Cys Tyr
945                 950                 955                 960

Glu Glu Ala Lys Lys Leu Lys Lys Ile Ser Asn Gln Ala Glu Phe Ile
            965                 970                 975

Ala Ser Phe Tyr Lys Asn Asp Leu Ile Lys Ile Asn Gly Glu Leu Tyr
            980                 985                 990

Arg Val Ile Gly Val Asn Asn Asp Leu Leu Asn Arg Ile Glu Val Asn
            995                 1000                1005

Met Ile Asp Ile Thr Tyr Arg Glu Tyr Leu Glu Asn Met Asn Asp
        1010                1015                1020

Lys Arg Pro Pro His Ile Ile Lys Thr Ile Ala Ser Lys Thr Gln
        1025                1030                1035

Ser Ile Lys Lys Tyr Ser Thr Asp Ile Leu Gly Asn Leu Tyr Glu
        1040                1045                1050

Val Lys Ser Lys Lys His Pro Gln Ile Ile Lys Lys Gly Thr Ser
        1055                1060                1065

Arg Ala Asp Pro Lys Lys Lys Arg Lys Val Glu Ala Ser Gly Ser
        1070                1075                1080

Gly Arg Ala Asp Ala Leu Asp Asp Phe Asp Leu Asp Met Leu Gly
        1085                1090                1095

Ser Asp Ala Leu Asp Asp Phe Asp Leu Asp Met Leu Gly Ser Asp
        1100                1105                1110

Ala Leu Asp Asp Phe Asp Leu Asp Met Leu Gly Ser Asp Ala Leu
        1115                1120                1125

Asp Asp Phe Asp Leu Asp Met Leu Ile Asn Ser Arg Ser Gln Tyr
        1130                1135                1140

Leu Pro Asp Thr Asp Asp Arg His Arg Ile Glu Glu Lys Arg Lys
        1145                1150                1155

Arg Thr Tyr Glu Thr Phe Lys Ser Ile Met Lys Lys Ser Pro Phe
        1160                1165                1170

Ser Gly Pro Thr Asp Pro Arg Pro Pro Arg Arg Ile Ala Val
        1175                1180                1185

Pro Ser Arg Ser Ser Ala Ser Val Pro Lys Pro Ala Pro Gln Pro
        1190                1195                1200

Tyr Pro Phe Thr Ser Ser Leu Ser Thr Ile Asn Tyr Asp Glu Phe
        1205                1210                1215

Pro Thr Met Val Phe Pro Ser Gly Gln Ile Ser Gln Ala Ser Ala
        1220                1225                1230

Leu Ala Pro Ala Pro Pro Gln Val Leu Pro Gln Ala Pro Ala Pro
        1235                1240                1245

Ala Pro Ala Pro Ala Met Val Ser Ala Leu Ala Gln Ala Pro Ala
        1250                1255                1260

Pro Val Pro Val Leu Ala Pro Gly Pro Pro Gln Ala Val Ala Pro
        1265                1270                1275

Pro Ala Pro Lys Pro Thr Gln Ala Gly Glu Gly Thr Leu Ser Glu
        1280                1285                1290
```

-continued

Ala Leu Gln Leu Gln Phe Asp Asp Glu Asp Leu Gly Ala Leu
    1295                1300                1305

Leu Gly Asn Ser Thr Asp Pro Ala Val Phe Thr Asp Leu Ala Ser
1310                1315                1320

Val Asp Asn Ser Glu Phe Gln Gln Leu Leu Asn Gln Gly Ile Pro
    1325                1330                1335

Val Ala Pro His Thr Thr Glu Pro Met Leu Met Glu Tyr Pro Glu
1340                1345                1350

Ala Ile Thr Arg Leu Val Thr Gly Ala Gln Arg Pro Pro Asp Pro
    1355                1360                1365

Ala Pro Ala Pro Leu Gly Ala Pro Gly Leu Pro Asn Gly Leu Leu
1370                1375                1380

Ser Gly Asp Glu Asp Phe Ser Ser Ile Ala Asp Met Asp Phe Ser
    1385                1390                1395

Ala Leu Leu Gly Ser Gly Ser Gly Ser Arg Asp Ser Arg Glu Gly
1400                1405                1410

Met Phe Leu Pro Lys Pro Glu Ala Gly Ser Ala Ile Ser Asp Val
    1415                1420                1425

Phe Glu Gly Arg Glu Val Cys Gln Pro Lys Arg Ile Arg Pro Phe
1430                1435                1440

His Pro Pro Gly Ser Pro Trp Ala Asn Arg Pro Leu Pro Ala Ser
    1445                1450                1455

Leu Ala Pro Thr Pro Thr Gly Pro Val His Glu Pro Val Gly Ser
1460                1465                1470

Leu Thr Pro Ala Pro Val Pro Gln Pro Leu Asp Pro Ala Pro Ala
    1475                1480                1485

Val Thr Pro Glu Ala Ser His Leu Leu Glu Asp Pro Asp Glu Glu
1490                1495                1500

Thr Ser Gln Ala Val Lys Ala Leu Arg Glu Met Ala Asp Thr Val
    1505                1510                1515

Ile Pro Gln Lys Glu Glu Ala Ala Ile Cys Gly Gln Met Asp Leu
1520                1525                1530

Ser His Pro Pro Pro Arg Gly His Leu Asp Glu Leu Thr Thr Thr
    1535                1540                1545

Leu Glu Ser Met Thr Glu Asp Leu Asn Leu Asp Ser Pro Leu Thr
1550                1555                1560

Pro Glu Leu Asn Glu Ile Leu Asp Thr Phe Leu Asn Asp Glu Cys
    1565                1570                1575

Leu Leu His Ala Met His Ile Ser Thr Gly Leu Ser Ile Phe Asp
1580                1585                1590

Thr Ser Leu Phe
    1595

<210> SEQ ID NO 12
<211> LENGTH: 1393
<212> TYPE: PRT
<213> ORGANISM: Artificial Sequence
<220> FEATURE:
<223> OTHER INFORMATION: Synthetic construct created by rational design

<400> SEQUENCE: 12

Met Pro Lys Lys Lys Arg Lys Val Gly Gly Gly Ser Pro Gly Lys Arg
1               5                   10                  15

Asn Tyr Ile Leu Gly Leu Asp Ile Gly Ile Thr Ser Val Gly Tyr Gly
            20                  25                  30

```
Ile Ile Asp Tyr Glu Thr Arg Asp Val Ile Asp Ala Gly Val Arg Leu
         35                  40                  45
Phe Lys Glu Ala Asn Val Glu Asn Asn Glu Gly Arg Arg Ser Lys Arg
 50                  55                  60
Gly Ala Arg Arg Leu Lys Arg Arg Arg His Arg Ile Gln Arg Val
 65                  70                  75                  80
Lys Lys Leu Leu Phe Asp Tyr Asn Leu Leu Thr Asp His Ser Glu Leu
                 85                  90                  95
Ser Gly Ile Asn Pro Tyr Glu Ala Arg Val Lys Gly Leu Ser Gln Lys
                100                 105                 110
Leu Ser Glu Glu Phe Ser Ala Ala Leu Leu His Leu Ala Lys Arg
        115                 120                 125
Arg Gly Val His Asn Val Asn Glu Val Glu Glu Asp Thr Gly Asn Glu
        130                 135                 140
Leu Ser Thr Lys Glu Gln Ile Ser Arg Asn Ser Lys Ala Leu Glu Glu
145                 150                 155                 160
Lys Tyr Val Ala Glu Leu Gln Leu Glu Arg Leu Lys Lys Asp Gly Glu
                165                 170                 175
Val Arg Gly Ser Ile Asn Arg Phe Lys Thr Ser Asp Tyr Val Lys Glu
            180                 185                 190
Ala Lys Gln Leu Leu Lys Val Gln Lys Ala Tyr His Gln Leu Asp Gln
        195                 200                 205
Ser Phe Ile Asp Thr Tyr Ile Asp Leu Leu Glu Thr Arg Arg Thr Tyr
210                 215                 220
Tyr Glu Gly Pro Gly Glu Gly Ser Pro Phe Gly Trp Lys Asp Ile Lys
225                 230                 235                 240
Glu Trp Tyr Glu Met Leu Gly Gly Ser Gly Gly Gly Ile Leu Ser
                245                 250                 255
Pro Val Val Lys Arg Ser Phe Ile Gln Ser Ile Lys Val Ile Asn Ala
                260                 265                 270
Ile Ile Lys Lys Tyr Gly Leu Pro Asn Asp Ile Ile Glu Leu Ala
        275                 280                 285
Arg Glu Lys Asn Ser Lys Asp Ala Gln Lys Met Ile Asn Glu Met Gln
290                 295                 300
Lys Arg Asn Arg Gln Thr Asn Glu Arg Ile Glu Glu Ile Ile Arg Thr
305                 310                 315                 320
Thr Gly Lys Glu Asn Ala Lys Tyr Leu Ile Glu Lys Ile Lys Leu His
                325                 330                 335
Asp Met Gln Glu Gly Lys Cys Leu Tyr Ser Leu Glu Ala Ile Pro Leu
            340                 345                 350
Glu Asp Leu Leu Asn Asn Pro Phe Asn Tyr Glu Val Asp His Ile Ile
        355                 360                 365
Pro Arg Ser Val Ser Phe Asp Asn Ser Phe Asn Asn Lys Val Leu Val
        370                 375                 380
Lys Gln Glu Glu Asn Ser Lys Lys Gly Asn Arg Thr Pro Phe Gln Tyr
385                 390                 395                 400
Leu Ser Ser Ser Asp Ser Lys Ile Ser Tyr Glu Thr Phe Lys Lys His
                405                 410                 415
Ile Leu Asn Leu Ala Lys Gly Lys Gly Arg Ile Ser Lys Thr Lys Lys
                420                 425                 430
Glu Tyr Leu Leu Glu Glu Arg Asp Ile Asn Arg Phe Ser Val Gln Lys
        435                 440                 445
Asp Phe Ile Asn Arg Asn Leu Val Asp Thr Arg Tyr Ala Thr Arg Gly
```

```
                450             455             460
Leu Met Asn Leu Leu Arg Ser Tyr Phe Arg Val Asn Asn Leu Asp Val
465             470             475             480

Lys Val Lys Ser Ile Asn Gly Gly Phe Thr Ser Phe Leu Arg Arg Lys
                485             490             495

Trp Lys Phe Lys Lys Glu Arg Asn Lys Gly Tyr Lys His His Ala Glu
                500             505             510

Asp Ala Leu Ile Ile Ala Asn Ala Asp Phe Ile Phe Lys Glu Trp Lys
                515             520             525

Lys Leu Asp Lys Ala Lys Lys Val Met Glu Asn Gln Met Phe Glu Glu
                530             535             540

Lys Gln Ala Glu Ser Met Pro Glu Ile Glu Thr Glu Gln Glu Tyr Lys
545             550             555             560

Glu Ile Phe Ile Thr Pro His Gln Ile Lys His Ile Lys Asp Phe Lys
                565             570             575

Asp Tyr Lys Tyr Ser His Arg Val Asp Lys Lys Pro Asn Arg Lys Leu
                580             585             590

Ile Asn Asp Thr Leu Tyr Ser Thr Arg Lys Asp Asp Lys Gly Asn Thr
                595             600             605

Leu Ile Val Asn Asn Leu Asn Gly Leu Tyr Asp Lys Asp Asn Asp Lys
610             615             620

Leu Lys Lys Leu Ile Asn Lys Ser Pro Glu Lys Leu Leu Met Tyr His
625             630             635             640

His Asp Pro Gln Thr Tyr Gln Lys Leu Lys Leu Ile Met Glu Gln Tyr
                645             650             655

Gly Asp Glu Lys Asn Pro Leu Tyr Lys Tyr Tyr Glu Glu Thr Gly Asn
                660             665             670

Tyr Leu Thr Lys Tyr Ser Lys Lys Asp Asn Gly Pro Val Ile Lys Lys
                675             680             685

Ile Lys Tyr Tyr Gly Asn Lys Leu Asn Ala His Leu Asp Ile Thr Asp
                690             695             700

Asp Tyr Pro Asn Ser Arg Asn Lys Val Val Lys Leu Ser Leu Lys Pro
705             710             715             720

Tyr Arg Phe Asp Val Tyr Leu Asp Asn Gly Val Tyr Lys Phe Val Thr
                725             730             735

Val Lys Asn Leu Asp Val Ile Lys Lys Glu Asn Tyr Tyr Glu Val Asn
                740             745             750

Ser Lys Cys Tyr Glu Glu Ala Lys Lys Leu Lys Lys Ile Ser Asn Gln
                755             760             765

Ala Glu Phe Ile Ala Ser Phe Tyr Lys Asn Asp Leu Ile Lys Ile Asn
                770             775             780

Gly Glu Leu Tyr Arg Val Ile Gly Val Asn Asn Asp Leu Leu Asn Arg
785             790             795             800

Ile Glu Val Asn Met Ile Asp Ile Thr Tyr Arg Glu Tyr Leu Glu Asn
                805             810             815

Met Asn Asp Lys Arg Pro Pro His Ile Ile Lys Thr Ile Ala Ser Lys
                820             825             830

Thr Gln Ser Ile Lys Lys Tyr Ser Thr Asp Ile Leu Gly Asn Leu Tyr
                835             840             845

Glu Val Lys Ser Lys Lys His Pro Gln Ile Ile Lys Lys Gly Thr Ser
850             855             860

Arg Ala Asp Pro Lys Lys Lys Arg Lys Val Glu Ala Ser Gly Ser Gly
865             870             875             880
```

-continued

```
Arg Ala Asp Ala Leu Asp Asp Phe Asp Leu Asp Met Leu Gly Ser Asp
            885                 890                 895

Ala Leu Asp Asp Phe Asp Leu Asp Met Leu Gly Ser Asp Ala Leu Asp
        900                 905                 910

Asp Phe Asp Leu Asp Met Leu Gly Ser Asp Ala Leu Asp Phe Asp
        915                 920                 925

Leu Asp Met Leu Ile Asn Ser Arg Ser Gln Tyr Leu Pro Asp Thr Asp
    930                 935                 940

Asp Arg His Arg Ile Glu Glu Lys Arg Lys Arg Thr Tyr Glu Thr Phe
945                 950                 955                 960

Lys Ser Ile Met Lys Lys Ser Pro Phe Ser Gly Pro Thr Asp Pro Arg
            965                 970                 975

Pro Pro Pro Arg Arg Ile Ala Val Pro Ser Arg Ser Ser Ala Ser Val
            980                 985                 990

Pro Lys Pro Ala Pro Gln Pro Tyr Pro Phe Thr Ser Ser Leu Ser Thr
        995                 1000                1005

Ile Asn Tyr Asp Glu Phe Pro Thr Met Val Phe Pro Ser Gly Gln
    1010                1015                1020

Ile Ser Gln Ala Ser Ala Leu Ala Pro Ala Pro Pro Gln Val Leu
    1025                1030                1035

Pro Gln Ala Pro Ala Pro Pro Ala Pro Ala Met Val Ser Ala
    1040                1045                1050

Leu Ala Gln Ala Pro Ala Pro Val Pro Val Leu Ala Pro Gly Pro
    1055                1060                1065

Pro Gln Ala Val Ala Pro Pro Ala Pro Lys Pro Thr Gln Ala Gly
    1070                1075                1080

Glu Gly Thr Leu Ser Glu Ala Leu Leu Gln Leu Gln Phe Asp Asp
    1085                1090                1095

Glu Asp Leu Gly Ala Leu Leu Gly Asn Ser Thr Asp Pro Ala Val
    1100                1105                1110

Phe Thr Asp Leu Ala Ser Val Asp Asn Ser Glu Phe Gln Gln Leu
    1115                1120                1125

Leu Asn Gln Gly Ile Pro Val Ala Pro His Thr Thr Glu Pro Met
    1130                1135                1140

Leu Met Glu Tyr Pro Glu Ala Ile Thr Arg Leu Val Thr Gly Ala
    1145                1150                1155

Gln Arg Pro Pro Asp Pro Ala Pro Ala Pro Leu Gly Ala Pro Gly
    1160                1165                1170

Leu Pro Asn Gly Leu Leu Ser Gly Asp Glu Asp Phe Ser Ser Ile
    1175                1180                1185

Ala Asp Met Asp Phe Ser Ala Leu Leu Gly Ser Gly Ser Gly Ser
    1190                1195                1200

Arg Asp Ser Arg Glu Gly Met Phe Leu Pro Lys Pro Glu Ala Gly
    1205                1210                1215

Ser Ala Ile Ser Asp Val Phe Glu Gly Arg Glu Val Cys Gln Pro
    1220                1225                1230

Lys Arg Ile Arg Pro Phe His Pro Pro Gly Ser Pro Trp Ala Asn
    1235                1240                1245

Arg Pro Leu Pro Ala Ser Leu Ala Pro Thr Pro Thr Gly Pro Val
    1250                1255                1260

His Glu Pro Val Gly Ser Leu Thr Pro Ala Pro Val Pro Gln Pro
    1265                1270                1275
```

```
Leu Asp Pro Ala Pro Ala Val Thr Pro Glu Ala Ser His Leu Leu
    1280            1285            1290

Glu Asp Pro Asp Glu Glu Thr Ser Gln Ala Val Lys Ala Leu Arg
    1295            1300            1305

Glu Met Ala Asp Thr Val Ile Pro Gln Lys Glu Ala Ala Ile
    1310            1315            1320

Cys Gly Gln Met Asp Leu Ser His Pro Pro Arg Gly His Leu
    1325            1330            1335

Asp Glu Leu Thr Thr Thr Leu Glu Ser Met Thr Glu Asp Leu Asn
    1340            1345            1350

Leu Asp Ser Pro Leu Thr Pro Glu Leu Asn Glu Ile Leu Asp Thr
    1355            1360            1365

Phe Leu Asn Asp Glu Cys Leu Leu His Ala Met His Ile Ser Thr
    1370            1375            1380

Gly Leu Ser Ile Phe Asp Thr Ser Leu Phe
    1385            1390

<210> SEQ ID NO 13
<211> LENGTH: 1393
<212> TYPE: PRT
<213> ORGANISM: Artificial Sequence
<220> FEATURE:
<223> OTHER INFORMATION: Synthetic construct created by rational design

<400> SEQUENCE: 13

Met Pro Lys Lys Lys Arg Lys Val Gly Gly Ser Pro Gly Lys Arg
1               5                   10                  15

Asn Tyr Ile Leu Gly Leu Asp Ile Gly Ile Thr Ser Val Gly Tyr Gly
                20                  25                  30

Ile Ile Asp Tyr Glu Thr Arg Asp Val Ile Asp Ala Gly Val Arg Leu
            35                  40                  45

Phe Lys Glu Ala Asn Val Glu Asn Asn Glu Gly Arg Arg Ser Lys Arg
        50                  55                  60

Gly Ala Arg Arg Leu Lys Arg Arg Arg Arg His Arg Ile Gln Arg Val
65                  70                  75                  80

Lys Lys Leu Leu Phe Asp Tyr Asn Leu Leu Thr Asp His Ser Glu Leu
                85                  90                  95

Ser Gly Ile Asn Pro Tyr Glu Ala Arg Val Lys Gly Leu Ser Gln Lys
                100                 105                 110

Leu Ser Glu Glu Glu Phe Ser Ala Ala Leu Leu His Leu Ala Lys Arg
            115                 120                 125

Arg Gly Val His Asn Val Asn Glu Val Glu Glu Asp Thr Gly Asn Glu
        130                 135                 140

Leu Ser Thr Lys Glu Gln Ile Ser Arg Asn Ser Lys Ala Leu Glu Glu
145                 150                 155                 160

Lys Tyr Val Ala Glu Leu Gln Leu Glu Arg Leu Lys Lys Asp Gly Glu
                165                 170                 175

Val Arg Gly Ser Ile Asn Arg Phe Lys Thr Ser Asp Tyr Val Lys Glu
                180                 185                 190

Ala Lys Gln Leu Leu Lys Val Gln Lys Ala Tyr His Gln Leu Asp Gln
            195                 200                 205

Ser Phe Ile Asp Thr Tyr Ile Asp Leu Leu Glu Thr Arg Arg Thr Tyr
        210                 215                 220

Tyr Glu Gly Pro Gly Glu Gly Ser Pro Phe Gly Trp Lys Asp Ile Lys
225                 230                 235                 240
```

```
Glu Trp Tyr Glu Met Leu Lys Arg Arg Arg His Arg Ile Leu Ser
            245                 250                 255

Pro Val Val Lys Arg Ser Phe Ile Gln Ser Ile Lys Val Ile Asn Ala
        260                 265                 270

Ile Ile Lys Lys Tyr Gly Leu Pro Asn Asp Ile Ile Glu Leu Ala
        275                 280             285

Arg Glu Lys Asn Ser Lys Asp Ala Gln Lys Met Ile Asn Glu Met Gln
        290                 295             300

Lys Arg Asn Arg Gln Thr Asn Glu Arg Ile Glu Ile Ile Arg Thr
305             310             315                 320

Thr Gly Lys Glu Asn Ala Lys Tyr Leu Ile Glu Lys Ile Lys Leu His
            325             330              335

Asp Met Gln Glu Gly Lys Cys Leu Tyr Ser Leu Glu Ala Ile Pro Leu
            340             345             350

Glu Asp Leu Leu Asn Asn Pro Phe Asn Tyr Glu Val Asp His Ile Ile
        355             360             365

Pro Arg Ser Val Ser Phe Asp Asn Ser Phe Asn Asn Lys Val Leu Val
370             375             380

Lys Gln Glu Glu Asn Ser Lys Lys Gly Asn Arg Thr Pro Phe Gln Tyr
385             390             395             400

Leu Ser Ser Ser Asp Ser Lys Ile Ser Tyr Glu Thr Phe Lys Lys His
            405             410             415

Ile Leu Asn Leu Ala Lys Gly Lys Gly Arg Ile Ser Lys Thr Lys Lys
            420             425             430

Glu Tyr Leu Leu Glu Glu Arg Asp Ile Asn Arg Phe Ser Val Gln Lys
        435             440             445

Asp Phe Ile Asn Arg Asn Leu Val Asp Thr Arg Tyr Ala Thr Arg Gly
        450             455             460

Leu Met Asn Leu Leu Arg Ser Tyr Phe Arg Val Asn Asn Leu Asp Val
465             470             475             480

Lys Val Lys Ser Ile Asn Gly Gly Phe Thr Ser Phe Leu Arg Arg Lys
            485             490             495

Trp Lys Phe Lys Lys Glu Arg Asn Lys Gly Tyr Lys His His Ala Glu
            500             505             510

Asp Ala Leu Ile Ile Ala Asn Ala Asp Phe Ile Phe Lys Glu Trp Lys
        515             520             525

Lys Leu Asp Lys Ala Lys Lys Val Met Glu Asn Gln Met Phe Glu Glu
        530             535             540

Lys Gln Ala Glu Ser Met Pro Glu Ile Glu Thr Glu Gln Glu Tyr Lys
545             550             555             560

Glu Ile Phe Ile Thr Pro His Gln Ile Lys His Ile Lys Asp Phe Lys
                565             570             575

Asp Tyr Lys Tyr Ser His Arg Val Asp Lys Lys Pro Asn Arg Lys Leu
        580             585             590

Ile Asn Asp Thr Leu Tyr Ser Thr Arg Lys Asp Asp Lys Gly Asn Thr
        595             600             605

Leu Ile Val Asn Asn Leu Asn Gly Leu Tyr Asp Lys Asp Asn Asp Lys
        610             615             620

Leu Lys Lys Leu Ile Asn Lys Ser Pro Glu Lys Leu Leu Met Tyr His
625             630             635             640

His Asp Pro Gln Thr Tyr Gln Lys Leu Lys Leu Ile Met Glu Gln Tyr
            645             650             655

Gly Asp Glu Lys Asn Pro Leu Tyr Lys Tyr Tyr Glu Glu Thr Gly Asn
```

-continued

```
                660                 665                 670
Tyr Leu Thr Lys Tyr Ser Lys Lys Asp Asn Gly Pro Val Ile Lys Lys
            675                 680                 685

Ile Lys Tyr Tyr Gly Asn Lys Leu Asn Ala His Leu Asp Ile Thr Asp
        690                 695                 700

Asp Tyr Pro Asn Ser Arg Asn Lys Val Val Lys Leu Ser Leu Lys Pro
705                 710                 715                 720

Tyr Arg Phe Asp Val Tyr Leu Asp Asn Gly Val Tyr Lys Phe Val Thr
                725                 730                 735

Val Lys Asn Leu Asp Val Ile Lys Lys Glu Asn Tyr Tyr Glu Val Asn
            740                 745                 750

Ser Lys Cys Tyr Glu Ala Lys Lys Leu Lys Lys Ile Ser Asn Gln
        755                 760                 765

Ala Glu Phe Ile Ala Ser Phe Tyr Lys Asn Asp Leu Ile Lys Ile Asn
        770                 775                 780

Gly Glu Leu Tyr Arg Val Ile Gly Val Asn Asn Asp Leu Leu Asn Arg
785                 790                 795                 800

Ile Glu Val Asn Met Ile Asp Ile Thr Tyr Arg Glu Tyr Leu Glu Asn
                805                 810                 815

Met Asn Asp Lys Arg Pro Pro His Ile Ile Lys Thr Ile Ala Ser Lys
            820                 825                 830

Thr Gln Ser Ile Lys Lys Tyr Ser Thr Asp Ile Leu Gly Asn Leu Tyr
        835                 840                 845

Glu Val Lys Ser Lys Lys His Pro Gln Ile Ile Lys Lys Gly Thr Ser
    850                 855                 860

Arg Ala Asp Pro Lys Lys Lys Arg Lys Val Glu Ala Ser Gly Ser Gly
865                 870                 875                 880

Arg Ala Asp Ala Leu Asp Asp Phe Asp Leu Asp Met Leu Gly Ser Asp
                885                 890                 895

Ala Leu Asp Asp Phe Asp Leu Asp Met Leu Gly Ser Asp Ala Leu Asp
            900                 905                 910

Asp Phe Asp Leu Asp Met Leu Gly Ser Asp Ala Leu Asp Asp Phe Asp
        915                 920                 925

Leu Asp Met Leu Ile Asn Ser Arg Ser Gln Tyr Leu Pro Asp Thr Asp
    930                 935                 940

Asp Arg His Arg Ile Glu Glu Lys Arg Lys Arg Thr Tyr Glu Thr Phe
945                 950                 955                 960

Lys Ser Ile Met Lys Lys Ser Pro Phe Ser Gly Pro Thr Asp Pro Arg
                965                 970                 975

Pro Pro Pro Arg Arg Ile Ala Val Pro Ser Arg Ser Ser Ala Ser Val
            980                 985                 990

Pro Lys Pro Ala Pro Gln Pro Tyr Pro Phe Thr Ser Ser Leu Ser Thr
        995                 1000                1005

Ile Asn Tyr Asp Glu Phe Pro Thr Met Val Phe Pro Ser Gly Gln
    1010                1015                1020

Ile Ser Gln Ala Ser Ala Leu Ala Pro Ala Pro Pro Gln Val Leu
    1025                1030                1035

Pro Gln Ala Pro Ala Pro Ala Pro Ala Pro Ala Met Val Ser Ala
    1040                1045                1050

Leu Ala Gln Ala Pro Ala Pro Val Pro Val Leu Ala Pro Gly Pro
    1055                1060                1065

Pro Gln Ala Val Ala Pro Pro Ala Pro Lys Pro Thr Gln Ala Gly
    1070                1075                1080
```

```
Glu Gly Thr Leu Ser Glu Ala Leu Leu Gln Leu Gln Phe Asp Asp
    1085                1090                1095

Glu Asp Leu Gly Ala Leu Leu Gly Asn Ser Thr Asp Pro Ala Val
    1100                1105                1110

Phe Thr Asp Leu Ala Ser Val Asp Asn Ser Glu Phe Gln Gln Leu
    1115                1120                1125

Leu Asn Gln Gly Ile Pro Val Ala Pro His Thr Thr Glu Pro Met
    1130                1135                1140

Leu Met Glu Tyr Pro Glu Ala Ile Thr Arg Leu Val Thr Gly Ala
    1145                1150                1155

Gln Arg Pro Pro Asp Pro Ala Pro Ala Pro Leu Gly Ala Pro Gly
    1160                1165                1170

Leu Pro Asn Gly Leu Leu Ser Gly Asp Glu Asp Phe Ser Ser Ile
    1175                1180                1185

Ala Asp Met Asp Phe Ser Ala Leu Leu Gly Ser Gly Ser Gly Ser
    1190                1195                1200

Arg Asp Ser Arg Glu Gly Met Phe Leu Pro Lys Pro Glu Ala Gly
    1205                1210                1215

Ser Ala Ile Ser Asp Val Phe Glu Gly Arg Glu Val Cys Gln Pro
    1220                1225                1230

Lys Arg Ile Arg Pro Phe His Pro Pro Gly Ser Pro Trp Ala Asn
    1235                1240                1245

Arg Pro Leu Pro Ala Ser Leu Ala Pro Thr Pro Thr Gly Pro Val
    1250                1255                1260

His Glu Pro Val Gly Ser Leu Thr Pro Ala Pro Val Pro Gln Pro
    1265                1270                1275

Leu Asp Pro Ala Pro Ala Val Thr Pro Glu Ala Ser His Leu Leu
    1280                1285                1290

Glu Asp Pro Asp Glu Glu Thr Ser Gln Ala Val Lys Ala Leu Arg
    1295                1300                1305

Glu Met Ala Asp Thr Val Ile Pro Gln Lys Glu Glu Ala Ala Ile
    1310                1315                1320

Cys Gly Gln Met Asp Leu Ser His Pro Pro Pro Arg Gly His Leu
    1325                1330                1335

Asp Glu Leu Thr Thr Thr Leu Glu Ser Met Thr Glu Asp Leu Asn
    1340                1345                1350

Leu Asp Ser Pro Leu Thr Pro Glu Leu Asn Glu Ile Leu Asp Thr
    1355                1360                1365

Phe Leu Asn Asp Glu Cys Leu Leu His Ala Met His Ile Ser Thr
    1370                1375                1380

Gly Leu Ser Ile Phe Asp Thr Ser Leu Phe
    1385                1390

<210> SEQ ID NO 14
<211> LENGTH: 1225
<212> TYPE: PRT
<213> ORGANISM: Artificial Sequence
<220> FEATURE:
<223> OTHER INFORMATION: Synthetic construct created by rational design

<400> SEQUENCE: 14

Met Pro Lys Lys Lys Arg Lys Val Gly Gly Gly Ser Pro Gly Lys Arg
1               5                   10                  15

Asn Tyr Ile Leu Gly Leu Asp Ile Gly Ile Thr Ser Val Gly Tyr Gly
            20                  25                  30
```

```
Ile Ile Asp Tyr Glu Thr Arg Asp Val Ile Asp Ala Gly Val Arg Leu
        35                  40                  45
Phe Lys Glu Ala Asn Val Glu Asn Asn Glu Gly Arg Arg Ser Lys Arg
 50                  55                  60
Gly Ala Arg Arg Leu Lys Arg Arg Arg His Arg Ile Gln Arg Val
 65                  70                  75                  80
Lys Lys Leu Leu Phe Asp Tyr Asn Leu Leu Thr Asp His Ser Glu Leu
                    85                  90                  95
Ser Gly Ile Asn Pro Tyr Glu Ala Arg Val Lys Gly Leu Ser Gln Lys
                    100                 105                 110
Leu Ser Glu Glu Glu Phe Ser Ala Ala Leu Leu His Leu Ala Lys Arg
                115                 120                 125
Arg Gly Val His Asn Val Asn Glu Val Glu Glu Asp Thr Gly Asn Glu
            130                 135                 140
Leu Ser Thr Lys Glu Gln Ile Ser Arg Asn Ser Lys Ala Leu Glu Glu
145                 150                 155                 160
Lys Tyr Val Ala Glu Leu Gln Leu Glu Arg Leu Lys Lys Asp Gly Glu
                    165                 170                 175
Val Arg Gly Ser Ile Asn Arg Phe Lys Thr Ser Asp Tyr Val Lys Glu
                180                 185                 190
Ala Lys Gln Leu Leu Lys Val Gln Lys Ala Tyr His Gln Leu Asp Gln
            195                 200                 205
Ser Phe Ile Asp Thr Tyr Ile Asp Leu Leu Glu Thr Arg Arg Thr Tyr
        210                 215                 220
Tyr Glu Gly Pro Gly Glu Gly Ser Pro Phe Gly Trp Lys Asp Ile Lys
225                 230                 235                 240
Glu Trp Tyr Glu Met Leu Lys Arg Arg Arg His Arg Ile Leu Ser
                    245                 250                 255
Pro Val Val Lys Arg Ser Phe Ile Gln Ser Ile Lys Val Ile Asn Ala
                260                 265                 270
Ile Ile Lys Lys Tyr Gly Leu Pro Asn Asp Ile Ile Glu Leu Gly
            275                 280                 285
Ser Lys Arg Tyr Ala Thr Arg Gly Leu Met Asn Leu Leu Arg Ser Tyr
290                 295                 300
Phe Arg Val Asn Asn Leu Asp Val Lys Val Lys Ser Ile Asn Gly Gly
305                 310                 315                 320
Phe Thr Ser Phe Leu Arg Arg Lys Trp Lys Phe Lys Lys Glu Arg Asn
                325                 330                 335
Lys Gly Tyr Lys His His Ala Glu Asp Ala Leu Ile Ile Ala Asn Ala
                340                 345                 350
Asp Phe Ile Phe Lys Glu Trp Lys Lys Leu Asp Lys Ala Lys Lys Val
                355                 360                 365
Met Glu Asn Gln Met Phe Glu Glu Lys Gln Ala Glu Ser Met Pro Glu
    370                 375                 380
Ile Glu Thr Glu Gln Glu Tyr Lys Glu Ile Phe Ile Thr Pro His Gln
385                 390                 395                 400
Ile Lys His Ile Lys Asp Phe Lys Asp Tyr Lys Tyr Ser His Arg Val
                405                 410                 415
Asp Lys Lys Pro Asn Arg Lys Leu Ile Asn Asp Thr Leu Tyr Ser Thr
                420                 425                 430
Arg Lys Asp Asp Lys Gly Asn Thr Leu Ile Val Asn Asn Leu Asn Gly
                435                 440                 445
```

```
Leu Tyr Asp Lys Asp Asn Asp Lys Leu Lys Lys Leu Ile Asn Lys Ser
    450                 455                 460

Pro Glu Lys Leu Leu Met Tyr His His Asp Pro Gln Thr Tyr Gln Lys
465                 470                 475                 480

Leu Lys Leu Ile Met Glu Gln Tyr Gly Asp Glu Lys Asn Pro Leu Tyr
                485                 490                 495

Lys Tyr Tyr Glu Glu Thr Gly Asn Tyr Leu Thr Lys Tyr Ser Lys Lys
            500                 505                 510

Asp Asn Gly Pro Val Ile Lys Ile Lys Tyr Tyr Gly Asn Lys Leu
            515                 520                 525

Asn Ala His Leu Asp Ile Thr Asp Asp Tyr Pro Asn Ser Arg Asn Lys
530                 535                 540

Val Val Lys Leu Ser Leu Lys Pro Tyr Arg Phe Asp Val Tyr Leu Asp
545                 550                 555                 560

Asn Gly Val Tyr Lys Phe Val Thr Val Lys Asn Leu Asp Val Ile Lys
                565                 570                 575

Lys Glu Asn Tyr Tyr Glu Val Asn Ser Lys Cys Tyr Glu Glu Ala Lys
            580                 585                 590

Lys Leu Lys Lys Ile Ser Asn Gln Ala Glu Phe Ile Ala Ser Phe Tyr
    595                 600                 605

Lys Asn Asp Leu Ile Lys Ile Asn Gly Glu Leu Tyr Arg Val Ile Gly
    610                 615                 620

Val Asn Asn Asp Leu Leu Asn Arg Ile Glu Val Asn Met Ile Asp Ile
625                 630                 635                 640

Thr Tyr Arg Glu Tyr Leu Glu Asn Met Asn Asp Lys Arg Pro Pro His
                645                 650                 655

Ile Ile Lys Thr Ile Ala Ser Lys Thr Gln Ser Ile Lys Lys Tyr Ser
            660                 665                 670

Thr Asp Ile Leu Gly Asn Leu Tyr Glu Val Lys Ser Lys Lys His Pro
    675                 680                 685

Gln Ile Ile Lys Lys Gly Thr Ser Arg Ala Asp Pro Lys Lys Lys Arg
    690                 695                 700

Lys Val Glu Ala Ser Gly Ser Gly Arg Ala Asp Ala Leu Asp Asp Phe
705                 710                 715                 720

Asp Leu Asp Met Leu Gly Ser Asp Ala Leu Asp Asp Phe Asp Leu Asp
                725                 730                 735

Met Leu Gly Ser Asp Ala Leu Asp Asp Phe Asp Leu Asp Met Leu Gly
            740                 745                 750

Ser Asp Ala Leu Asp Asp Phe Asp Leu Asp Met Leu Ile Asn Ser Arg
    755                 760                 765

Ser Gln Tyr Leu Pro Asp Thr Asp Asp Arg His Arg Ile Glu Glu Lys
770                 775                 780

Arg Lys Arg Thr Tyr Glu Thr Phe Lys Ser Ile Met Lys Lys Ser Pro
785                 790                 795                 800

Phe Ser Gly Pro Thr Asp Pro Arg Pro Pro Arg Arg Ile Ala Val
                805                 810                 815

Pro Ser Arg Ser Ser Ala Ser Val Pro Lys Pro Ala Pro Gln Pro Tyr
            820                 825                 830

Pro Phe Thr Ser Ser Leu Ser Thr Ile Asn Tyr Asp Glu Phe Pro Thr
            835                 840                 845

Met Val Phe Pro Ser Gly Gln Ile Ser Gln Ala Ser Ala Leu Ala Pro
850                 855                 860

Ala Pro Pro Gln Val Leu Pro Gln Ala Pro Ala Pro Ala Pro Ala Pro
```

```
            865                 870                 875                 880
Ala Met Val Ser Ala Leu Ala Gln Ala Pro Ala Pro Val Pro Val Leu
                    885                 890                 895

Ala Pro Gly Pro Pro Gln Ala Val Ala Pro Pro Ala Pro Lys Pro Thr
            900                 905                 910

Gln Ala Gly Glu Gly Thr Leu Ser Glu Ala Leu Leu Gln Leu Gln Phe
            915                 920                 925

Asp Asp Glu Asp Leu Gly Ala Leu Leu Gly Asn Ser Thr Asp Pro Ala
            930                 935                 940

Val Phe Thr Asp Leu Ala Ser Val Asp Asn Ser Glu Phe Gln Gln Leu
945                 950                 955                 960

Leu Asn Gln Gly Ile Pro Val Ala Pro His Thr Thr Glu Pro Met Leu
                    965                 970                 975

Met Glu Tyr Pro Glu Ala Ile Thr Arg Leu Val Thr Gly Ala Gln Arg
            980                 985                 990

Pro Pro Asp Pro Ala Pro Ala Pro Leu Gly Ala Pro Gly Leu Pro Asn
            995                 1000                1005

Gly Leu Leu Ser Gly Asp Glu Asp Phe Ser Ser Ile Ala Asp Met
            1010                1015                1020

Asp Phe Ser Ala Leu Leu Gly Ser Gly Ser Gly Ser Arg Asp Ser
            1025                1030                1035

Arg Glu Gly Met Phe Leu Pro Lys Pro Glu Ala Gly Ser Ala Ile
            1040                1045                1050

Ser Asp Val Phe Glu Gly Arg Glu Val Cys Gln Pro Lys Arg Ile
            1055                1060                1065

Arg Pro Phe His Pro Pro Gly Ser Pro Trp Ala Asn Arg Pro Leu
            1070                1075                1080

Pro Ala Ser Leu Ala Pro Thr Pro Thr Gly Pro Val His Glu Pro
            1085                1090                1095

Val Gly Ser Leu Thr Pro Ala Pro Val Pro Gln Pro Leu Asp Pro
            1100                1105                1110

Ala Pro Ala Val Thr Pro Glu Ala Ser His Leu Leu Glu Asp Pro
            1115                1120                1125

Asp Glu Glu Thr Ser Gln Ala Val Lys Ala Leu Arg Glu Met Ala
            1130                1135                1140

Asp Thr Val Ile Pro Gln Lys Glu Glu Ala Ala Ile Cys Gly Gln
            1145                1150                1155

Met Asp Leu Ser His Pro Pro Pro Arg Gly His Leu Asp Glu Leu
            1160                1165                1170

Thr Thr Thr Leu Glu Ser Met Thr Glu Asp Leu Asn Leu Asp Ser
            1175                1180                1185

Pro Leu Thr Pro Glu Leu Asn Glu Ile Leu Asp Thr Phe Leu Asn
            1190                1195                1200

Asp Glu Cys Leu Leu His Ala Met His Ile Ser Thr Gly Leu Ser
            1205                1210                1215

Ile Phe Asp Thr Ser Leu Phe
            1220                1225

<210> SEQ ID NO 15
<211> LENGTH: 1852
<212> TYPE: PRT
<213> ORGANISM: Artificial Sequence
<220> FEATURE:
<223> OTHER INFORMATION: Synthetic construct created by rational design
```

<400> SEQUENCE: 15

```
Met Pro Lys Lys Lys Arg Lys Val Gly Gly Ser Pro Gly Met Thr
1               5                   10                  15

Gln Phe Glu Gly Phe Thr Asn Leu Tyr Gln Val Ser Lys Thr Leu Arg
            20                  25                  30

Phe Glu Leu Ile Pro Gln Gly Lys Thr Leu Lys His Ile Gln Glu Gln
        35                  40                  45

Gly Phe Ile Glu Glu Asp Lys Ala Arg Asn Asp His Tyr Lys Glu Leu
    50                  55                  60

Lys Pro Ile Ile Asp Arg Ile Tyr Lys Thr Tyr Ala Asp Gln Cys Leu
65                  70                  75                  80

Gln Leu Val Gln Leu Asp Trp Glu Asn Leu Ser Ala Ala Ile Asp Ser
            85                  90                  95

Tyr Arg Lys Glu Lys Thr Glu Glu Thr Arg Asn Ala Leu Ile Glu Glu
        100                 105                 110

Gln Ala Thr Tyr Arg Asn Ala Ile His Asp Tyr Phe Ile Gly Arg Thr
    115                 120                 125

Asp Asn Leu Thr Asp Ala Ile Asn Lys Arg His Ala Glu Ile Tyr Lys
130                 135                 140

Gly Leu Phe Lys Ala Glu Leu Phe Asn Gly Lys Val Leu Lys Gln Leu
145                 150                 155                 160

Gly Thr Val Thr Thr Thr Glu His Glu Asn Ala Leu Leu Arg Ser Phe
            165                 170                 175

Asp Lys Phe Thr Thr Tyr Phe Ser Gly Phe Tyr Glu Asn Arg Lys Asn
        180                 185                 190

Val Phe Ser Ala Glu Asp Ile Ser Thr Ala Ile Pro His Arg Ile Val
    195                 200                 205

Gln Asp Asn Phe Pro Lys Phe Lys Glu Asn Cys His Ile Phe Thr Arg
210                 215                 220

Leu Ile Thr Ala Val Pro Ser Leu Arg Glu His Phe Glu Asn Val Lys
225                 230                 235                 240

Lys Ala Ile Gly Ile Phe Val Ser Thr Ser Ile Glu Glu Val Phe Ser
            245                 250                 255

Phe Pro Phe Tyr Asn Gln Leu Leu Thr Gln Thr Gln Ile Asp Leu Tyr
        260                 265                 270

Asn Gln Leu Leu Gly Gly Ile Ser Arg Glu Ala Gly Thr Glu Lys Ile
    275                 280                 285

Lys Gly Leu Asn Glu Val Leu Asn Leu Ala Ile Gln Lys Asn Asp Glu
290                 295                 300

Thr Ala His Ile Ile Ala Ser Leu Pro His Arg Phe Ile Pro Leu Phe
305                 310                 315                 320

Lys Gln Ile Leu Ser Asp Arg Asn Thr Leu Ser Phe Ile Leu Glu Glu
            325                 330                 335

Phe Lys Ser Asp Glu Glu Val Ile Gln Ser Phe Cys Lys Tyr Lys Thr
        340                 345                 350

Leu Leu Arg Asn Glu Asn Val Leu Glu Thr Ala Glu Ala Leu Phe Asn
    355                 360                 365

Glu Leu Asn Ser Ile Asp Leu Thr His Ile Phe Ile Ser His Lys Lys
370                 375                 380

Leu Glu Thr Ile Ser Ser Ala Leu Cys Asp His Trp Asp Thr Leu Arg
385                 390                 395                 400

Asn Ala Leu Tyr Glu Arg Arg Ile Ser Glu Leu Thr Gly Lys Ile Thr
            405                 410                 415
```

```
Lys Ser Ala Lys Glu Lys Val Gln Arg Ser Leu Lys His Glu Asp Ile
            420                 425                 430

Asn Leu Gln Glu Ile Ile Ser Ala Ala Gly Lys Glu Leu Ser Glu Ala
            435                 440                 445

Phe Lys Gln Lys Thr Ser Glu Ile Leu Ser His Ala His Ala Ala Leu
            450                 455                 460

Asp Gln Pro Leu Pro Thr Thr Leu Lys Gln Glu Glu Lys Glu Ile
465                 470                 475                 480

Leu Lys Ser Gln Leu Asp Ser Leu Leu Gly Leu Tyr His Leu Leu Asp
                485                 490                 495

Trp Phe Ala Val Asp Glu Ser Asn Glu Val Asp Pro Glu Phe Ser Ala
            500                 505                 510

Arg Leu Thr Gly Ile Lys Leu Glu Met Glu Pro Ser Leu Ser Phe Tyr
            515                 520                 525

Asn Lys Ala Arg Asn Tyr Ala Thr Lys Lys Pro Tyr Ser Val Glu Lys
            530                 535                 540

Phe Lys Leu Asn Phe Gln Met Pro Thr Leu Ala Ser Gly Trp Asp Val
545                 550                 555                 560

Asn Lys Glu Lys Asn Asn Gly Ala Ile Leu Phe Val Lys Asn Gly Leu
            565                 570                 575

Tyr Tyr Leu Gly Ile Met Pro Lys Gln Lys Gly Arg Tyr Lys Ala Leu
            580                 585                 590

Ser Phe Glu Pro Thr Glu Lys Thr Ser Glu Gly Phe Asp Lys Met Tyr
            595                 600                 605

Tyr Asp Tyr Phe Pro Asp Ala Ala Lys Met Ile Pro Lys Cys Ser Thr
            610                 615                 620

Gln Leu Lys Ala Val Thr Ala His Phe Gln Thr His Thr Thr Pro Ile
625                 630                 635                 640

Leu Leu Ser Asn Asn Phe Ile Glu Pro Leu Glu Ile Thr Lys Glu Ile
            645                 650                 655

Tyr Asp Leu Asn Asn Pro Glu Lys Glu Pro Lys Lys Phe Gln Thr Ala
            660                 665                 670

Tyr Ala Lys Lys Thr Gly Asp Gln Lys Gly Tyr Arg Glu Ala Leu Cys
            675                 680                 685

Lys Trp Ile Asp Phe Thr Arg Asp Phe Leu Ser Lys Tyr Thr Lys Thr
            690                 695                 700

Thr Ser Ile Asp Leu Ser Ser Leu Arg Pro Ser Ser Gln Tyr Lys Asp
705                 710                 715                 720

Leu Gly Glu Tyr Tyr Ala Glu Leu Asn Pro Leu Leu Tyr His Ile Ser
                725                 730                 735

Phe Gln Arg Ile Ala Glu Lys Glu Ile Met Asp Ala Val Glu Thr Gly
            740                 745                 750

Lys Leu Tyr Leu Phe Gln Ile Tyr Asn Lys Asp Phe Ala Lys Gly His
            755                 760                 765

His Gly Lys Pro Asn Leu His Thr Leu Tyr Trp Thr Gly Leu Phe Ser
            770                 775                 780

Pro Glu Asn Leu Ala Lys Thr Ser Ile Lys Leu Asn Gly Gln Ala Glu
785                 790                 795                 800

Leu Phe Tyr Arg Pro Lys Ser Arg Met Lys Arg Met Ala His Arg Leu
            805                 810                 815

Gly Glu Lys Met Leu Asn Lys Lys Leu Lys Asp Gln Lys Thr Pro Ile
            820                 825                 830
```

```
Pro Asp Thr Leu Tyr Gln Glu Leu Tyr Asp Tyr Val Asn His Arg Leu
    835                 840                 845

Ser His Asp Leu Ser Asp Glu Ala Arg Ala Leu Leu Pro Asn Val Ile
    850                 855                 860

Thr Lys Glu Val Ser His Glu Ile Ile Lys Asp Arg Arg Phe Thr Ser
865                 870                 875                 880

Asp Lys Phe Phe Phe His Val Pro Ile Thr Leu Asn Tyr Gln Ala Ala
                885                 890                 895

Asn Ser Pro Ser Lys Phe Asn Gln Arg Val Asn Ala Tyr Leu Lys Glu
            900                 905                 910

His Pro Glu Thr Pro Ile Ile Gly Ile Ala Arg Gly Glu Arg Asn Leu
            915                 920                 925

Ile Tyr Ile Thr Val Ile Asp Ser Thr Gly Lys Ile Leu Glu Gln Arg
            930                 935                 940

Ser Leu Asn Thr Ile Gln Gln Phe Asp Tyr Gln Lys Lys Leu Asp Asn
945                 950                 955                 960

Arg Glu Lys Glu Arg Val Ala Ala Arg Gln Ala Trp Ser Val Val Gly
                965                 970                 975

Thr Ile Lys Asp Leu Lys Gln Gly Tyr Leu Ser Gln Val Ile His Glu
            980                 985                 990

Ile Val Asp Leu Met Ile His Tyr  Gln Ala Val Val Val  Leu Glu Asn
            995                 1000                1005

Leu Asn  Phe Gly Phe Lys Ser  Lys Arg Thr Gly Ile  Ala Glu Lys
        1010                1015                1020

Ala Val  Tyr Gln Gln Phe Glu  Lys Met Leu Ile Asp  Lys Leu Asn
        1025                1030                1035

Cys Leu  Val Leu Lys Asp Tyr  Pro Ala Glu Lys Val  Gly Gly Val
        1040                1045                1050

Leu Asn  Pro Tyr Gln Leu Thr  Asp Gln Phe Thr Ser  Phe Ala Lys
        1055                1060                1065

Met Gly  Thr Gln Ser Gly Phe  Leu Phe Tyr Val Pro  Ala Pro Tyr
        1070                1075                1080

Thr Ser  Lys Ile Asp Pro Leu  Thr Gly Phe Val Asp  Pro Phe Val
        1085                1090                1095

Trp Lys  Thr Ile Lys Asn His  Glu Ser Arg Lys His  Phe Leu Glu
        1100                1105                1110

Gly Phe  Asp Phe Leu His Tyr  Asp Val Lys Thr Gly  Asp Phe Ile
        1115                1120                1125

Leu His  Phe Lys Met Asn Arg  Asn Leu Ser Phe Gln  Arg Gly Leu
        1130                1135                1140

Pro Gly  Phe Met Pro Ala Trp  Asp Ile Val Phe Glu  Lys Asn Glu
        1145                1150                1155

Thr Gln  Phe Asp Ala Lys Gly  Thr Pro Phe Ile Ala  Gly Lys Arg
        1160                1165                1170

Ile Val  Pro Val Ile Glu Asn  His Arg Phe Thr Gly  Arg Tyr Arg
        1175                1180                1185

Asp Leu  Tyr Pro Ala Asn Glu  Leu Ile Ala Leu Leu  Glu Glu Lys
        1190                1195                1200

Gly Ile  Val Phe Arg Asp Gly  Ser Asn Ile Leu Pro  Lys Leu Leu
        1205                1210                1215

Glu Asn  Asp Asp Ser His Ala  Ile Asp Thr Met Val  Ala Leu Ile
        1220                1225                1230

Arg Ser  Val Leu Gln Met Arg  Asn Ser Asn Ala Ala  Thr Gly Glu
```

```
                1235                1240                1245

Asp Tyr Ile Asn Ser Pro Val Arg Asp Leu Asn Gly Val Cys Phe
    1250                1255                1260

Asp Ser Arg Phe Gln Asn Pro Glu Trp Pro Met Asp Ala Asp Ala
    1265                1270                1275

Asn Gly Ala Tyr His Ile Ala Leu Lys Gly Gln Leu Leu Leu Asn
    1280                1285                1290

His Leu Lys Glu Ser Lys Asp Leu Lys Leu Gln Asn Gly Ile Ser
    1295                1300                1305

Asn Gln Asp Trp Leu Ala Tyr Ile Gln Glu Leu Arg Asn Thr Ser
    1310                1315                1320

Arg Ala Asp Pro Lys Lys Lys Arg Lys Val Glu Ala Ser Gly Ser
    1325                1330                1335

Gly Arg Ala Asp Ala Leu Asp Asp Phe Asp Leu Asp Met Leu Gly
    1340                1345                1350

Ser Asp Ala Leu Asp Asp Phe Asp Leu Asp Met Leu Gly Ser Asp
    1355                1360                1365

Ala Leu Asp Asp Phe Asp Leu Asp Met Leu Gly Ser Asp Ala Leu
    1370                1375                1380

Asp Asp Phe Asp Leu Asp Met Leu Ile Asn Ser Arg Ser Gln Tyr
    1385                1390                1395

Leu Pro Asp Thr Asp Asp Arg His Arg Ile Glu Glu Lys Arg Lys
    1400                1405                1410

Arg Thr Tyr Glu Thr Phe Lys Ser Ile Met Lys Lys Ser Pro Phe
    1415                1420                1425

Ser Gly Pro Thr Asp Pro Arg Pro Pro Arg Arg Ile Ala Val
    1430                1435                1440

Pro Ser Arg Ser Ser Ala Ser Val Pro Lys Pro Ala Pro Gln Pro
    1445                1450                1455

Tyr Pro Phe Thr Ser Ser Leu Ser Thr Ile Asn Tyr Asp Glu Phe
    1460                1465                1470

Pro Thr Met Val Phe Pro Ser Gly Gln Ile Ser Gln Ala Ser Ala
    1475                1480                1485

Leu Ala Pro Ala Pro Pro Gln Val Leu Pro Gln Ala Pro Ala Pro
    1490                1495                1500

Ala Pro Ala Pro Ala Met Val Ser Ala Leu Ala Gln Ala Pro Ala
    1505                1510                1515

Pro Val Pro Val Leu Ala Pro Gly Pro Pro Gln Ala Val Ala Pro
    1520                1525                1530

Pro Ala Pro Lys Pro Thr Gln Ala Gly Glu Gly Thr Leu Ser Glu
    1535                1540                1545

Ala Leu Leu Gln Leu Gln Phe Asp Asp Glu Asp Leu Gly Ala Leu
    1550                1555                1560

Leu Gly Asn Ser Thr Asp Pro Ala Val Phe Thr Asp Leu Ala Ser
    1565                1570                1575

Val Asp Asn Ser Glu Phe Gln Gln Leu Leu Asn Gln Gly Ile Pro
    1580                1585                1590

Val Ala Pro His Thr Thr Glu Pro Met Leu Met Glu Tyr Pro Glu
    1595                1600                1605

Ala Ile Thr Arg Leu Val Thr Gly Ala Gln Arg Pro Pro Asp Pro
    1610                1615                1620

Ala Pro Ala Pro Leu Gly Ala Pro Gly Leu Pro Asn Gly Leu Leu
    1625                1630                1635
```

```
Ser Gly Asp Glu Asp Phe Ser Ser Ile Ala Asp Met Asp Phe Ser
    1640                1645                1650

Ala Leu Leu Gly Ser Gly Ser Gly Ser Arg Asp Ser Arg Glu Gly
    1655                1660                1665

Met Phe Leu Pro Lys Pro Glu Ala Gly Ser Ala Ile Ser Asp Val
    1670                1675                1680

Phe Glu Gly Arg Glu Val Cys Gln Pro Lys Arg Ile Arg Pro Phe
    1685                1690                1695

His Pro Pro Gly Ser Pro Trp Ala Asn Arg Pro Leu Pro Ala Ser
    1700                1705                1710

Leu Ala Pro Thr Pro Thr Gly Pro Val His Glu Pro Val Gly Ser
    1715                1720                1725

Leu Thr Pro Ala Pro Val Pro Gln Pro Leu Asp Pro Ala Pro Ala
    1730                1735                1740

Val Thr Pro Glu Ala Ser His Leu Leu Glu Asp Pro Asp Glu Glu
    1745                1750                1755

Thr Ser Gln Ala Val Lys Ala Leu Arg Glu Met Ala Asp Thr Val
    1760                1765                1770

Ile Pro Gln Lys Glu Glu Ala Ala Ile Cys Gly Gln Met Asp Leu
    1775                1780                1785

Ser His Pro Pro Pro Arg Gly His Leu Asp Glu Leu Thr Thr Thr
    1790                1795                1800

Leu Glu Ser Met Thr Glu Asp Leu Asn Leu Asp Ser Pro Leu Thr
    1805                1810                1815

Pro Glu Leu Asn Glu Ile Leu Asp Thr Phe Leu Asn Asp Glu Cys
    1820                1825                1830

Leu Leu His Ala Met His Ile Ser Thr Gly Leu Ser Ile Phe Asp
    1835                1840                1845

Thr Ser Leu Phe
    1850

<210> SEQ ID NO 16
<211> LENGTH: 1654
<212> TYPE: PRT
<213> ORGANISM: Artificial Sequence
<220> FEATURE:
<223> OTHER INFORMATION: Synthetic construct created by rational design

<400> SEQUENCE: 16

Met Pro Lys Lys Lys Arg Lys Val Gly Gly Gly Ser Pro Gly Met Thr
1               5                   10                  15

Gln Phe Glu Gly Phe Thr Asn Leu Tyr Gln Val Ser Lys Thr Leu Arg
                20                  25                  30

Phe Glu Leu Ile Pro Gln Gly Lys Thr Leu Lys His Ile Gln Glu Gln
            35                  40                  45

Gly Phe Ile Glu Glu Asp Lys Ala Arg Asn Asp His Tyr Lys Glu Leu
        50                  55                  60

Lys Pro Ile Ile Asp Arg Ile Tyr Lys Thr Tyr Ala Asp Gln Cys Leu
65                  70                  75                  80

Gln Leu Val Gln Leu Asp Trp Glu Asn Leu Ser Ala Ala Ile Asp Ser
                85                  90                  95

Tyr Arg Lys Glu Lys Thr Glu Glu Thr Arg Asn Ala Leu Ile Glu Glu
                100                 105                 110

Gln Ala Thr Tyr Arg Asn Ala Ile His Asp Tyr Phe Ile Gly Arg Thr
            115                 120                 125
```

```
Asp Asn Leu Thr Asp Ala Ile Asn Lys Arg His Ala Glu Ile Tyr Lys
    130                 135                 140

Gly Leu Phe Lys Ala Glu Leu Phe Asn Gly Lys Val Leu Lys Gln Leu
145                 150                 155                 160

Gly Thr Val Thr Thr Thr Glu His Glu Asn Ala Leu Leu Arg Ser Phe
                165                 170                 175

Asp Lys Phe Thr Thr Tyr Phe Ser Gly Phe Tyr Glu Asn Arg Lys Asn
            180                 185                 190

Val Phe Ser Ala Glu Asp Ile Ser Thr Ala Ile Pro His Arg Ile Val
        195                 200                 205

Gln Asp Asn Phe Pro Lys Phe Lys Glu Asn Cys His Ile Phe Thr Arg
    210                 215                 220

Leu Ile Thr Ala Val Pro Ser Leu Arg Glu His Phe Glu Asn Val Lys
225                 230                 235                 240

Lys Ala Ile Gly Ile Phe Val Ser Thr Ser Ile Glu Glu Val Phe Ser
                245                 250                 255

Phe Pro Phe Tyr Asn Gln Leu Leu Thr Gln Thr Gln Ile Asp Leu Tyr
            260                 265                 270

Asn Gln Leu Leu Gly Gly Ile Ser Arg Glu Ala Gly Thr Glu Lys Ile
        275                 280                 285

Lys Gly Leu Asn Glu Val Leu Asn Leu Ala Ile Gln Lys Asn Asp Glu
    290                 295                 300

Thr Ala His Ile Ile Ala Ser Leu Pro His Arg Phe Ile Pro Leu Phe
305                 310                 315                 320

Lys Gln Ile Leu Ser Asp Arg Asn Thr Leu Ser Phe Ile Leu Glu Glu
                325                 330                 335

Phe Gly Gly Ser Tyr Ser Val Glu Lys Phe Lys Leu Asn Phe Gln
            340                 345                 350

Met Pro Thr Leu Ala Ser Gly Trp Asp Val Asn Lys Glu Lys Asn Asn
        355                 360                 365

Gly Ala Ile Leu Phe Val Lys Asn Gly Leu Tyr Tyr Leu Gly Ile Met
    370                 375                 380

Pro Lys Gln Lys Gly Arg Tyr Lys Ala Leu Ser Phe Glu Pro Thr Glu
385                 390                 395                 400

Lys Thr Ser Glu Gly Phe Asp Lys Met Tyr Tyr Asp Tyr Phe Pro Asp
                405                 410                 415

Ala Ala Lys Met Ile Pro Lys Cys Ser Thr Gln Leu Lys Ala Val Thr
            420                 425                 430

Ala His Phe Gln Thr His Thr Thr Pro Ile Leu Leu Ser Asn Asn Phe
        435                 440                 445

Ile Glu Pro Leu Glu Ile Thr Lys Glu Ile Tyr Asp Leu Asn Asn Pro
    450                 455                 460

Glu Lys Glu Pro Lys Lys Phe Gln Thr Ala Tyr Ala Lys Lys Thr Gly
465                 470                 475                 480

Asp Gln Lys Gly Tyr Arg Glu Ala Leu Cys Lys Trp Ile Asp Phe Thr
                485                 490                 495

Arg Asp Phe Leu Ser Lys Tyr Thr Lys Thr Thr Ser Ile Asp Leu Ser
            500                 505                 510

Ser Leu Arg Pro Ser Ser Gln Tyr Lys Asp Leu Gly Glu Tyr Tyr Ala
        515                 520                 525

Glu Leu Asn Pro Leu Leu Tyr His Ile Ser Phe Gln Arg Ile Ala Glu
    530                 535                 540
```

```
Lys Glu Ile Met Asp Ala Val Glu Thr Gly Lys Leu Tyr Leu Phe Gln
545                 550                 555                 560

Ile Tyr Asn Lys Asp Phe Ala Lys Gly His His Gly Lys Pro Asn Leu
            565                 570                 575

His Thr Leu Tyr Trp Thr Gly Leu Phe Ser Pro Glu Asn Leu Ala Lys
        580                 585                 590

Thr Ser Ile Lys Leu Asn Gly Gln Ala Glu Leu Phe Tyr Arg Pro Lys
    595                 600                 605

Ser Arg Met Lys Arg Met Ala His Arg Leu Gly Glu Lys Met Leu Asn
610                 615                 620

Lys Lys Leu Lys Asp Gln Lys Thr Pro Ile Pro Asp Thr Leu Tyr Gln
625                 630                 635                 640

Glu Leu Tyr Asp Tyr Val Asn His Arg Leu Ser His Asp Leu Ser Asp
            645                 650                 655

Glu Ala Arg Ala Leu Leu Pro Asn Val Ile Thr Lys Glu Val Ser His
                660                 665                 670

Glu Ile Ile Lys Asp Arg Arg Phe Thr Ser Asp Lys Phe Phe Phe His
            675                 680                 685

Val Pro Ile Thr Leu Asn Tyr Gln Ala Ala Asn Ser Pro Ser Lys Phe
690                 695                 700

Asn Gln Arg Val Asn Ala Tyr Leu Lys Glu His Pro Glu Thr Pro Ile
705                 710                 715                 720

Ile Gly Ile Asp Arg Gly Glu Arg Asn Leu Ile Tyr Ile Thr Val Ile
            725                 730                 735

Asp Ser Thr Gly Lys Ile Leu Glu Gln Arg Ser Leu Asn Thr Ile Gln
            740                 745                 750

Gln Phe Asp Tyr Gln Lys Lys Leu Asp Asn Arg Glu Lys Glu Arg Val
    755                 760                 765

Ala Ala Arg Gln Ala Trp Ser Val Val Gly Thr Ile Lys Asp Leu Lys
            770                 775                 780

Gln Gly Tyr Leu Ser Gln Val Ile His Glu Ile Val Asp Leu Met Ile
785                 790                 795                 800

His Tyr Gln Ala Val Val Val Leu Glu Asn Leu Asn Phe Gly Phe Lys
                805                 810                 815

Ser Lys Arg Thr Gly Ile Ala Glu Lys Ala Val Tyr Gln Gln Phe Glu
            820                 825                 830

Lys Met Leu Ile Asp Lys Leu Asn Cys Leu Val Leu Lys Asp Tyr Pro
            835                 840                 845

Ala Glu Lys Val Gly Gly Val Leu Asn Pro Tyr Gln Leu Thr Asp Gln
850                 855                 860

Phe Thr Ser Phe Ala Lys Met Gly Thr Gln Ser Gly Phe Leu Phe Tyr
865                 870                 875                 880

Val Pro Ala Pro Tyr Thr Ser Lys Ile Asp Pro Leu Thr Gly Phe Val
                885                 890                 895

Asp Pro Phe Val Trp Lys Thr Ile Lys Asn His Glu Ser Arg Lys His
            900                 905                 910

Phe Leu Glu Gly Phe Asp Phe Leu His Tyr Asp Val Lys Thr Gly Asp
        915                 920                 925

Phe Ile Leu His Phe Lys Met Asn Arg Asn Leu Ser Phe Gln Arg Gly
            930                 935                 940

Leu Pro Gly Phe Met Pro Ala Trp Asp Ile Val Phe Glu Lys Asn Glu
945                 950                 955                 960

Thr Gln Phe Asp Ala Lys Gly Thr Pro Phe Ile Ala Gly Lys Arg Ile
```

-continued

```
            965                 970                 975
Val Pro Val Ile Glu Asn His Arg Phe Thr Gly Arg Tyr Arg Asp Leu
                980                 985                 990
Tyr Pro Ala Asn Glu Leu Ile Ala Leu Leu Glu Glu Lys Gly Ile Val
            995                 1000                1005
Phe Arg Asp Gly Ser Asn Ile Leu Pro Lys Leu Leu Glu Asn Asp
        1010                1015                1020
Asp Ser His Ala Ile Asp Thr Met Val Ala Leu Ile Arg Ser Val
        1025                1030                1035
Leu Gln Met Arg Asn Ser Asn Ala Ala Thr Gly Glu Asp Tyr Ile
        1040                1045                1050
Asn Ser Pro Val Arg Asp Leu Asn Gly Val Cys Phe Asp Ser Arg
        1055                1060                1065
Phe Gln Asn Pro Glu Trp Pro Met Asp Ala Asp Ala Asn Gly Ala
        1070                1075                1080
Tyr His Ile Ala Leu Lys Gly Gln Leu Leu Asn His Leu Lys
        1085                1090                1095
Glu Ser Lys Asp Leu Lys Leu Gln Asn Gly Ile Ser Asn Gln Asp
        1100                1105                1110
Trp Leu Ala Tyr Ile Gln Glu Leu Arg Asn Thr Ser Arg Ala Asp
        1115                1120                1125
Pro Lys Lys Arg Lys Val Glu Ala Ser Gly Ser Gly Arg Ala
        1130                1135                1140
Asp Ala Leu Asp Asp Phe Asp Leu Asp Met Leu Gly Ser Asp Ala
        1145                1150                1155
Leu Asp Asp Phe Asp Leu Asp Met Leu Gly Ser Asp Ala Leu Asp
        1160                1165                1170
Asp Phe Asp Leu Asp Met Leu Gly Ser Asp Ala Leu Asp Asp Phe
        1175                1180                1185
Asp Leu Asp Met Leu Ile Asn Ser Arg Ser Gln Tyr Leu Pro Asp
        1190                1195                1200
Thr Asp Asp Arg His Arg Ile Glu Glu Lys Arg Lys Arg Thr Tyr
        1205                1210                1215
Glu Thr Phe Lys Ser Ile Met Lys Lys Ser Pro Phe Ser Gly Pro
        1220                1225                1230
Thr Asp Pro Arg Pro Pro Arg Arg Ile Ala Val Pro Ser Arg
        1235                1240                1245
Ser Ser Ala Ser Val Pro Lys Pro Ala Pro Gln Pro Tyr Pro Phe
        1250                1255                1260
Thr Ser Ser Leu Ser Thr Ile Asn Tyr Asp Glu Phe Pro Thr Met
        1265                1270                1275
Val Phe Pro Ser Gly Gln Ile Ser Gln Ala Ser Ala Leu Ala Pro
        1280                1285                1290
Ala Pro Pro Gln Val Leu Pro Gln Ala Pro Ala Pro Ala Pro Ala
        1295                1300                1305
Pro Ala Met Val Ser Ala Leu Ala Gln Ala Pro Ala Pro Val Pro
        1310                1315                1320
Val Leu Ala Pro Gly Pro Pro Gln Ala Val Ala Pro Pro Ala Pro
        1325                1330                1335
Lys Pro Thr Gln Ala Gly Glu Gly Thr Leu Ser Glu Ala Leu Leu
        1340                1345                1350
Gln Leu Gln Phe Asp Asp Glu Asp Leu Gly Ala Leu Leu Gly Asn
        1355                1360                1365
```

Ser Thr Asp Pro Ala Val Phe Thr Asp Leu Ala Ser Val Asp Asn
1370                1375                1380

Ser Glu Phe Gln Gln Leu Leu Asn Gln Gly Ile Pro Val Ala Pro
    1385                1390                1395

His Thr Thr Glu Pro Met Leu Met Glu Tyr Pro Glu Ala Ile Thr
1400                1405                1410

Arg Leu Val Thr Gly Ala Gln Arg Pro Pro Asp Pro Ala Pro Ala
    1415                1420                1425

Pro Leu Gly Ala Pro Gly Leu Pro Asn Gly Leu Leu Ser Gly Asp
1430                1435                1440

Glu Asp Phe Ser Ser Ile Ala Asp Met Asp Phe Ser Ala Leu Leu
    1445                1450                1455

Gly Ser Gly Ser Gly Ser Arg Asp Ser Arg Glu Gly Met Phe Leu
1460                1465                1470

Pro Lys Pro Glu Ala Gly Ser Ala Ile Ser Asp Val Phe Glu Gly
    1475                1480                1485

Arg Glu Val Cys Gln Pro Lys Arg Ile Arg Pro Phe His Pro Pro
1490                1495                1500

Gly Ser Pro Trp Ala Asn Arg Pro Leu Pro Ala Ser Leu Ala Pro
    1505                1510                1515

Thr Pro Thr Gly Pro Val His Glu Pro Val Gly Ser Leu Thr Pro
1520                1525                1530

Ala Pro Val Pro Gln Pro Leu Asp Pro Ala Pro Ala Val Thr Pro
    1535                1540                1545

Glu Ala Ser His Leu Leu Glu Asp Pro Asp Glu Glu Thr Ser Gln
1550                1555                1560

Ala Val Lys Ala Leu Arg Glu Met Ala Asp Thr Val Ile Pro Gln
    1565                1570                1575

Lys Glu Glu Ala Ala Ile Cys Gly Gln Met Asp Leu Ser His Pro
1580                1585                1590

Pro Pro Arg Gly His Leu Asp Glu Leu Thr Thr Thr Leu Glu Ser
    1595                1600                1605

Met Thr Glu Asp Leu Asn Leu Asp Ser Pro Leu Thr Pro Glu Leu
1610                1615                1620

Asn Glu Ile Leu Asp Thr Phe Leu Asn Asp Glu Cys Leu Leu His
    1625                1630                1635

Ala Met His Ile Ser Thr Gly Leu Ser Ile Phe Asp Thr Ser Leu
1640                1645                1650

Phe

<210> SEQ ID NO 17
<211> LENGTH: 977
<212> TYPE: PRT
<213> ORGANISM: Artificial Sequence
<220> FEATURE:
<223> OTHER INFORMATION: Synthetic construct created by rational design

<400> SEQUENCE: 17

Met Pro Lys Lys Lys Arg Lys Val Gly Gly Gly Ser Pro Gly Lys Arg
1               5                   10                  15

Asn Tyr Ile Leu Gly Leu Ala Ile Gly Ile Thr Ser Val Gly Tyr Gly
                20                  25                  30

Ile Ile Asp Tyr Glu Thr Arg Asp Val Ile Asp Ala Gly Val Arg Leu
            35                  40                  45

-continued

```
Phe Lys Glu Ala Asn Val Glu Asn Asn Glu Gly Arg Arg Ser Lys Arg
 50                  55                  60
Gly Ala Arg Arg Leu Lys Arg Arg Arg His Arg Ile Gln Arg Val
 65                  70                  75                  80
Lys Lys Leu Leu Phe Asp Tyr Asn Leu Leu Thr Asp His Ser Glu Leu
                     85                  90                  95
Ser Gly Ile Asn Pro Tyr Glu Ala Arg Val Lys Gly Leu Ser Gln Lys
                100                 105                 110
Leu Ser Glu Glu Glu Phe Ser Ala Leu Leu His Leu Ala Lys Arg
                115                 120                 125
Arg Gly Val His Asn Val Asn Glu Val Glu Glu Asp Thr Gly Asn Glu
130                 135                 140
Leu Ser Thr Lys Glu Gln Ile Ser Arg Asn Ser Lys Ala Leu Glu Glu
145                 150                 155                 160
Lys Tyr Val Ala Glu Leu Gln Leu Glu Arg Leu Lys Lys Asp Gly Glu
                165                 170                 175
Val Arg Gly Ser Ile Asn Arg Phe Lys Thr Ser Asp Tyr Val Lys Glu
                180                 185                 190
Ala Lys Gln Leu Leu Lys Val Gln Lys Ala Tyr His Gln Leu Asp Gln
                195                 200                 205
Ser Phe Ile Asp Thr Tyr Ile Asp Leu Leu Glu Thr Arg Arg Thr Tyr
                210                 215                 220
Tyr Glu Gly Pro Gly Glu Gly Ser Pro Phe Gly Trp Lys Asp Ile Lys
225                 230                 235                 240
Glu Trp Tyr Glu Met Leu Met Gly His Cys Thr Tyr Phe Pro Glu Glu
                245                 250                 255
Leu Arg Ser Val Lys Tyr Ala Tyr Asn Ala Asp Leu Tyr Asn Ala Leu
                260                 265                 270
Asn Asp Leu Asn Asn Leu Val Ile Thr Arg Asp Glu Asn Glu Lys Leu
                275                 280                 285
Glu Tyr Tyr Glu Lys Phe Gln Ile Ile Glu Asn Val Phe Lys Gln Lys
                290                 295                 300
Lys Lys Pro Thr Leu Lys Gln Ile Ala Lys Glu Ile Leu Val Asn Glu
305                 310                 315                 320
Glu Asp Ile Lys Gly Tyr Arg Val Thr Ser Thr Gly Lys Pro Glu Phe
                325                 330                 335
Thr Asn Leu Lys Val Tyr His Asp Ile Lys Asp Ile Thr Ala Arg Lys
                340                 345                 350
Glu Ile Ile Glu Asn Ala Glu Leu Leu Asp Gln Ile Ala Lys Ile Leu
                355                 360                 365
Thr Ile Tyr Gln Ser Ser Glu Asp Ile Gln Glu Glu Leu Thr Asn Leu
                370                 375                 380
Asn Ser Glu Leu Thr Gln Glu Glu Ile Glu Gln Ile Ser Asn Leu Lys
385                 390                 395                 400
Gly Tyr Thr Gly Thr His Asn Leu Ser Leu Lys Ala Ile Asn Leu Ile
                405                 410                 415
Leu Asp Glu Leu Trp His Thr Asn Asp Asn Gln Ile Ala Ile Phe Asn
                420                 425                 430
Arg Leu Lys Leu Val Pro Lys Lys Val Asp Leu Ser Gln Gln Lys Glu
                435                 440                 445
Ile Pro Thr Thr Leu Val Asp Asp Phe Ile Leu Ser Pro Val Val Lys
450                 455                 460
Arg Ser Phe Ile Gln Ser Ile Lys Val Ile Asn Ala Ile Ile Lys Lys
```

```
        465                 470                 475                 480
Tyr Gly Leu Pro Asn Asp Ile Ile Glu Leu Ala Arg Glu Lys Asn
                    485                 490                 495
Ser Lys Asp Ala Gln Lys Met Ile Asn Glu Met Gln Lys Arg Asn Arg
                500                 505                 510
Gln Thr Asn Glu Arg Ile Glu Ile Ile Arg Thr Thr Gly Lys Glu
            515                 520                 525
Asn Ala Lys Tyr Leu Ile Glu Lys Ile Lys Leu His Asp Met Gln Glu
        530                 535                 540
Gly Lys Cys Leu Tyr Ser Leu Glu Ala Ile Pro Leu Glu Asp Leu Leu
545                 550                 555                 560
Asn Asn Pro Phe Asn Tyr Glu Val Asp His Ile Ile Pro Arg Ser Val
                    565                 570                 575
Ser Phe Asp Asn Ser Phe Asn Asn Lys Val Leu Val Lys Gln Glu Glu
                580                 585                 590
Ala Ser Lys Lys Gly Asn Arg Thr Pro Phe Gln Tyr Leu Ser Ser Ser
            595                 600                 605
Asp Ser Lys Ile Ser Tyr Glu Thr Phe Lys Lys His Ile Leu Asn Leu
        610                 615                 620
Ala Lys Gly Lys Gly Arg Ile Ser Lys Thr Lys Lys Glu Tyr Leu Leu
625                 630                 635                 640
Glu Glu Arg Asp Ile Asn Arg Phe Ser Val Gln Lys Asp Phe Ile Asn
                    645                 650                 655
Arg Asn Leu Val Asp Thr Arg Tyr Ala Thr Arg Gly Leu Met Asn Leu
                660                 665                 670
Leu Arg Ser Tyr Phe Arg Val Asn Asn Leu Asp Val Lys Val Lys Ser
            675                 680                 685
Ile Asn Gly Gly Phe Thr Ser Phe Leu Arg Arg Lys Trp Lys Phe Lys
        690                 695                 700
Lys Glu Arg Asn Lys Gly Tyr Lys His His Ala Glu Asp Ala Leu Ile
705                 710                 715                 720
Ile Ala Asn Ala Asp Phe Ile Phe Lys Glu Trp Lys Lys Leu Asp Lys
                    725                 730                 735
Ala Lys Lys Val Met Glu Asn Gln Met Phe Gly Gly Ser Gly Gly
                740                 745                 750
Gly Ser Gly Gly Gly Ser Leu Val Lys Ser Glu Leu Glu Glu Lys Lys
            755                 760                 765
Ser Glu Leu Arg His Lys Leu Lys Tyr Val Pro His Glu Tyr Ile Glu
        770                 775                 780
Leu Ile Glu Ile Ala Arg Asn Ser Thr Gln Asp Arg Ile Leu Glu Met
785                 790                 795                 800
Lys Val Met Glu Phe Phe Met Lys Val Tyr Gly Tyr Arg Gly Lys His
                    805                 810                 815
Leu Gly Gly Ser Arg Lys Pro Asp Gly Ala Ile Tyr Thr Val Gly Ser
                820                 825                 830
Pro Ile Asp Tyr Gly Val Ile Val Asp Thr Lys Ala Tyr Ser Gly Gly
            835                 840                 845
Tyr Asn Leu Pro Ile Gly Gln Ala Asp Glu Met Gln Arg Tyr Val Glu
        850                 855                 860
Glu Asn Gln Thr Arg Asn Lys His Ile Asn Pro Asn Glu Trp Trp Lys
865                 870                 875                 880
Val Tyr Pro Ser Ser Val Thr Glu Phe Lys Phe Leu Phe Val Ser Gly
                    885                 890                 895
```

His Phe Lys Gly Asn Tyr Lys Ala Gln Leu Thr Arg Leu Asn His Ile
                900                 905                 910

Thr Asn Cys Asn Gly Ala Val Leu Ser Val Glu Glu Leu Ile Gly
        915                 920                 925

Gly Glu Met Ile Lys Ala Gly Thr Leu Thr Leu Glu Glu Val Arg Arg
930                 935                 940

Lys Phe Asn Asn Gly Glu Ile Asn Phe Thr Ser Gly Gly Ser Lys
945                 950                 955                 960

Arg Pro Ala Ala Thr Lys Lys Ala Gly Gln Ala Lys Lys Lys Ser
                965                 970                 975

Arg

<210> SEQ ID NO 18
<211> LENGTH: 354
<212> TYPE: PRT
<213> ORGANISM: Artificial Sequence
<220> FEATURE:
<223> OTHER INFORMATION: Synthetic construct created by rational design

<400> SEQUENCE: 18

Met Pro Lys Lys Lys Arg Lys Val Gly Gly Gly Ser Pro Gly Ala Glu
1               5                   10                  15

Ser Met Pro Glu Ile Glu Thr Glu Gln Glu Tyr Lys Glu Ile Phe Ile
                20                  25                  30

Thr Pro His Gln Ile Lys His Ile Lys Asp Phe Lys Asp Tyr Lys Tyr
            35                  40                  45

Ser His Arg Val Asp Lys Lys Pro Asn Arg Lys Leu Ile Asn Asp Thr
    50                  55                  60

Leu Tyr Ser Thr Arg Lys Asp Asp Lys Gly Asn Thr Leu Ile Val Asn
65                  70                  75                  80

Asn Leu Asn Gly Leu Tyr Asp Lys Asp Asn Asp Lys Leu Lys Lys Leu
                85                  90                  95

Ile Asn Lys Ser Pro Glu Lys Leu Leu Met Tyr His His Asp Pro Gln
                100                 105                 110

Thr Tyr Gln Lys Leu Lys Leu Ile Met Glu Gln Tyr Gly Asp Glu Lys
            115                 120                 125

Asn Pro Leu Tyr Lys Tyr Glu Glu Thr Gly Asn Tyr Leu Thr Lys
130                 135                 140

Tyr Ser Lys Lys Asp Asn Gly Pro Val Ile Lys Lys Ile Lys Tyr Tyr
145                 150                 155                 160

Gly Asn Lys Leu Asn Ala His Leu Asp Ile Thr Asp Asp Tyr Pro Asn
                165                 170                 175

Ser Arg Asn Lys Val Val Lys Leu Ser Leu Lys Pro Tyr Arg Phe Asp
                180                 185                 190

Val Tyr Leu Asp Asn Gly Val Tyr Lys Phe Val Thr Val Lys Asn Leu
            195                 200                 205

Asp Val Ile Lys Lys Glu Asn Tyr Tyr Glu Val Asn Ser Lys Cys Tyr
    210                 215                 220

Glu Glu Ala Lys Lys Leu Lys Lys Ile Ser Asn Gln Ala Glu Phe Ile
225                 230                 235                 240

Ala Ser Phe Tyr Lys Asn Asp Leu Ile Lys Ile Asn Gly Glu Leu Tyr
                245                 250                 255

Arg Val Ile Gly Val Asn Asn Asp Leu Leu Asn Arg Ile Glu Val Asn
                260                 265                 270

```
Met Ile Asp Ile Thr Tyr Arg Glu Tyr Leu Glu Asn Met Asn Asp Lys
            275                 280                 285

Arg Pro Pro His Ile Ile Lys Thr Ile Ala Ser Lys Thr Gln Ser Ile
        290                 295                 300

Lys Lys Tyr Ser Thr Asp Ile Leu Gly Asn Leu Tyr Glu Val Lys Ser
305                 310                 315                 320

Lys Lys His Pro Gln Ile Ile Lys Lys Gly Thr Ser Gly Gly Gly Ser
            325                 330                 335

Lys Arg Pro Ala Ala Thr Lys Lys Ala Gly Gln Ala Lys Lys Lys Lys
            340                 345                 350

Ser Arg

<210> SEQ ID NO 19
<211> LENGTH: 809
<212> TYPE: PRT
<213> ORGANISM: Artificial Sequence
<220> FEATURE:
<223> OTHER INFORMATION: Synthetic construct created by rational design

<400> SEQUENCE: 19

Met Pro Lys Lys Lys Arg Lys Val Gly Gly Gly Ser Pro Gly Lys Arg
1               5                   10                  15

Asn Tyr Ile Leu Gly Leu Ala Ile Gly Ile Thr Ser Val Gly Tyr Gly
            20                  25                  30

Ile Ile Asp Tyr Glu Thr Arg Asp Val Ile Asp Ala Gly Val Arg Leu
        35                  40                  45

Phe Lys Glu Ala Asn Val Glu Asn Asn Glu Gly Arg Arg Ser Lys Arg
50                  55                  60

Gly Ala Arg Arg Leu Lys Arg Arg Arg His Arg Ile Gln Arg Val
65                  70                  75                  80

Lys Lys Leu Leu Phe Asp Tyr Asn Leu Leu Thr Asp His Ser Glu Leu
                85                  90                  95

Ser Gly Ile Asn Pro Tyr Glu Ala Arg Val Lys Gly Leu Ser Gln Lys
            100                 105                 110

Leu Ser Glu Glu Glu Phe Ser Ala Ala Leu Leu His Leu Ala Lys Arg
        115                 120                 125

Arg Gly Val His Asn Val Asn Glu Val Glu Glu Asp Thr Gly Asn Glu
    130                 135                 140

Leu Ser Thr Lys Glu Gln Ile Ser Arg Asn Ser Lys Ala Leu Glu Glu
145                 150                 155                 160

Lys Tyr Val Ala Glu Leu Gln Leu Glu Arg Leu Lys Lys Asp Gly Glu
                165                 170                 175

Val Arg Gly Ser Ile Asn Arg Phe Lys Thr Ser Asp Tyr Val Lys Glu
            180                 185                 190

Ala Lys Gln Leu Leu Lys Val Gln Lys Ala Tyr His Gln Leu Asp Gln
        195                 200                 205

Ser Phe Ile Asp Thr Tyr Ile Asp Leu Leu Glu Thr Arg Arg Thr Tyr
    210                 215                 220

Tyr Glu Gly Pro Gly Glu Gly Ser Pro Phe Gly Trp Lys Asp Ile Lys
225                 230                 235                 240

Glu Trp Tyr Glu Met Leu Met Gly His Cys Thr Tyr Phe Pro Glu Glu
                245                 250                 255

Leu Arg Ser Val Lys Tyr Ala Tyr Asn Ala Asp Leu Tyr Asn Ala Leu
            260                 265                 270

Asn Asp Leu Asn Asn Leu Val Ile Thr Arg Asp Glu Asn Glu Lys Leu
```

```
              275                 280                 285
Glu Tyr Tyr Glu Lys Phe Gln Ile Ile Glu Asn Val Phe Lys Gln Lys
290                 295                 300

Lys Lys Pro Thr Leu Lys Gln Ile Ala Lys Glu Ile Leu Val Asn Glu
305                 310                 315                 320

Glu Asp Ile Lys Gly Tyr Arg Val Thr Ser Thr Gly Lys Pro Glu Phe
                325                 330                 335

Thr Asn Leu Lys Val Tyr His Asp Ile Lys Asp Ile Thr Ala Arg Lys
                340                 345                 350

Glu Ile Ile Glu Asn Ala Glu Leu Leu Asp Gln Ile Ala Lys Ile Leu
            355                 360                 365

Thr Ile Tyr Gln Ser Ser Glu Asp Ile Gln Glu Glu Leu Thr Asn Leu
370                 375                 380

Asn Ser Glu Leu Thr Gln Glu Glu Ile Gln Ile Ser Asn Leu Lys
385                 390                 395                 400

Gly Tyr Thr Gly Thr His Asn Leu Ser Leu Lys Ala Ile Asn Leu Ile
                405                 410                 415

Leu Asp Glu Leu Trp His Thr Asn Asp Asn Gln Ile Ala Ile Phe Asn
            420                 425                 430

Arg Leu Lys Leu Val Pro Lys Lys Val Asp Leu Ser Gln Gln Lys Glu
            435                 440                 445

Ile Pro Thr Thr Leu Val Asp Asp Phe Ile Leu Ser Pro Val Val Lys
450                 455                 460

Arg Ser Phe Ile Gln Ser Ile Lys Val Ile Asn Ala Ile Ile Lys Lys
465                 470                 475                 480

Tyr Gly Leu Pro Asn Asp Ile Ile Glu Leu Gly Ser Lys Arg Tyr
                485                 490                 495

Ala Thr Arg Gly Leu Met Asn Leu Leu Arg Ser Tyr Phe Arg Val Asn
            500                 505                 510

Asn Leu Asp Val Lys Val Lys Ser Ile Asn Gly Gly Phe Thr Ser Phe
            515                 520                 525

Leu Arg Arg Lys Trp Lys Phe Lys Lys Glu Arg Asn Lys Gly Tyr Lys
530                 535                 540

His His Ala Glu Asp Ala Leu Ile Ile Ala Asn Ala Asp Phe Ile Phe
545                 550                 555                 560

Lys Glu Trp Lys Lys Leu Asp Lys Ala Lys Lys Val Met Glu Asn Gln
                565                 570                 575

Met Phe Gly Gly Gly Ser Gly Gly Ser Gly Gly Gly Ser Leu Val
                580                 585                 590

Lys Ser Glu Leu Glu Glu Lys Lys Ser Glu Leu Arg His Lys Leu Lys
            595                 600                 605

Tyr Val Pro His Glu Tyr Ile Glu Leu Ile Glu Ile Ala Arg Asn Ser
            610                 615                 620

Thr Gln Asp Arg Ile Leu Glu Met Lys Val Met Glu Phe Phe Met Lys
625                 630                 635                 640

Val Tyr Gly Tyr Arg Gly Lys His Leu Gly Gly Ser Arg Lys Pro Asp
                645                 650                 655

Gly Ala Ile Tyr Thr Val Gly Ser Pro Ile Asp Tyr Gly Val Ile Val
            660                 665                 670

Asp Thr Lys Ala Tyr Ser Gly Gly Tyr Asn Leu Pro Ile Gly Gln Ala
            675                 680                 685

Asp Glu Met Gln Arg Tyr Val Glu Glu Asn Gln Thr Arg Asn Lys His
            690                 695                 700
```

```
Ile Asn Pro Asn Glu Trp Trp Lys Val Tyr Pro Ser Ser Val Thr Glu
705                 710                 715                 720

Phe Lys Phe Leu Phe Val Ser Gly His Phe Lys Gly Asn Tyr Lys Ala
                725                 730                 735

Gln Leu Thr Arg Leu Asn His Ile Thr Asn Cys Asn Gly Ala Val Leu
            740                 745                 750

Ser Val Glu Glu Leu Leu Ile Gly Gly Glu Met Ile Lys Ala Gly Thr
        755                 760                 765

Leu Thr Leu Glu Glu Val Arg Arg Lys Phe Asn Asn Gly Glu Ile Asn
770                 775                 780

Phe Thr Ser Gly Gly Ser Lys Arg Pro Ala Ala Thr Lys Lys Ala
785                 790                 795                 800

Gly Gln Ala Lys Lys Lys Lys Ser Arg
                805
```

<210> SEQ ID NO 20
<211> LENGTH: 1409
<212> TYPE: PRT
<213> ORGANISM: Artificial Sequence
<220> FEATURE:
<223> OTHER INFORMATION: Synthetic construct created by rational design

<400> SEQUENCE: 20

```
Met Pro Lys Lys Arg Lys Val Gly Gly Ser Pro Gly Met Ser
1               5                   10                  15

Ser Glu Thr Gly Pro Val Ala Val Asp Pro Thr Leu Arg Arg Ile
                20                  25                  30

Glu Pro His Glu Phe Glu Val Phe Phe Asp Pro Arg Glu Leu Arg Lys
            35                  40                  45

Glu Thr Cys Leu Leu Tyr Glu Ile Asn Trp Gly Gly Arg His Ser Ile
        50                  55                  60

Trp Arg His Thr Ser Gln Asn Thr Asn Lys His Val Glu Val Asn Phe
65                  70                  75                  80

Ile Glu Lys Phe Thr Thr Glu Arg Tyr Phe Cys Pro Asn Thr Arg Cys
                85                  90                  95

Ser Ile Thr Trp Phe Leu Ser Trp Ser Pro Cys Gly Glu Cys Ser Arg
                100                 105                 110

Ala Ile Thr Glu Phe Leu Ser Arg Tyr Pro His Val Thr Leu Phe Ile
            115                 120                 125

Tyr Ile Ala Arg Leu Tyr His His Ala Asp Pro Arg Asn Arg Gln Gly
        130                 135                 140

Leu Arg Asp Leu Ile Ser Ser Gly Val Thr Ile Gln Ile Met Thr Glu
145                 150                 155                 160

Gln Glu Ser Gly Tyr Cys Trp Arg Asn Phe Val Asn Tyr Ser Pro Ser
                165                 170                 175

Asn Glu Ala His Trp Pro Arg Tyr Pro His Leu Trp Val Arg Leu Tyr
            180                 185                 190

Val Leu Glu Leu Tyr Cys Ile Ile Leu Gly Leu Pro Pro Cys Leu Asn
        195                 200                 205

Ile Leu Arg Arg Lys Gln Pro Gln Leu Thr Phe Phe Thr Ile Ala Leu
210                 215                 220

Gln Ser Cys His Tyr Gln Arg Leu Pro Pro His Ile Leu Trp Ala Thr
225                 230                 235                 240

Gly Leu Lys Ser Gly Ser Glu Thr Pro Gly Thr Ser Glu Ser Ala Thr
                245                 250                 255
```

```
Pro Glu Lys Arg Asn Tyr Ile Leu Gly Leu Ala Ile Gly Ile Thr Ser
            260                 265                 270

Val Gly Tyr Gly Ile Ile Asp Tyr Glu Thr Arg Asp Val Ile Asp Ala
            275                 280                 285

Gly Val Arg Leu Phe Lys Glu Ala Asn Val Glu Asn Asn Glu Gly Arg
            290                 295                 300

Arg Ser Lys Arg Gly Ala Arg Arg Leu Lys Arg Arg Arg His Arg
305                 310                 315                 320

Ile Gln Arg Val Lys Lys Leu Leu Phe Asp Tyr Asn Leu Leu Thr Asp
                325                 330                 335

His Ser Glu Leu Ser Gly Ile Asn Pro Tyr Glu Ala Arg Val Lys Gly
            340                 345                 350

Leu Ser Gln Lys Leu Ser Glu Glu Phe Ser Ala Ala Leu Leu His
            355                 360                 365

Leu Ala Lys Arg Arg Gly Val His Asn Val Asn Glu Val Glu Glu Asp
370                 375                 380

Thr Gly Asn Glu Leu Ser Thr Lys Glu Gln Ile Ser Arg Asn Ser Lys
385                 390                 395                 400

Ala Leu Glu Glu Lys Tyr Val Ala Glu Leu Gln Leu Glu Arg Leu Lys
                405                 410                 415

Lys Asp Gly Glu Val Arg Gly Ser Ile Asn Arg Phe Lys Thr Ser Asp
            420                 425                 430

Tyr Val Lys Glu Ala Lys Gln Leu Leu Lys Val Gln Lys Ala Tyr His
            435                 440                 445

Gln Leu Asp Gln Ser Phe Ile Asp Thr Tyr Ile Asp Leu Leu Glu Thr
450                 455                 460

Arg Arg Thr Tyr Tyr Glu Gly Pro Gly Glu Gly Ser Pro Phe Gly Trp
465                 470                 475                 480

Lys Asp Ile Lys Glu Trp Tyr Glu Met Leu Met Gly His Cys Thr Tyr
                485                 490                 495

Phe Pro Glu Glu Leu Arg Ser Val Lys Tyr Ala Tyr Asn Ala Asp Leu
            500                 505                 510

Tyr Asn Ala Leu Asn Asp Leu Asn Asn Leu Val Ile Thr Arg Asp Glu
            515                 520                 525

Asn Glu Lys Leu Glu Tyr Tyr Glu Lys Phe Gln Ile Ile Glu Asn Val
            530                 535                 540

Phe Lys Gln Lys Lys Lys Pro Thr Leu Lys Gln Ile Ala Lys Glu Ile
545                 550                 555                 560

Leu Val Asn Glu Glu Asp Ile Lys Gly Tyr Arg Val Thr Ser Thr Gly
                565                 570                 575

Lys Pro Glu Phe Thr Asn Leu Lys Val Tyr His Asp Ile Lys Asp Ile
            580                 585                 590

Thr Ala Arg Lys Glu Ile Ile Glu Asn Ala Glu Leu Leu Asp Gln Ile
            595                 600                 605

Ala Lys Ile Leu Thr Ile Tyr Gln Ser Ser Glu Asp Ile Gln Glu Glu
            610                 615                 620

Leu Thr Asn Leu Asn Ser Glu Leu Thr Gln Glu Ile Glu Gln Ile
625                 630                 635                 640

Ser Asn Leu Lys Gly Tyr Thr Gly Thr His Asn Leu Ser Leu Lys Ala
                645                 650                 655

Ile Asn Leu Ile Leu Asp Glu Leu Trp His Thr Asn Asp Asn Gln Ile
            660                 665                 670
```

```
Ala Ile Phe Asn Arg Leu Lys Leu Val Pro Lys Lys Val Asp Leu Ser
            675                 680                 685

Gln Gln Lys Glu Ile Pro Thr Thr Leu Val Asp Asp Phe Ile Leu Ser
690                 695                 700

Pro Val Val Lys Arg Ser Phe Ile Gln Ser Ile Lys Val Ile Asn Ala
705                 710                 715                 720

Ile Ile Lys Lys Tyr Gly Leu Pro Asn Asp Ile Ile Glu Leu Ala
            725                 730                 735

Arg Glu Lys Asn Ser Lys Asp Ala Gln Lys Met Ile Asn Glu Met Gln
            740                 745                 750

Lys Arg Asn Arg Gln Thr Asn Glu Arg Ile Glu Glu Ile Ile Arg Thr
            755                 760                 765

Thr Gly Lys Glu Asn Ala Lys Tyr Leu Ile Glu Lys Ile Lys Leu His
            770                 775                 780

Asp Met Gln Glu Gly Lys Cys Leu Tyr Ser Leu Glu Ala Ile Pro Leu
785                 790                 795                 800

Glu Asp Leu Leu Asn Asn Pro Phe Asn Tyr Glu Val Asp His Ile Ile
            805                 810                 815

Pro Arg Ser Val Ser Phe Asp Asn Ser Phe Asn Asn Lys Val Leu Val
            820                 825                 830

Lys Gln Glu Glu Ala Ser Lys Lys Gly Asn Arg Thr Pro Phe Gln Tyr
            835                 840                 845

Leu Ser Ser Ser Asp Ser Lys Ile Ser Tyr Glu Thr Phe Lys Lys His
            850                 855                 860

Ile Leu Asn Leu Ala Lys Gly Lys Gly Arg Ile Ser Lys Thr Lys Lys
865                 870                 875                 880

Glu Tyr Leu Leu Glu Glu Arg Asp Ile Asn Arg Phe Ser Val Gln Lys
            885                 890                 895

Asp Phe Ile Asn Arg Asn Leu Val Asp Thr Arg Tyr Ala Thr Arg Gly
            900                 905                 910

Leu Met Asn Leu Leu Arg Ser Tyr Phe Arg Val Asn Asn Leu Asp Val
            915                 920                 925

Lys Val Lys Ser Ile Asn Gly Gly Phe Thr Ser Phe Leu Arg Arg Lys
930                 935                 940

Trp Lys Phe Lys Lys Glu Arg Asn Lys Gly Tyr Lys His His Ala Glu
945                 950                 955                 960

Asp Ala Leu Ile Ile Ala Asn Ala Asp Phe Ile Phe Lys Glu Trp Lys
            965                 970                 975

Lys Leu Asp Lys Ala Lys Lys Val Met Glu Asn Gln Met Phe Glu Glu
            980                 985                 990

Lys Gln Ala Glu Ser Met Pro Glu Ile Glu Thr Glu Gln Glu Tyr Lys
            995                 1000                1005

Glu Ile Phe Ile Thr Pro His Gln Ile Lys His Ile Lys Asp Phe
            1010                1015                1020

Lys Asp Tyr Lys Tyr Ser His Arg Val Asp Lys Lys Pro Asn Arg
            1025                1030                1035

Lys Leu Ile Asn Asp Thr Leu Tyr Ser Thr Arg Lys Asp Asp Lys
            1040                1045                1050

Gly Asn Thr Leu Ile Val Asn Asn Leu Asn Gly Leu Tyr Asp Lys
            1055                1060                1065

Asp Asn Asp Lys Leu Lys Lys Leu Ile Asn Lys Ser Pro Glu Lys
            1070                1075                1080

Leu Leu Met Tyr His His Asp Pro Gln Thr Tyr Gln Lys Leu Lys
```

```
                        1085                1090                1095

Leu Ile Met Glu Gln Tyr Gly Asp Glu Lys Asn Pro Leu Tyr Lys
            1100                1105                1110

Tyr Tyr Glu Glu Thr Gly Asn Tyr Leu Thr Lys Tyr Ser Lys Lys
            1115                1120                1125

Asp Asn Gly Pro Val Ile Lys Lys Ile Lys Tyr Tyr Gly Asn Lys
            1130                1135                1140

Leu Asn Ala His Leu Asp Ile Thr Asp Asp Tyr Pro Asn Ser Arg
            1145                1150                1155

Asn Lys Val Val Lys Leu Ser Leu Lys Pro Tyr Arg Phe Asp Val
            1160                1165                1170

Tyr Leu Asp Asn Gly Val Tyr Lys Phe Val Thr Val Lys Asn Leu
            1175                1180                1185

Asp Val Ile Lys Lys Glu Asn Tyr Tyr Glu Val Asn Ser Lys Cys
            1190                1195                1200

Tyr Glu Glu Ala Lys Lys Leu Lys Lys Ile Ser Asn Gln Ala Glu
            1205                1210                1215

Phe Ile Ala Ser Phe Tyr Lys Asn Asp Leu Ile Lys Ile Asn Gly
            1220                1225                1230

Glu Leu Tyr Arg Val Ile Gly Val Asn Asn Asp Leu Leu Asn Arg
            1235                1240                1245

Ile Glu Val Asn Met Ile Asp Ile Thr Tyr Arg Glu Tyr Leu Glu
            1250                1255                1260

Asn Met Asn Asp Lys Arg Pro Pro His Ile Ile Lys Thr Ile Ala
            1265                1270                1275

Ser Lys Thr Gln Ser Ile Lys Lys Tyr Ser Thr Asp Ile Leu Gly
            1280                1285                1290

Asn Leu Tyr Glu Val Lys Ser Lys Lys His Pro Gln Ile Ile Lys
            1295                1300                1305

Lys Gly Ser Gly Gly Ser Thr Asn Leu Ser Asp Ile Ile Glu Lys
            1310                1315                1320

Glu Thr Gly Lys Gln Leu Val Ile Gln Glu Ser Ile Leu Met Leu
            1325                1330                1335

Pro Glu Glu Val Glu Glu Val Ile Gly Asn Lys Pro Glu Ser Asp
            1340                1345                1350

Ile Leu Val His Thr Ala Tyr Asp Glu Ser Thr Asp Glu Asn Val
            1355                1360                1365

Met Leu Leu Thr Ser Asp Ala Pro Glu Tyr Lys Pro Trp Ala Leu
            1370                1375                1380

Val Ile Gln Asp Ser Asn Gly Glu Asn Lys Ile Lys Met Leu Ser
            1385                1390                1395

Gly Gly Ser Pro Pro Lys Lys Lys Arg Lys Val
            1400                1405

<210> SEQ ID NO 21
<211> LENGTH: 1241
<212> TYPE: PRT
<213> ORGANISM: Artificial Sequence
<220> FEATURE:
<223> OTHER INFORMATION: Synthetic construct created by rational design

<400> SEQUENCE: 21

Met Pro Lys Lys Arg Lys Val Gly Gly Gly Ser Pro Gly Met Ser
1               5                   10                  15

Ser Glu Thr Gly Pro Val Ala Val Asp Pro Thr Leu Arg Arg Arg Ile
```

-continued

```
            20                  25                  30
Glu Pro His Glu Phe Glu Val Phe Asp Pro Arg Glu Leu Arg Lys
                35                  40                  45
Glu Thr Cys Leu Leu Tyr Glu Ile Asn Trp Gly Gly Arg His Ser Ile
 50                  55                  60
Trp Arg His Thr Ser Gln Asn Thr Asn Lys His Val Glu Val Asn Phe
 65                  70                  75                  80
Ile Glu Lys Phe Thr Thr Glu Arg Tyr Phe Cys Pro Asn Thr Arg Cys
                85                  90                  95
Ser Ile Thr Trp Phe Leu Ser Trp Ser Pro Cys Gly Glu Cys Ser Arg
                100                 105                 110
Ala Ile Thr Glu Phe Leu Ser Arg Tyr Pro His Val Thr Leu Phe Ile
                115                 120                 125
Tyr Ile Ala Arg Leu Tyr His His Ala Asp Pro Arg Asn Arg Gln Gly
                130                 135                 140
Leu Arg Asp Leu Ile Ser Ser Gly Val Thr Ile Gln Ile Met Thr Glu
145                 150                 155                 160
Gln Glu Ser Gly Tyr Cys Trp Arg Asn Phe Val Asn Tyr Ser Pro Ser
                165                 170                 175
Asn Glu Ala His Trp Pro Arg Tyr Pro His Leu Trp Val Arg Leu Tyr
                180                 185                 190
Val Leu Glu Leu Tyr Cys Ile Ile Leu Gly Leu Pro Pro Cys Leu Asn
                195                 200                 205
Ile Leu Arg Arg Lys Gln Pro Gln Leu Thr Phe Phe Thr Ile Ala Leu
                210                 215                 220
Gln Ser Cys His Tyr Gln Arg Leu Pro Pro His Ile Leu Trp Ala Thr
225                 230                 235                 240
Gly Leu Lys Ser Gly Ser Glu Thr Pro Gly Thr Ser Glu Ser Ala Thr
                245                 250                 255
Pro Glu Lys Arg Asn Tyr Ile Leu Gly Leu Ala Ile Gly Ile Thr Ser
                260                 265                 270
Val Gly Tyr Gly Ile Ile Asp Tyr Glu Thr Arg Asp Val Ile Asp Ala
                275                 280                 285
Gly Val Arg Leu Phe Lys Glu Ala Asn Val Glu Asn Asn Glu Gly Arg
                290                 295                 300
Arg Ser Lys Arg Gly Ala Arg Arg Leu Lys Arg Arg Arg His Arg
305                 310                 315                 320
Ile Gln Arg Val Lys Lys Leu Leu Phe Asp Tyr Asn Leu Leu Thr Asp
                325                 330                 335
His Ser Glu Leu Ser Gly Ile Asn Pro Tyr Glu Ala Arg Val Lys Gly
                340                 345                 350
Leu Ser Gln Lys Leu Ser Glu Glu Phe Ser Ala Ala Leu Leu His
                355                 360                 365
Leu Ala Lys Arg Arg Gly Val His Asn Val Asn Glu Val Glu Glu Asp
                370                 375                 380
Thr Gly Asn Glu Leu Ser Thr Lys Glu Gln Ile Ser Arg Asn Ser Lys
385                 390                 395                 400
Ala Leu Glu Glu Lys Tyr Val Ala Glu Leu Gln Leu Glu Arg Leu Lys
                405                 410                 415
Lys Asp Gly Glu Val Arg Gly Ser Ile Asn Arg Phe Lys Thr Ser Asp
                420                 425                 430
Tyr Val Lys Glu Ala Lys Gln Leu Leu Lys Val Gln Lys Ala Tyr His
                435                 440                 445
```

```
Gln Leu Asp Gln Ser Phe Ile Asp Thr Tyr Ile Asp Leu Leu Glu Thr
    450                 455                 460

Arg Arg Thr Tyr Tyr Glu Gly Pro Gly Glu Gly Ser Pro Phe Gly Trp
465                 470                 475                 480

Lys Asp Ile Lys Glu Trp Tyr Glu Met Leu Met Gly His Cys Thr Tyr
                485                 490                 495

Phe Pro Glu Glu Leu Arg Ser Val Lys Tyr Ala Tyr Asn Ala Asp Leu
            500                 505                 510

Tyr Asn Ala Leu Asn Asp Leu Asn Asn Leu Val Ile Thr Arg Asp Glu
        515                 520                 525

Asn Glu Lys Leu Glu Tyr Tyr Glu Lys Phe Gln Ile Ile Glu Asn Val
    530                 535                 540

Phe Lys Gln Lys Lys Lys Pro Thr Leu Lys Gln Ile Ala Lys Glu Ile
545                 550                 555                 560

Leu Val Asn Glu Glu Asp Ile Lys Gly Tyr Arg Val Thr Ser Thr Gly
                565                 570                 575

Lys Pro Glu Phe Thr Asn Leu Lys Val Tyr His Asp Ile Lys Asp Ile
            580                 585                 590

Thr Ala Arg Lys Glu Ile Ile Glu Asn Ala Glu Leu Leu Asp Gln Ile
        595                 600                 605

Ala Lys Ile Leu Thr Ile Tyr Gln Ser Ser Glu Asp Ile Gln Glu Glu
    610                 615                 620

Leu Thr Asn Leu Asn Ser Glu Leu Thr Gln Glu Glu Ile Glu Gln Ile
625                 630                 635                 640

Ser Asn Leu Lys Gly Tyr Thr Gly Thr His Asn Leu Ser Leu Lys Ala
                645                 650                 655

Ile Asn Leu Ile Leu Asp Glu Leu Trp His Thr Asn Asp Asn Gln Ile
            660                 665                 670

Ala Ile Phe Asn Arg Leu Lys Leu Val Pro Lys Lys Val Asp Leu Ser
        675                 680                 685

Gln Gln Lys Glu Ile Pro Thr Thr Leu Val Asp Asp Phe Ile Leu Ser
    690                 695                 700

Pro Val Val Lys Arg Ser Phe Ile Gln Ser Ile Lys Val Ile Asn Ala
705                 710                 715                 720

Ile Ile Lys Lys Tyr Gly Leu Pro Asn Asp Ile Ile Glu Leu Gly
                725                 730                 735

Ser Lys Arg Tyr Ala Thr Arg Gly Leu Met Asn Leu Leu Arg Ser Tyr
            740                 745                 750

Phe Arg Val Asn Asn Leu Asp Val Lys Val Lys Ser Ile Asn Gly Gly
        755                 760                 765

Phe Thr Ser Phe Leu Arg Arg Lys Trp Lys Phe Lys Lys Glu Arg Asn
    770                 775                 780

Lys Gly Tyr Lys His His Ala Glu Asp Ala Leu Ile Ile Ala Asn Ala
785                 790                 795                 800

Asp Phe Ile Phe Lys Glu Trp Lys Lys Leu Asp Lys Ala Lys Lys Val
                805                 810                 815

Met Glu Asn Gln Met Phe Glu Glu Lys Gln Ala Glu Ser Met Pro Glu
            820                 825                 830

Ile Glu Thr Glu Gln Glu Tyr Lys Glu Ile Phe Ile Thr Pro His Gln
        835                 840                 845

Ile Lys His Ile Lys Asp Phe Lys Asp Tyr Lys Tyr Ser His Arg Val
    850                 855                 860
```

-continued

Asp Lys Lys Pro Asn Arg Lys Leu Ile Asn Asp Thr Leu Tyr Ser Thr
865                 870                 875                 880

Arg Lys Asp Asp Lys Gly Asn Thr Leu Ile Val Asn Asn Leu Asn Gly
            885                 890                 895

Leu Tyr Asp Lys Asp Asn Asp Lys Leu Lys Lys Leu Ile Asn Lys Ser
        900                 905                 910

Pro Glu Lys Leu Leu Met Tyr His His Asp Pro Gln Thr Tyr Gln Lys
    915                 920                 925

Leu Lys Leu Ile Met Glu Gln Tyr Gly Asp Glu Lys Asn Pro Leu Tyr
930                 935                 940

Lys Tyr Tyr Glu Glu Thr Gly Asn Tyr Leu Thr Lys Tyr Ser Lys Lys
945                 950                 955                 960

Asp Asn Gly Pro Val Ile Lys Lys Ile Lys Tyr Tyr Gly Asn Lys Leu
            965                 970                 975

Asn Ala His Leu Asp Ile Thr Asp Asp Tyr Pro Asn Ser Arg Asn Lys
        980                 985                 990

Val Val Lys Leu Ser Leu Lys Pro Tyr Arg Phe Asp Val Tyr Leu Asp
    995                 1000                1005

Asn Gly Val Tyr Lys Phe Val Thr Val Lys Asn Leu Asp Val Ile
    1010                1015                1020

Lys Lys Glu Asn Tyr Tyr Glu Val Asn Ser Lys Cys Tyr Glu Glu
    1025                1030                1035

Ala Lys Lys Leu Lys Lys Ile Ser Asn Gln Ala Glu Phe Ile Ala
    1040                1045                1050

Ser Phe Tyr Lys Asn Asp Leu Ile Lys Ile Asn Gly Glu Leu Tyr
    1055                1060                1065

Arg Val Ile Gly Val Asn Asn Asp Leu Leu Asn Arg Ile Glu Val
    1070                1075                1080

Asn Met Ile Asp Ile Thr Tyr Arg Glu Tyr Leu Glu Asn Met Asn
    1085                1090                1095

Asp Lys Arg Pro Pro His Ile Ile Lys Thr Ile Ala Ser Lys Thr
    1100                1105                1110

Gln Ser Ile Lys Lys Tyr Ser Thr Asp Ile Leu Gly Asn Leu Tyr
    1115                1120                1125

Glu Val Lys Ser Lys Lys His Pro Gln Ile Ile Lys Lys Gly Ser
    1130                1135                1140

Gly Gly Ser Thr Asn Leu Ser Asp Ile Ile Glu Lys Glu Thr Gly
    1145                1150                1155

Lys Gln Leu Val Ile Gln Glu Ser Ile Leu Met Leu Pro Glu Glu
    1160                1165                1170

Val Glu Glu Val Ile Gly Asn Lys Pro Glu Ser Asp Ile Leu Val
    1175                1180                1185

His Thr Ala Tyr Asp Glu Ser Thr Asp Glu Asn Val Met Leu Leu
    1190                1195                1200

Thr Ser Asp Ala Pro Glu Tyr Lys Pro Trp Ala Leu Val Ile Gln
    1205                1210                1215

Asp Ser Asn Gly Glu Asn Lys Ile Lys Met Leu Ser Gly Gly Ser
    1220                1225                1230

Pro Pro Lys Lys Lys Arg Lys Val
    1235                1240

<210> SEQ ID NO 22
<211> LENGTH: 771
<212> TYPE: PRT

<213> ORGANISM: Artificial Sequence
<220> FEATURE:
<223> OTHER INFORMATION: Synthetic construct created by rational design

<400> SEQUENCE: 22

```
Met Pro Lys Lys Lys Arg Lys Val Gly Gly Gly Ser Pro Gly Lys Arg
1               5                   10                  15

Asn Tyr Ile Leu Gly Leu Ala Ile Gly Ile Thr Ser Val Gly Tyr Gly
            20                  25                  30

Ile Ile Asp Tyr Glu Thr Arg Asp Val Ile Asp Ala Gly Val Arg Leu
        35                  40                  45

Phe Lys Glu Ala Asn Val Glu Asn Asn Glu Gly Arg Arg Ser Lys Arg
    50                  55                  60

Gly Ala Arg Arg Leu Lys Arg Arg Arg His Arg Ile Gln Arg Val
65                  70                  75                  80

Lys Lys Leu Leu Phe Asp Tyr Asn Leu Leu Thr Asp His Ser Glu Leu
                85                  90                  95

Ser Gly Ile Asn Pro Tyr Glu Ala Arg Val Lys Gly Leu Ser Gln Lys
            100                 105                 110

Leu Ser Glu Glu Glu Phe Ser Ala Ala Leu Leu His Leu Ala Lys Arg
        115                 120                 125

Arg Gly Val His Asn Val Asn Glu Val Glu Glu Asp Thr Gly Asn Glu
    130                 135                 140

Leu Ser Thr Lys Glu Gln Ile Ser Arg Asn Ser Lys Ala Leu Glu Glu
145                 150                 155                 160

Lys Tyr Val Ala Glu Leu Gln Leu Glu Arg Leu Lys Lys Asp Gly Glu
                165                 170                 175

Val Arg Gly Ser Ile Asn Arg Phe Lys Thr Ser Asp Tyr Val Lys Glu
            180                 185                 190

Ala Lys Gln Leu Leu Lys Val Gln Lys Ala Tyr His Gln Leu Asp Gln
        195                 200                 205

Ser Phe Ile Asp Thr Tyr Ile Asp Leu Leu Glu Thr Arg Arg Thr Tyr
    210                 215                 220

Tyr Glu Gly Pro Gly Glu Gly Ser Pro Phe Gly Trp Lys Asp Ile Lys
225                 230                 235                 240

Glu Trp Tyr Glu Met Leu Met Gly His Cys Thr Tyr Phe Pro Glu Glu
                245                 250                 255

Leu Arg Ser Val Lys Tyr Ala Tyr Asn Ala Asp Leu Tyr Asn Ala Leu
            260                 265                 270

Asn Asp Leu Asn Asn Leu Val Ile Thr Arg Asp Glu Asn Glu Lys Leu
        275                 280                 285

Glu Tyr Tyr Glu Lys Phe Gln Ile Ile Glu Asn Val Phe Lys Gln Lys
    290                 295                 300

Lys Lys Pro Thr Leu Lys Gln Ile Ala Lys Glu Ile Leu Val Asn Glu
305                 310                 315                 320

Glu Asp Ile Lys Gly Tyr Arg Val Thr Ser Thr Gly Lys Pro Glu Phe
                325                 330                 335

Thr Asn Leu Lys Val Tyr His Asp Ile Lys Asp Ile Thr Ala Arg Lys
            340                 345                 350

Glu Ile Ile Glu Asn Ala Glu Leu Leu Asp Gln Ile Ala Lys Ile Leu
        355                 360                 365

Thr Ile Tyr Gln Ser Ser Glu Asp Ile Gln Glu Glu Leu Thr Asn Leu
    370                 375                 380

Asn Ser Glu Leu Thr Gln Glu Glu Ile Glu Gln Ile Ser Asn Leu Lys
```

```
            385                 390                 395                 400
Gly Tyr Thr Gly Thr His Asn Leu Ser Leu Lys Ala Ile Asn Leu Ile
                    405                 410                 415

Leu Asp Glu Leu Trp His Thr Asn Asp Asn Gln Ile Ala Ile Phe Asn
                    420                 425                 430

Arg Leu Lys Leu Val Pro Lys Val Asp Leu Ser Gln Gln Lys Glu
                    435                 440                 445

Ile Pro Thr Thr Leu Val Asp Asp Phe Ile Leu Ser Pro Val Val Lys
            450                 455                 460

Arg Ser Phe Ile Gln Ser Ile Lys Val Ile Asn Ala Ile Ile Lys Lys
465                 470                 475                 480

Tyr Gly Leu Pro Asn Asp Ile Ile Glu Leu Ala Arg Glu Lys Gly
                    485                 490                 495

Gly Gly Ser Gly Gly Ser Met Ser Ser Glu Thr Gly Pro Val Ala
                500                 505                 510

Val Asp Pro Thr Leu Arg Arg Arg Ile Glu Pro His Glu Phe Glu Val
            515                 520                 525

Phe Phe Asp Pro Arg Glu Leu Arg Lys Glu Thr Cys Leu Leu Tyr Glu
            530                 535                 540

Ile Asn Trp Gly Gly Arg His Ser Ile Trp Arg His Thr Ser Gln Asn
545                 550                 555                 560

Thr Asn Lys His Val Glu Val Asn Phe Ile Glu Lys Phe Thr Thr Glu
                    565                 570                 575

Arg Tyr Phe Cys Pro Asn Thr Arg Cys Ser Ile Thr Trp Phe Leu Ser
                580                 585                 590

Trp Ser Pro Cys Gly Glu Cys Ser Arg Ala Ile Thr Glu Phe Leu Ser
            595                 600                 605

Arg Tyr Pro His Val Thr Leu Phe Ile Tyr Ile Ala Arg Leu Tyr His
            610                 615                 620

His Ala Asp Pro Arg Asn Arg Gln Gly Leu Arg Asp Leu Ile Ser Ser
625                 630                 635                 640

Gly Val Thr Ile Gln Ile Met Thr Glu Gln Glu Ser Gly Tyr Cys Trp
                    645                 650                 655

Arg Asn Phe Val Asn Tyr Ser Pro Ser Asn Glu Ala His Trp Pro Arg
                660                 665                 670

Tyr Pro His Leu Trp Val Arg Leu Tyr Val Leu Glu Leu Tyr Cys Ile
            675                 680                 685

Ile Leu Gly Leu Pro Pro Cys Leu Asn Ile Leu Arg Arg Lys Gln Pro
            690                 695                 700

Gln Leu Thr Phe Phe Thr Ile Ala Leu Gln Ser Cys His Tyr Gln Arg
705                 710                 715                 720

Leu Pro Pro His Ile Leu Trp Ala Thr Gly Leu Lys Ser Gly Ser Glu
                    725                 730                 735

Thr Pro Gly Thr Ser Glu Ser Ala Thr Pro Glu Thr Ser Gly Gly Gly
                    740                 745                 750

Ser Lys Arg Pro Ala Ala Thr Lys Lys Ala Gly Gln Ala Lys Lys Lys
                755                 760                 765

Lys Ser Arg
        770

<210> SEQ ID NO 23
<211> LENGTH: 518
<212> TYPE: PRT
<213> ORGANISM: Artificial Sequence
```

<220> FEATURE:
<223> OTHER INFORMATION: Synthetic construct created by rational design

<400> SEQUENCE: 23

Met Pro Lys Lys Lys Arg Lys Val Gly Gly Gly Ser Pro Gly Thr Arg
1               5                   10                  15

Tyr Ala Thr Arg Gly Leu Met Asn Leu Leu Arg Ser Tyr Phe Arg Val
                20                  25                  30

Asn Asn Leu Asp Val Lys Val Lys Ser Ile Asn Gly Gly Phe Thr Ser
            35                  40                  45

Phe Leu Arg Arg Lys Trp Lys Phe Lys Glu Arg Asn Lys Gly Tyr
    50                  55                  60

Lys His His Ala Glu Asp Ala Leu Ile Ile Ala Asn Ala Asp Phe Ile
65                  70                  75                  80

Phe Lys Glu Trp Lys Lys Leu Asp Lys Ala Lys Lys Val Met Glu Asn
                85                  90                  95

Gln Met Phe Glu Glu Lys Gln Ala Glu Ser Met Pro Glu Ile Glu Thr
                100                 105                 110

Glu Gln Glu Tyr Lys Glu Ile Phe Ile Thr Pro His Gln Ile Lys His
            115                 120                 125

Ile Lys Asp Phe Lys Asp Tyr Lys Tyr Ser His Arg Val Asp Lys Lys
130                 135                 140

Pro Asn Arg Lys Leu Ile Asn Asp Thr Leu Tyr Ser Thr Arg Lys Asp
145                 150                 155                 160

Asp Lys Gly Asn Thr Leu Ile Val Asn Asn Leu Asn Gly Leu Tyr Asp
                165                 170                 175

Lys Asp Asn Asp Lys Leu Lys Lys Leu Ile Asn Lys Ser Pro Glu Lys
            180                 185                 190

Leu Leu Met Tyr His His Asp Pro Gln Thr Tyr Gln Lys Leu Lys Leu
        195                 200                 205

Ile Met Glu Gln Tyr Gly Asp Glu Lys Asn Pro Leu Tyr Lys Tyr Tyr
    210                 215                 220

Glu Glu Thr Gly Asn Tyr Leu Thr Lys Tyr Ser Lys Lys Asp Asn Gly
225                 230                 235                 240

Pro Val Ile Lys Lys Ile Lys Tyr Tyr Gly Asn Lys Leu Asn Ala His
                245                 250                 255

Leu Asp Ile Thr Asp Asp Tyr Pro Asn Ser Arg Asn Lys Val Val Lys
            260                 265                 270

Leu Ser Leu Lys Pro Tyr Arg Phe Asp Val Tyr Leu Asp Asn Gly Val
        275                 280                 285

Tyr Lys Phe Val Thr Val Lys Asn Leu Asp Val Ile Lys Lys Glu Asn
    290                 295                 300

Tyr Tyr Glu Val Asn Ser Lys Cys Tyr Glu Ala Lys Lys Leu Lys
305                 310                 315                 320

Lys Ile Ser Asn Gln Ala Glu Phe Ile Ala Ser Phe Tyr Lys Asn Asp
                325                 330                 335

Leu Ile Lys Ile Asn Gly Glu Leu Tyr Arg Val Ile Gly Val Asn Asn
            340                 345                 350

Asp Leu Leu Asn Arg Ile Glu Val Asn Met Ile Asp Ile Thr Tyr Arg
        355                 360                 365

Glu Tyr Leu Glu Asn Met Asn Asp Lys Arg Pro Pro His Ile Ile Lys
    370                 375                 380

Thr Ile Ala Ser Lys Thr Gln Ser Ile Lys Lys Tyr Ser Thr Asp Ile
385                 390                 395                 400

```
Leu Gly Asn Leu Tyr Glu Val Lys Ser Lys Lys His Pro Gln Ile Ile
            405                 410                 415

Lys Lys Gly Ser Gly Gly Ser Thr Asn Leu Ser Asp Ile Ile Glu Lys
            420                 425                 430

Glu Thr Gly Lys Gln Leu Val Ile Gln Glu Ser Ile Leu Met Leu Pro
            435                 440                 445

Glu Glu Val Glu Glu Val Ile Gly Asn Lys Pro Glu Ser Asp Ile Leu
        450                 455                 460

Val His Thr Ala Tyr Asp Glu Ser Thr Asp Glu Asn Val Met Leu Leu
465                 470                 475                 480

Thr Ser Asp Ala Pro Glu Tyr Lys Pro Trp Ala Leu Val Ile Gln Asp
                485                 490                 495

Ser Asn Gly Glu Asn Lys Ile Lys Met Leu Ser Gly Gly Ser Pro Pro
            500                 505                 510

Lys Lys Lys Arg Lys Val
            515

<210> SEQ ID NO 24
<211> LENGTH: 391
<212> TYPE: PRT
<213> ORGANISM: Artificial Sequence
<220> FEATURE:
<223> OTHER INFORMATION: Synthetic construct created by rational design

<400> SEQUENCE: 24

Gly Ser Gly Arg Ala Asp Ala Leu Asp Asp Phe Asp Leu Asp Met Leu
1               5                   10                  15

Gly Ser Asp Ala Leu Asp Asp Phe Asp Leu Asp Met Leu Gly Ser Asp
            20                  25                  30

Ala Leu Asp Asp Phe Asp Leu Asp Met Leu Gly Ser Asp Ala Leu Asp
        35                  40                  45

Asp Phe Asp Leu Asp Met Leu Ile Asn Ser Ala Leu Leu Gln Leu Gln
    50                  55                  60

Phe Asp Asp Glu Asp Leu Gly Ala Leu Leu Gly Asn Ser Thr Asp Pro
65                  70                  75                  80

Ala Val Phe Thr Asp Leu Ala Ser Val Asp Asn Ser Glu Phe Gln Gln
                85                  90                  95

Leu Leu Asn Gln Gly Ile Pro Val Ala Pro His Thr Thr Glu Pro Met
            100                 105                 110

Leu Met Glu Tyr Pro Glu Ala Ile Thr Arg Leu Val Thr Gly Ala Gln
            115                 120                 125

Arg Pro Pro Asp Pro Ala Pro Ala Pro Leu Gly Ala Pro Gly Leu Pro
        130                 135                 140

Asn Gly Leu Leu Ser Gly Asp Glu Asp Phe Ser Ser Ile Ala Asp Met
145                 150                 155                 160

Asp Phe Ser Ala Leu Leu Ser Gln Ile Ser Ser Gly Ser Gly Ser Gly
                165                 170                 175

Ser Arg Asp Ser Arg Glu Gly Met Phe Leu Pro Lys Pro Glu Ala Gly
            180                 185                 190

Ser Ala Ile Ser Asp Val Phe Glu Gly Arg Glu Val Cys Gln Pro Lys
            195                 200                 205

Arg Ile Arg Pro Phe His Pro Pro Gly Ser Pro Trp Ala Asn Arg Pro
        210                 215                 220

Leu Pro Ala Ser Leu Ala Pro Thr Pro Thr Gly Pro Val His Glu Pro
225                 230                 235                 240
```

```
Val Gly Ser Leu Thr Pro Ala Pro Val Pro Gln Pro Leu Asp Pro Ala
                245                 250                 255

Pro Ala Val Thr Pro Glu Ala Ser His Leu Leu Glu Asp Pro Asp Glu
            260                 265                 270

Glu Thr Ser Gln Ala Val Lys Ala Leu Arg Glu Met Ala Asp Thr Val
            275                 280                 285

Ile Pro Gln Lys Glu Ala Ala Ile Cys Gly Gln Met Asp Leu Ser
290                 295                 300

His Pro Pro Arg Gly His Leu Asp Glu Leu Thr Thr Thr Leu Glu
305                 310                 315                 320

Ser Met Thr Glu Asp Leu Asn Leu Asp Ser Pro Leu Thr Pro Glu Leu
                325                 330                 335

Asn Glu Ile Leu Asp Thr Phe Leu Asn Asp Glu Cys Leu Leu His Ala
                340                 345                 350

Met His Ile Ser Thr Gly Leu Ser Ile Phe Asp Thr Ser Leu Phe Thr
            355                 360                 365

Ser Gly Gly Gly Ser Lys Arg Pro Ala Ala Thr Lys Lys Ala Gly Gln
370                 375                 380

Ala Lys Lys Lys Lys Ser Arg
385                 390

<210> SEQ ID NO 25
<211> LENGTH: 382
<212> TYPE: PRT
<213> ORGANISM: Artificial Sequence
<220> FEATURE:
<223> OTHER INFORMATION: Synthetic construct created by rational design

<400> SEQUENCE: 25

Gly Ser Gly Arg Ala Asp Ala Leu Asp Asp Phe Asp Leu Asp Met Leu
1               5                   10                  15

Gly Ser Asp Ala Leu Asp Asp Phe Asp Leu Asp Met Leu Gly Ser Asp
                20                  25                  30

Ala Leu Asp Asp Phe Asp Leu Asp Met Leu Gly Ser Asp Ala Leu Asp
            35                  40                  45

Asp Phe Asp Leu Asp Met Leu Ile Asn Ser Arg Leu Val Thr Gly Ala
        50                  55                  60

Gln Arg Pro Pro Asp Pro Ala Pro Ala Pro Leu Gly Ala Pro Gly Leu
65                  70                  75                  80

Pro Asn Gly Leu Leu Ser Gly Asp Glu Asp Phe Ser Ser Ile Ala Asp
                85                  90                  95

Met Asp Phe Ser Ala Leu Leu Ser Gln Ile Ser Ser Gly Gly Gly Ser
                100                 105                 110

Arg Leu Val Thr Gly Ala Gln Arg Pro Pro Asp Pro Ala Pro Ala Pro
            115                 120                 125

Leu Gly Ala Pro Gly Leu Pro Asn Gly Leu Leu Ser Gly Asp Glu Asp
            130                 135                 140

Phe Ser Ser Ile Ala Asp Met Asp Phe Ser Ala Leu Leu Ser Gln Ile
145                 150                 155                 160

Ser Ser Gly Ser Gly Ser Gly Ser Arg Asp Ser Arg Glu Gly Met Phe
                165                 170                 175

Leu Pro Lys Pro Glu Ala Gly Ser Ala Ile Ser Asp Val Phe Glu Gly
            180                 185                 190

Arg Glu Val Cys Gln Pro Lys Arg Ile Arg Pro Phe His Pro Pro Gly
            195                 200                 205
```

```
Ser Pro Trp Ala Asn Arg Pro Leu Pro Ala Ser Leu Ala Pro Thr Pro
    210                 215                 220

Thr Gly Pro Val His Glu Pro Val Gly Ser Leu Thr Pro Ala Pro Val
225                 230                 235                 240

Pro Gln Pro Leu Asp Pro Ala Pro Ala Val Thr Pro Glu Ala Ser His
                245                 250                 255

Leu Leu Glu Asp Pro Asp Glu Glu Thr Ser Gln Ala Val Lys Ala Leu
            260                 265                 270

Arg Glu Met Ala Asp Thr Val Ile Pro Gln Lys Glu Glu Ala Ala Ile
        275                 280                 285

Cys Gly Gln Met Asp Leu Ser His Pro Pro Arg Gly His Leu Asp
    290                 295                 300

Glu Leu Thr Thr Thr Leu Glu Ser Met Thr Glu Asp Leu Asn Leu Asp
305                 310                 315                 320

Ser Pro Leu Thr Pro Glu Leu Asn Glu Ile Leu Asp Thr Phe Leu Asn
                325                 330                 335

Asp Glu Cys Leu Leu His Ala Met His Ile Ser Thr Gly Leu Ser Ile
            340                 345                 350

Phe Asp Thr Ser Leu Phe Thr Ser Gly Gly Ser Lys Arg Pro Ala
        355                 360                 365

Ala Thr Lys Lys Ala Gly Gln Ala Lys Lys Lys Ser Arg
    370                 375                 380

<210> SEQ ID NO 26
<211> LENGTH: 663
<212> TYPE: PRT
<213> ORGANISM: Artificial Sequence
<220> FEATURE:
<223> OTHER INFORMATION: Synthetic construct created by rational design

<400> SEQUENCE: 26

Met Pro Lys Lys Arg Lys Val Gly Gly Ser Pro Gly Gly Ala
1               5                   10                  15

Met Val Asp Thr Leu Ser Gly Leu Ser Ser Glu Gln Gly Gln Ser Gly
                20                  25                  30

Asp Met Thr Ile Glu Glu Asp Ser Ala Thr His Ile Lys Phe Ser Lys
            35                  40                  45

Arg Asp Glu Asp Gly Lys Glu Leu Ala Gly Ala Thr Met Glu Leu Arg
        50                  55                  60

Asp Ser Ser Gly Lys Thr Ile Ser Thr Trp Ile Ser Asp Gly Gln Val
65                  70                  75                  80

Lys Asp Phe Tyr Leu Tyr Pro Gly Lys Tyr Thr Phe Val Glu Thr Ala
                85                  90                  95

Ala Pro Asp Gly Tyr Glu Val Ala Thr Ala Ile Thr Phe Thr Val Asn
            100                 105                 110

Glu Gln Gly Gln Val Thr Val Asn Gly Lys Ala Thr Lys Gly Asp Ala
        115                 120                 125

His Ile Thr Gly Thr Ser Arg Ala Asp Pro Lys Lys Arg Lys Val
    130                 135                 140

Glu Ala Ser Gly Ser Gly Arg Ala Asp Ala Leu Asp Asp Phe Asp Leu
145                 150                 155                 160

Asp Met Leu Gly Ser Asp Ala Leu Asp Asp Phe Asp Leu Asp Met Leu
                165                 170                 175

Gly Ser Asp Ala Leu Asp Asp Phe Asp Leu Asp Met Leu Gly Ser Asp
            180                 185                 190
```

```
Ala Leu Asp Asp Phe Asp Leu Asp Met Leu Ile Asn Ser Arg Ser Gln
            195                 200                 205

Tyr Leu Pro Asp Thr Asp Asp Arg His Arg Ile Glu Glu Lys Arg Lys
        210                 215                 220

Arg Thr Tyr Glu Thr Phe Lys Ser Ile Met Lys Lys Ser Pro Phe Ser
225                 230                 235                 240

Gly Pro Thr Asp Pro Arg Pro Pro Arg Arg Ile Ala Val Pro Ser
                245                 250                 255

Arg Ser Ser Ala Ser Val Pro Lys Pro Ala Pro Gln Pro Tyr Pro Phe
                260                 265                 270

Thr Ser Ser Leu Ser Thr Ile Asn Tyr Asp Glu Phe Pro Thr Met Val
                275                 280                 285

Phe Pro Ser Gly Gln Ile Ser Gln Ala Ser Ala Leu Ala Pro Ala Pro
        290                 295                 300

Pro Gln Val Leu Pro Gln Ala Pro Ala Pro Ala Pro Ala Pro Ala Met
305                 310                 315                 320

Val Ser Ala Leu Ala Gln Ala Pro Ala Pro Val Pro Val Leu Ala Pro
                325                 330                 335

Gly Pro Pro Gln Ala Val Ala Pro Ala Pro Lys Pro Thr Gln Ala
                340                 345                 350

Gly Glu Gly Thr Leu Ser Glu Ala Leu Leu Gln Leu Gln Phe Asp Asp
        355                 360                 365

Glu Asp Leu Gly Ala Leu Leu Gly Asn Ser Thr Asp Pro Ala Val Phe
        370                 375                 380

Thr Asp Leu Ala Ser Val Asp Asn Ser Glu Phe Gln Gln Leu Leu Asn
385                 390                 395                 400

Gln Gly Ile Pro Val Ala Pro His Thr Thr Glu Pro Met Leu Met Glu
                405                 410                 415

Tyr Pro Glu Ala Ile Thr Arg Leu Val Thr Gly Ala Gln Arg Pro Pro
                420                 425                 430

Asp Pro Ala Pro Ala Pro Leu Gly Ala Pro Gly Leu Pro Asn Gly Leu
            435                 440                 445

Leu Ser Gly Asp Glu Asp Phe Ser Ser Ile Ala Asp Met Asp Phe Ser
        450                 455                 460

Ala Leu Leu Gly Ser Gly Ser Gly Ser Arg Asp Ser Arg Glu Gly Met
465                 470                 475                 480

Phe Leu Pro Lys Pro Glu Ala Gly Ser Ala Ile Ser Asp Val Phe Glu
                485                 490                 495

Gly Arg Glu Val Cys Gln Pro Lys Arg Ile Arg Pro Phe His Pro Pro
                500                 505                 510

Gly Ser Pro Trp Ala Asn Arg Pro Leu Pro Ala Ser Leu Ala Pro Thr
            515                 520                 525

Pro Thr Gly Pro Val His Glu Pro Val Gly Ser Leu Thr Pro Ala Pro
        530                 535                 540

Val Pro Gln Pro Leu Asp Pro Ala Pro Ala Val Thr Pro Glu Ala Ser
545                 550                 555                 560

His Leu Leu Glu Asp Pro Asp Glu Glu Thr Ser Gln Ala Val Lys Ala
                565                 570                 575

Leu Arg Glu Met Ala Asp Thr Val Ile Pro Gln Lys Glu Glu Ala Ala
            580                 585                 590

Ile Cys Gly Gln Met Asp Leu Ser His Pro Pro Pro Arg Gly His Leu
        595                 600                 605
```

```
Asp Glu Leu Thr Thr Thr Leu Glu Ser Met Thr Glu Asp Leu Asn Leu
        610                 615                 620

Asp Ser Pro Leu Thr Pro Glu Leu Asn Glu Ile Leu Asp Thr Phe Leu
625                 630                 635                 640

Asn Asp Glu Cys Leu Leu His Ala Met His Ile Ser Thr Gly Leu Ser
                645                 650                 655

Ile Phe Asp Thr Ser Leu Phe
                660

<210> SEQ ID NO 27
<211> LENGTH: 88
<212> TYPE: PRT
<213> ORGANISM: Artificial Sequence
<220> FEATURE:
<223> OTHER INFORMATION: Synthetic construct created by rational design

<400> SEQUENCE: 27

Gly Gly Gly Ser Gly Gly Ala His Ile Val Met Val Asp Ala Tyr Lys
1               5                   10                  15

Pro Thr Lys Gly Gly Ser Gly Gly Gly Ser Gly Gly Ala His Ile
                20                  25                  30

Val Met Val Asp Ala Tyr Lys Pro Thr Lys Gly Gly Ser Gly Gly Gly
            35                  40                  45

Gly Ser Gly Gly Ala His Ile Val Met Val Asp Ala Tyr Lys Pro Thr
        50                  55                  60

Lys Gly Gly Ser Gly Gly Gly Gly Ser Gly Gly Ala His Ile Val Met
65                  70                  75                  80

Val Asp Ala Tyr Lys Pro Thr Lys
                85

<210> SEQ ID NO 28
<211> LENGTH: 643
<212> TYPE: PRT
<213> ORGANISM: Artificial Sequence
<220> FEATURE:
<223> OTHER INFORMATION: Synthetic construct created by rational design

<400> SEQUENCE: 28

Met Pro Lys Lys Lys Arg Lys Val Gly Gly Gly Ser Pro Gly Asn His
1               5                   10                  15

Val Ile Glu Thr Glu Gln Asn Leu Pro Asn Glu Asp Gly Gln Ser Gly
            20                  25                  30

Asn Ile Ile Glu Gln Glu Asp Ser Lys Thr Leu Val Lys Phe Ser Lys
        35                  40                  45

Arg Asp Ile Lys Gly Asn Glu Leu Ala Gly Ala Thr Ile Glu Leu Arg
    50                  55                  60

Asp Leu Ser Gly Lys Ser Ile Gln Ser Trp Val Ser Asp Gly Lys Ala
65                  70                  75                  80

Lys Asp Phe Tyr Leu Leu Pro Gly Ser Tyr Glu Phe Val Glu Thr Ala
                85                  90                  95

Ala Pro Glu Gly Tyr Gln Ile Ala Thr Lys Ile Met Phe Thr Ile Ser
                100                 105                 110

Thr Asp Gly Arg Ile Thr Val Asp Gly Gln Leu Val Thr Gly Thr Gly
            115                 120                 125

Ser Gly Arg Ala Asp Ala Leu Asp Asp Phe Asp Leu Asp Met Leu Gly
        130                 135                 140

Ser Asp Ala Leu Asp Asp Phe Asp Leu Asp Met Leu Gly Ser Asp Ala
145                 150                 155                 160
```

```
Leu Asp Asp Phe Asp Leu Asp Met Leu Gly Ser Asp Ala Leu Asp Asp
                165                 170                 175

Phe Asp Leu Asp Met Leu Ile Asn Ser Arg Ser Gln Tyr Leu Pro Asp
            180                 185                 190

Thr Asp Asp Arg His Arg Ile Glu Glu Lys Arg Lys Arg Thr Tyr Glu
        195                 200                 205

Thr Phe Lys Ser Ile Met Lys Lys Ser Pro Phe Ser Gly Pro Thr Asp
    210                 215                 220

Pro Arg Pro Pro Arg Arg Ile Ala Val Pro Ser Arg Ser Ser Ala
225                 230                 235                 240

Ser Val Pro Lys Pro Ala Pro Gln Pro Tyr Pro Phe Thr Ser Ser Leu
                245                 250                 255

Ser Thr Ile Asn Tyr Asp Glu Phe Pro Thr Met Val Phe Pro Ser Gly
            260                 265                 270

Gln Ile Ser Gln Ala Ser Ala Leu Ala Pro Ala Pro Pro Gln Val Leu
        275                 280                 285

Pro Gln Ala Pro Ala Pro Ala Pro Ala Pro Ala Met Val Ser Ala Leu
    290                 295                 300

Ala Gln Ala Pro Ala Pro Val Pro Val Leu Ala Pro Gly Pro Pro Gln
305                 310                 315                 320

Ala Val Ala Pro Pro Ala Pro Lys Pro Thr Gln Ala Gly Glu Gly Thr
                325                 330                 335

Leu Ser Glu Ala Leu Leu Gln Leu Gln Phe Asp Asp Glu Asp Leu Gly
            340                 345                 350

Ala Leu Leu Gly Asn Ser Thr Asp Pro Ala Val Phe Thr Asp Leu Ala
        355                 360                 365

Ser Val Asp Asn Ser Glu Phe Gln Gln Leu Leu Asn Gln Gly Ile Pro
    370                 375                 380

Val Ala Pro His Thr Thr Glu Pro Met Leu Met Glu Tyr Pro Glu Ala
385                 390                 395                 400

Ile Thr Arg Leu Val Thr Gly Ala Gln Arg Pro Pro Asp Pro Ala Pro
                405                 410                 415

Ala Pro Leu Gly Ala Pro Gly Leu Pro Asn Gly Leu Leu Ser Gly Asp
            420                 425                 430

Glu Asp Phe Ser Ser Ile Ala Asp Met Asp Phe Ser Ala Leu Leu Gly
        435                 440                 445

Ser Gly Ser Gly Ser Arg Asp Ser Arg Glu Gly Met Phe Leu Pro Lys
    450                 455                 460

Pro Glu Ala Gly Ser Ala Ile Ser Asp Val Phe Glu Gly Arg Glu Val
465                 470                 475                 480

Cys Gln Pro Lys Arg Ile Arg Pro Phe His Pro Pro Gly Ser Pro Trp
                485                 490                 495

Ala Asn Arg Pro Leu Pro Ala Ser Leu Ala Pro Thr Pro Thr Gly Pro
            500                 505                 510

Val His Glu Pro Val Gly Ser Leu Thr Pro Ala Pro Val Pro Gln Pro
        515                 520                 525

Leu Asp Pro Ala Pro Ala Val Thr Pro Glu Ala Ser His Leu Leu Glu
    530                 535                 540

Asp Pro Asp Glu Glu Thr Ser Gln Ala Val Lys Ala Leu Arg Glu Met
545                 550                 555                 560

Ala Asp Thr Val Ile Pro Gln Lys Glu Glu Ala Ala Ile Cys Gly Gln
                565                 570                 575
```

```
Met Asp Leu Ser His Pro Pro Arg Gly His Leu Asp Glu Leu Thr
            580                 585                 590

Thr Thr Leu Glu Ser Met Thr Glu Asp Leu Asn Leu Asp Ser Pro Leu
        595                 600                 605

Thr Pro Glu Leu Asn Glu Ile Leu Asp Thr Phe Leu Asn Asp Glu Cys
    610                 615                 620

Leu Leu His Ala Met His Ile Ser Thr Gly Leu Ser Ile Phe Asp Thr
625                 630                 635                 640

Ser Leu Phe

<210> SEQ ID NO 29
<211> LENGTH: 78
<212> TYPE: PRT
<213> ORGANISM: Artificial Sequence
<220> FEATURE:
<223> OTHER INFORMATION: Synthetic construct created by rational design

<400> SEQUENCE: 29

Gly Gly Gly Ser Gly Gly Ala His Ile Val Met Val Asp Asn Tyr Lys
1               5                   10                  15

Pro Ile Val Gly Gly Ser Gly Gly Ala His Ile Val Met Val Asp Asn
            20                  25                  30

Tyr Lys Pro Ile Val Gly Gly Ser Gly Gly Ala His Ile Val Met Val
        35                  40                  45

Asp Asn Tyr Lys Pro Ile Val Gly Gly Ser Gly Gly Gly Gly Ser Gly
    50                  55                  60

Gly Ala His Ile Val Met Val Asp Asn Tyr Lys Pro Ile Val
65                  70                  75

<210> SEQ ID NO 30
<211> LENGTH: 285
<212> TYPE: PRT
<213> ORGANISM: Artificial Sequence
<220> FEATURE:
<223> OTHER INFORMATION: Synthetic construct created by rational design

<400> SEQUENCE: 30

Gly Ser Gly Arg Ala Asp Ala Leu Asp Asp Phe Asp Leu Asp Met Leu
1               5                   10                  15

Gly Ser Asp Ala Leu Asp Asp Phe Asp Leu Asp Met Leu Gly Ser Asp
            20                  25                  30

Ala Leu Asp Asp Phe Asp Leu Asp Met Leu Gly Ser Asp Ala Leu Asp
        35                  40                  45

Asp Phe Asp Leu Asp Met Leu Ile Asn Ser Arg Leu Val Thr Gly Ala
    50                  55                  60

Gln Arg Pro Pro Asp Pro Ala Pro Ala Pro Leu Gly Ala Pro Gly Leu
65                  70                  75                  80

Pro Asn Gly Leu Leu Ser Gly Asp Glu Asp Phe Ser Ser Ile Ala Asp
            85                  90                  95

Met Asp Phe Ser Ala Leu Leu Ser Gln Ile Ser Ser Gly Gly Gly Ser
            100                 105                 110

Arg Leu Val Thr Gly Ala Gln Arg Pro Pro Asp Pro Ala Pro Ala Pro
        115                 120                 125

Leu Gly Ala Pro Gly Leu Pro Asn Gly Leu Leu Ser Gly Asp Glu Asp
    130                 135                 140

Phe Ser Ser Ile Ala Asp Met Asp Phe Ser Ala Leu Leu Ser Gln Ile
145                 150                 155                 160
```

Ser Ser Gly Ser Gly Ser Gln Pro Leu Asp Pro Ala Pro Ala Val Thr
            165                 170                 175

Pro Glu Ala Ser His Leu Leu Glu Asp Pro Asp Glu Glu Thr Ser Gln
        180                 185                 190

Ala Val Lys Ala Leu Arg Glu Met Ala Asp Thr Val Ile Pro Gln Lys
    195                 200                 205

Glu Glu Ala Ala Ile Cys Gly Gln Met Asp Leu Ser His Pro Pro
    210                 215                 220

Arg Gly His Leu Asp Glu Leu Thr Thr Thr Leu Glu Ser Met Thr Glu
225                 230                 235                 240

Asp Leu Asn Leu Asp Ser Pro Leu Thr Pro Glu Leu Asn Glu Ile Leu
            245                 250                 255

Asp Thr Phe Leu Asn Asp Glu Cys Leu Leu His Ala Met His Ile Ser
        260                 265                 270

Thr Gly Leu Ser Ile Phe Asp Thr Ser Leu Phe Thr Ser
    275                 280                 285

<210> SEQ ID NO 31
<211> LENGTH: 20
<212> TYPE: DNA
<213> ORGANISM: Artificial Sequence
<220> FEATURE:
<223> OTHER INFORMATION: Synthetic construct created by rational design

<400> SEQUENCE: 31
gctgtgtttg cgtctctccc                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic construct created by rational design

<400> SEQUENCE: 32
ggggtggtga caagtgtgat                                              20

<210> SEQ ID NO 33
<211> LENGTH: 1433
<212> TYPE: PRT
<213> ORGANISM: Artificial Sequence
<220> FEATURE:
<223> OTHER INFORMATION: Synthetic construct created by rational design

<400> SEQUENCE: 33

Met Pro Lys Lys Lys Arg Lys Val Gly Gly Ser Pro Gly Gly Gly
1               5                   10                  15

Gly Ser Leu Arg Asn Tyr Ile Leu Gly Leu Asp Ile Gly Ile Thr Ser
            20                  25                  30

Val Gly Tyr Gly Ile Ile Asp Tyr Glu Thr Arg Asp Val Ile Asp Ala
        35                  40                  45

Gly Val Arg Leu Phe Lys Glu Ala Asn Val Glu Asn Asn Glu Gly Arg
    50                  55                  60

Arg Ser Lys Arg Gly Ala Arg Arg Leu Lys Arg Arg Arg Arg His Arg
65                  70                  75                  80

Ile Gln Arg Val Lys Lys Leu Leu Phe Asp Tyr Asn Leu Leu Thr Asp
                85                  90                  95

His Ser Glu Leu Ser Gly Ile Asn Pro Tyr Glu Ala Arg Val Lys Gly
            100                 105                 110

-continued

```
Leu Ser Gln Lys Leu Ser Glu Glu Phe Ser Ala Leu Leu His
        115                 120                 125
Leu Ala Lys Arg Arg Gly Val His Asn Val Asn Glu Val Glu Asp
130                 135                 140
Thr Gly Asn Glu Leu Ser Thr Lys Glu Gln Ile Ser Arg Asn Ser Lys
145                 150                 155                 160
Ala Leu Glu Glu Lys Tyr Val Ala Glu Leu Gln Leu Glu Arg Leu Lys
                165                 170                 175
Lys Asp Gly Glu Val Arg Gly Ser Ile Asn Arg Phe Lys Thr Ser Asp
            180                 185                 190
Tyr Val Lys Glu Ala Lys Gln Leu Leu Lys Val Gln Lys Ala Tyr His
        195                 200                 205
Gln Leu Asp Gln Ser Phe Ile Asp Thr Tyr Ile Asp Leu Leu Glu Thr
    210                 215                 220
Arg Arg Thr Tyr Tyr Glu Gly Pro Gly Glu Gly Ser Pro Phe Gly Trp
225                 230                 235                 240
Lys Asp Ile Lys Glu Trp Tyr Glu Met Leu Met Gly His Cys Thr Tyr
                245                 250                 255
Phe Pro Glu Glu Leu Arg Ser Val Lys Tyr Ala Tyr Asn Ala Asp Leu
            260                 265                 270
Tyr Asn Ala Leu Asn Asp Leu Asn Asn Leu Val Ile Thr Arg Asp Glu
        275                 280                 285
Asn Glu Lys Leu Glu Tyr Tyr Glu Lys Phe Gln Ile Ile Glu Asn Val
    290                 295                 300
Phe Lys Gln Lys Lys Lys Pro Thr Leu Lys Gln Ile Ala Lys Glu Ile
305                 310                 315                 320
Leu Val Asn Glu Glu Asp Ile Lys Gly Tyr Arg Val Thr Ser Thr Gly
                325                 330                 335
Lys Pro Glu Phe Thr Asn Leu Lys Val Tyr His Asp Ile Lys Asp Ile
            340                 345                 350
Thr Ala Arg Lys Glu Ile Ile Glu Asn Ala Glu Leu Leu Asp Gln Ile
        355                 360                 365
Ala Lys Ile Leu Thr Ile Tyr Gln Ser Ser Glu Asp Ile Gln Glu Glu
    370                 375                 380
Leu Thr Asn Leu Asn Ser Glu Leu Thr Gln Glu Glu Ile Glu Gln Ile
385                 390                 395                 400
Ser Asn Leu Lys Gly Tyr Thr Gly Thr His Asn Leu Ser Leu Lys Ala
                405                 410                 415
Ile Asn Leu Ile Leu Asp Glu Leu Trp His Thr Asn Asp Asn Gln Ile
            420                 425                 430
Ala Ile Phe Asn Arg Leu Lys Leu Val Pro Lys Lys Val Asp Leu Ser
        435                 440                 445
Gln Gln Lys Glu Ile Pro Thr Thr Leu Val Asp Asp Phe Ile Leu Ser
    450                 455                 460
Pro Val Val Lys Arg Ser Phe Ile Gln Ser Ile Lys Val Ile Asn Ala
465                 470                 475                 480
Ile Ile Lys Lys Tyr Gly Leu Pro Asn Asp Ile Ile Ile Glu Leu Gly
                485                 490                 495
Ser Lys Arg Tyr Ala Thr Arg Gly Leu Met Asn Leu Leu Arg Ser Tyr
            500                 505                 510
Phe Arg Val Asn Asn Leu Asp Val Lys Val Lys Ser Ile Asn Gly Gly
        515                 520                 525
Phe Thr Ser Phe Leu Arg Arg Lys Trp Lys Phe Lys Lys Glu Arg Asn
```

```
            530                 535                 540
Lys Gly Tyr Lys His His Ala Glu Asp Ala Leu Ile Ile Ala Asn Ala
545                 550                 555                 560

Asp Phe Ile Phe Lys Glu Trp Lys Lys Leu Asp Lys Ala Lys Lys Val
                565                 570                 575

Met Glu Asn Gln Met Phe Glu Lys Gln Ala Glu Ser Met Pro Glu
            580                 585                 590

Ile Glu Thr Glu Gln Glu Tyr Lys Glu Ile Phe Ile Thr Pro His Gln
            595                 600                 605

Ile Lys His Ile Lys Asp Phe Lys Asp Tyr Lys Tyr Ser His Arg Val
610                 615                 620

Asp Lys Lys Pro Asn Arg Lys Leu Ile Asn Asp Thr Leu Tyr Ser Thr
625                 630                 635                 640

Arg Lys Asp Asp Lys Gly Asn Thr Leu Ile Val Asn Asn Leu Asn Gly
                645                 650                 655

Leu Tyr Asp Lys Asp Asn Asp Lys Leu Lys Lys Leu Ile Asn Lys Ser
                660                 665                 670

Pro Glu Lys Leu Leu Met Tyr His His Asp Pro Gln Thr Tyr Gln Lys
                675                 680                 685

Leu Lys Leu Ile Met Glu Gln Tyr Gly Asp Glu Lys Asn Pro Leu Tyr
            690                 695                 700

Lys Tyr Tyr Glu Glu Thr Gly Asn Tyr Leu Thr Lys Tyr Ser Lys Lys
705                 710                 715                 720

Asp Asn Gly Pro Val Ile Lys Lys Ile Lys Tyr Tyr Gly Asn Lys Leu
                725                 730                 735

Asn Ala His Leu Asp Ile Thr Asp Asp Tyr Pro Asn Ser Arg Asn Lys
            740                 745                 750

Val Val Lys Leu Ser Leu Lys Pro Tyr Arg Phe Asp Val Tyr Leu Asp
            755                 760                 765

Asn Gly Val Tyr Lys Phe Val Thr Val Lys Asn Leu Asp Val Ile Lys
            770                 775                 780

Lys Glu Asn Tyr Tyr Glu Val Asn Ser Lys Cys Tyr Glu Glu Ala Lys
785                 790                 795                 800

Lys Leu Lys Lys Ile Ser Asn Gln Ala Glu Phe Ile Ala Ser Phe Tyr
                805                 810                 815

Lys Asn Asp Leu Ile Lys Ile Asn Gly Glu Leu Tyr Arg Val Ile Gly
                820                 825                 830

Val Asn Asn Asp Leu Leu Asn Arg Ile Glu Val Asn Met Ile Asp Ile
            835                 840                 845

Thr Tyr Arg Glu Tyr Leu Glu Asn Met Asn Asp Lys Arg Pro Pro His
850                 855                 860

Ile Ile Lys Thr Ile Ala Ser Lys Thr Gln Ser Ile Lys Lys Tyr Ser
865                 870                 875                 880

Thr Asp Ile Leu Gly Asn Leu Tyr Glu Val Lys Ser Lys Lys His Pro
                885                 890                 895

Gln Ile Ile Lys Lys Gly Thr Ser Arg Ala Asp Pro Lys Lys Lys Arg
                900                 905                 910

Lys Val Glu Ala Ser Gly Ser Gly Arg Ala Asp Ala Leu Asp Asp Phe
            915                 920                 925

Asp Leu Asp Met Leu Gly Ser Asp Ala Leu Asp Asp Phe Asp Leu Asp
            930                 935                 940

Met Leu Gly Ser Asp Ala Leu Asp Asp Phe Asp Leu Asp Met Leu Gly
945                 950                 955                 960
```

-continued

```
Ser Asp Ala Leu Asp Asp Phe Asp Leu Asp Met Leu Ile Asn Ser Arg
            965                 970                 975

Ser Gln Tyr Leu Pro Asp Thr Asp Asp Arg His Arg Ile Glu Glu Lys
            980                 985                 990

Arg Lys Arg Thr Tyr Glu Thr Phe Lys Ser Ile Met Lys Lys Ser Pro
            995                 1000                1005

Phe Ser Gly Pro Thr Asp Pro Arg Pro Pro Arg Arg Ile Ala
    1010            1015            1020

Val Pro Ser Arg Ser Ser Ala Ser Val Pro Lys Pro Ala Pro Gln
    1025            1030            1035

Pro Tyr Pro Phe Thr Ser Ser Leu Ser Thr Ile Asn Tyr Asp Glu
    1040            1045            1050

Phe Pro Thr Met Val Phe Pro Ser Gly Gln Ile Ser Gln Ala Ser
    1055            1060            1065

Ala Leu Ala Pro Ala Pro Pro Gln Val Leu Pro Gln Ala Pro Ala
    1070            1075            1080

Pro Ala Pro Ala Pro Ala Met Val Ser Ala Leu Ala Gln Ala Pro
    1085            1090            1095

Ala Pro Val Pro Val Leu Ala Pro Gly Pro Pro Gln Ala Val Ala
    1100            1105            1110

Pro Pro Ala Pro Lys Pro Thr Gln Ala Gly Glu Gly Thr Leu Ser
    1115            1120            1125

Glu Ala Leu Leu Gln Leu Gln Phe Asp Asp Glu Asp Leu Gly Ala
    1130            1135            1140

Leu Leu Gly Asn Ser Thr Asp Pro Ala Val Phe Thr Asp Leu Ala
    1145            1150            1155

Ser Val Asp Asn Ser Glu Phe Gln Gln Leu Leu Asn Gln Gly Ile
    1160            1165            1170

Pro Val Ala Pro His Thr Thr Glu Pro Met Leu Met Glu Tyr Pro
    1175            1180            1185

Glu Ala Ile Thr Arg Leu Val Thr Gly Ala Gln Arg Pro Pro Asp
    1190            1195            1200

Pro Ala Pro Ala Pro Leu Gly Ala Pro Gly Leu Pro Asn Gly Leu
    1205            1210            1215

Leu Ser Gly Asp Glu Asp Phe Ser Ser Ile Ala Asp Met Asp Phe
    1220            1225            1230

Ser Ala Leu Leu Gly Ser Gly Ser Gly Ser Arg Asp Ser Arg Glu
    1235            1240            1245

Gly Met Phe Leu Pro Lys Pro Glu Ala Gly Ser Ala Ile Ser Asp
    1250            1255            1260

Val Phe Glu Gly Arg Glu Val Cys Gln Pro Lys Arg Ile Arg Pro
    1265            1270            1275

Phe His Pro Pro Gly Ser Pro Trp Ala Asn Arg Pro Leu Pro Ala
    1280            1285            1290

Ser Leu Ala Pro Thr Pro Thr Gly Pro Val His Glu Pro Val Gly
    1295            1300            1305

Ser Leu Thr Pro Ala Pro Val Pro Gln Pro Leu Asp Pro Ala Pro
    1310            1315            1320

Ala Val Thr Pro Glu Ala Ser His Leu Leu Glu Asp Pro Asp Glu
    1325            1330            1335

Glu Thr Ser Gln Ala Val Lys Ala Leu Arg Glu Met Ala Asp Thr
    1340            1345            1350
```

-continued

```
Val Ile Pro Gln Lys Glu Ala Ala Ile Cys Gly Gln Met Asp
    1355                1360                1365

Leu Ser His Pro Pro Arg Gly His Leu Asp Glu Leu Thr Thr
    1370                1375                1380

Thr Leu Glu Ser Met Thr Glu Asp Leu Asn Leu Asp Ser Pro Leu
    1385                1390                1395

Thr Pro Glu Leu Asn Glu Ile Leu Asp Thr Phe Leu Asn Asp Glu
    1400                1405                1410

Cys Leu Leu His Ala Met His Ile Ser Thr Gly Leu Ser Ile Phe
    1415                1420                1425

Asp Thr Ser Leu Phe
    1430

<210> SEQ ID NO 34
<211> LENGTH: 1414
<212> TYPE: PRT
<213> ORGANISM: Artificial Sequence
<220> FEATURE:
<223> OTHER INFORMATION: Synthetic construct created by rational design

<400> SEQUENCE: 34

Met Pro Lys Lys Lys Arg Lys Val Gly Gly Gly Ser Pro Gly Gly Gly
1               5                   10                  15

Gly Ser Lys Arg Asn Tyr Ile Leu Gly Leu Asp Ile Gly Ile Thr Ser
                20                  25                  30

Val Gly Tyr Gly Ile Ile Asp Tyr Glu Thr Arg Asp Val Ile Asp Ala
            35                  40                  45

Gly Val Arg Leu Phe Lys Glu Ala Asn Val Glu Asn Asn Glu Gly Arg
        50                  55                  60

Arg Ser Lys Arg Gly Ala Arg Arg Leu Lys Arg Arg Arg His Arg
65                  70                  75                  80

Ile Gln Arg Val Lys Lys Leu Leu Phe Asp Tyr Asn Leu Leu Thr Asp
                85                  90                  95

His Ser Glu Leu Ser Gly Ile Asn Pro Tyr Glu Ala Arg Val Lys Gly
            100                 105                 110

Leu Ser Gln Lys Leu Ser Glu Glu Phe Ser Ala Ala Leu Leu His
        115                 120                 125

Leu Ala Lys Arg Arg Gly Val His Asn Val Asn Glu Val Glu Glu Asp
130                 135                 140

Thr Gly Asn Glu Leu Ser Thr Lys Glu Gln Ile Ser Arg Asn Ser Lys
145                 150                 155                 160

Ala Leu Glu Glu Lys Tyr Val Ala Glu Leu Gln Leu Glu Arg Leu Lys
                165                 170                 175

Lys Asp Gly Glu Val Arg Gly Ser Ile Asn Arg Phe Lys Thr Ser Asp
            180                 185                 190

Tyr Val Lys Glu Ala Lys Gln Leu Leu Lys Val Gln Lys Ala Tyr His
        195                 200                 205

Gln Leu Asp Gln Ser Phe Ile Asp Thr Tyr Ile Asp Leu Leu Glu Thr
    210                 215                 220

Arg Arg Thr Tyr Tyr Glu Gly Pro Gly Glu Gly Ser Pro Phe Gly Trp
225                 230                 235                 240

Lys Asp Ile Lys Glu Trp Tyr Glu Met Leu Met Gly His Cys Thr Lys
                245                 250                 255

Lys Val Asp Leu Ser Gln Gln Lys Glu Ile Pro Thr Thr Leu Val Asp
            260                 265                 270
```

```
Asp Phe Ile Leu Ser Pro Val Val Lys Arg Ser Phe Ile Gln Ser Ile
            275                 280                 285

Lys Val Ile Asn Ala Ile Ile Lys Lys Tyr Gly Leu Pro Asn Asp Ile
        290                 295                 300

Ile Ile Glu Leu Ala Arg Glu Lys Asn Ser Lys Asp Ala Gln Lys Met
305                 310                 315                 320

Ile Asn Glu Met Gln Lys Arg Asn Arg Gln Thr Asn Glu Arg Ile Glu
                325                 330                 335

Glu Ile Ile Arg Thr Thr Gly Lys Glu Asn Ala Lys Tyr Leu Ile Glu
            340                 345                 350

Lys Ile Lys Leu His Asp Met Gln Glu Gly Lys Cys Leu Tyr Ser Leu
        355                 360                 365

Glu Ala Ile Pro Leu Glu Asp Leu Leu Asn Asn Pro Phe Asn Tyr Glu
370                 375                 380

Val Asp His Ile Ile Pro Arg Ser Val Ser Phe Asp Asn Ser Phe Asn
385                 390                 395                 400

Asn Lys Val Leu Val Lys Gln Glu Glu Asn Ser Lys Lys Gly Asn Arg
                405                 410                 415

Thr Pro Phe Gln Tyr Leu Ser Ser Ser Asp Ser Lys Ile Ser Tyr Glu
            420                 425                 430

Thr Phe Lys Lys His Ile Leu Asn Leu Ala Lys Gly Lys Gly Arg Ile
        435                 440                 445

Ser Lys Thr Lys Lys Glu Tyr Leu Leu Glu Glu Arg Asp Ile Asn Arg
        450                 455                 460

Phe Ser Val Gln Lys Asp Phe Ile Asn Arg Asn Leu Val Asp Thr Arg
465                 470                 475                 480

Tyr Ala Thr Arg Gly Leu Met Asn Leu Leu Arg Ser Tyr Phe Arg Val
                485                 490                 495

Asn Asn Leu Asp Val Lys Val Lys Ser Ile Asn Gly Gly Phe Thr Ser
            500                 505                 510

Phe Leu Arg Arg Lys Trp Lys Phe Lys Lys Glu Arg Asn Lys Gly Tyr
        515                 520                 525

Lys His His Ala Glu Asp Ala Leu Ile Ile Ala Asn Ala Asp Phe Ile
        530                 535                 540

Phe Lys Glu Trp Lys Lys Leu Asp Lys Ala Lys Lys Val Met Glu Asn
545                 550                 555                 560

Gln Met Phe Glu Glu Lys Gln Ala Glu Ser Met Pro Glu Ile Glu Thr
                565                 570                 575

Glu Gln Glu Tyr Lys Glu Ile Phe Ile Thr Pro His Gln Ile Lys His
            580                 585                 590

Ile Lys Asp Phe Lys Asp Tyr Lys Tyr Ser His Arg Val Asp Lys Lys
        595                 600                 605

Pro Asn Arg Lys Leu Ile Asn Asp Thr Leu Tyr Ser Thr Arg Lys Asp
        610                 615                 620

Asp Lys Gly Asn Thr Leu Ile Val Asn Asn Leu Asn Gly Leu Tyr Asp
625                 630                 635                 640

Lys Asp Asn Asp Lys Leu Lys Lys Leu Ile Asn Lys Ser Pro Glu Lys
                645                 650                 655

Leu Leu Met Tyr His His Asp Pro Gln Thr Tyr Gln Lys Leu Lys Leu
            660                 665                 670

Ile Met Glu Gln Tyr Gly Asp Glu Lys Asn Pro Leu Tyr Lys Tyr Tyr
        675                 680                 685

Glu Glu Thr Gly Asn Tyr Leu Thr Lys Tyr Ser Lys Lys Asp Asn Gly
```

-continued

```
            690                 695                 700
Pro Val Ile Lys Lys Ile Lys Tyr Tyr Gly Asn Lys Leu Asn Ala His
705                     710                 715                 720

Leu Asp Ile Thr Asp Asp Tyr Pro Asn Ser Arg Asn Lys Val Val Lys
                725                 730                 735

Leu Ser Leu Lys Pro Tyr Arg Phe Asp Val Tyr Leu Asp Asn Gly Val
                740                 745                 750

Tyr Lys Phe Val Thr Val Lys Asn Leu Asp Val Ile Lys Lys Glu Asn
            755                 760                 765

Tyr Tyr Glu Val Asn Ser Lys Cys Tyr Glu Glu Ala Lys Lys Leu Lys
        770                 775                 780

Lys Ile Ser Asn Gln Ala Glu Phe Ile Ala Ser Phe Tyr Lys Asn Asp
785                 790                 795                 800

Leu Ile Lys Ile Asn Gly Glu Leu Tyr Arg Val Ile Gly Val Asn Asn
                805                 810                 815

Asp Leu Leu Asn Arg Ile Glu Val Asn Met Ile Asp Ile Thr Tyr Arg
                820                 825                 830

Glu Tyr Leu Glu Asn Met Asn Asp Lys Arg Pro Pro His Ile Ile Lys
            835                 840                 845

Thr Ile Ala Ser Lys Thr Gln Ser Ile Lys Lys Tyr Ser Thr Asp Ile
        850                 855                 860

Leu Gly Asn Leu Tyr Glu Val Lys Ser Lys His Pro Gln Ile Ile
865                 870                 875                 880

Lys Lys Gly Thr Ser Arg Ala Asp Pro Lys Lys Lys Arg Lys Val Glu
                885                 890                 895

Ala Ser Gly Ser Gly Arg Ala Asp Ala Leu Asp Asp Phe Asp Leu Asp
                900                 905                 910

Met Leu Gly Ser Asp Ala Leu Asp Asp Phe Asp Leu Asp Met Leu Gly
            915                 920                 925

Ser Asp Ala Leu Asp Asp Phe Asp Leu Asp Met Leu Gly Ser Asp Ala
        930                 935                 940

Leu Asp Asp Phe Asp Leu Asp Met Leu Ile Asn Ser Arg Ser Gln Tyr
945                 950                 955                 960

Leu Pro Asp Thr Asp Asp Arg His Arg Ile Glu Glu Lys Arg Lys Arg
                965                 970                 975

Thr Tyr Glu Thr Phe Lys Ser Ile Met Lys Lys Ser Pro Phe Ser Gly
            980                 985                 990

Pro Thr Asp Pro Arg Pro Pro Pro Arg Arg Ile Ala Val Pro Ser Arg
        995                 1000                1005

Ser Ser Ala Ser Val Pro Lys Pro Ala Pro Gln Pro Tyr Pro Phe
    1010                1015                1020

Thr Ser Ser Leu Ser Thr Ile Asn Tyr Asp Glu Phe Pro Thr Met
    1025                1030                1035

Val Phe Pro Ser Gly Gln Ile Ser Gln Ala Ser Ala Leu Ala Pro
    1040                1045                1050

Ala Pro Pro Gln Val Leu Pro Gln Ala Pro Ala Pro Ala Pro Ala
    1055                1060                1065

Pro Ala Met Val Ser Ala Leu Ala Gln Ala Pro Ala Pro Val Pro
    1070                1075                1080

Val Leu Ala Pro Gly Pro Pro Gln Ala Val Ala Pro Pro Ala Pro
    1085                1090                1095

Lys Pro Thr Gln Ala Gly Glu Gly Thr Leu Ser Glu Ala Leu Leu
    1100                1105                1110
```

```
Gln Leu Gln Phe Asp Asp Glu Asp Leu Gly Ala Leu Leu Gly Asn
    1115                1120                1125

Ser Thr Asp Pro Ala Val Phe Thr Asp Leu Ala Ser Val Asp Asn
    1130                1135                1140

Ser Glu Phe Gln Gln Leu Leu Asn Gln Gly Ile Pro Val Ala Pro
    1145                1150                1155

His Thr Thr Glu Pro Met Leu Met Glu Tyr Pro Glu Ala Ile Thr
    1160                1165                1170

Arg Leu Val Thr Gly Ala Gln Arg Pro Pro Asp Pro Ala Pro Ala
    1175                1180                1185

Pro Leu Gly Ala Pro Gly Leu Pro Asn Gly Leu Leu Ser Gly Asp
    1190                1195                1200

Glu Asp Phe Ser Ser Ile Ala Asp Met Asp Phe Ser Ala Leu Leu
    1205                1210                1215

Gly Ser Gly Ser Gly Ser Arg Asp Ser Arg Glu Gly Met Phe Leu
    1220                1225                1230

Pro Lys Pro Glu Ala Gly Ser Ala Ile Ser Asp Val Phe Glu Gly
    1235                1240                1245

Arg Glu Val Cys Gln Pro Lys Arg Ile Arg Pro Phe His Pro Pro
    1250                1255                1260

Gly Ser Pro Trp Ala Asn Arg Pro Leu Pro Ala Ser Leu Ala Pro
    1265                1270                1275

Thr Pro Thr Gly Pro Val His Glu Pro Val Gly Ser Leu Thr Pro
    1280                1285                1290

Ala Pro Val Pro Gln Pro Leu Asp Pro Ala Pro Ala Val Thr Pro
    1295                1300                1305

Glu Ala Ser His Leu Leu Glu Asp Pro Asp Glu Glu Thr Ser Gln
    1310                1315                1320

Ala Val Lys Ala Leu Arg Glu Met Ala Asp Thr Val Ile Pro Gln
    1325                1330                1335

Lys Glu Glu Ala Ala Ile Cys Gly Gln Met Asp Leu Ser His Pro
    1340                1345                1350

Pro Pro Arg Gly His Leu Asp Glu Leu Thr Thr Thr Leu Glu Ser
    1355                1360                1365

Met Thr Glu Asp Leu Asn Leu Asp Ser Pro Leu Thr Pro Glu Leu
    1370                1375                1380

Asn Glu Ile Leu Asp Thr Phe Leu Asn Asp Glu Cys Leu Leu His
    1385                1390                1395

Ala Met His Ile Ser Thr Gly Leu Ser Ile Phe Asp Thr Ser Leu
    1400                1405                1410

Phe

<210> SEQ ID NO 35
<211> LENGTH: 6
<212> TYPE: PRT
<213> ORGANISM: Artificial Sequence
<220> FEATURE:
<223> OTHER INFORMATION: Artificial Sequence created by rational design

<400> SEQUENCE: 35

Asn Asn Asn Arg Arg Thr
1               5

<210> SEQ ID NO 36
<211> LENGTH: 9
```

```
<212> TYPE: PRT
<213> ORGANISM: Artificial Sequence
<220> FEATURE:
<223> OTHER INFORMATION: Artificial Sequence created by rational design

<400> SEQUENCE: 36

Gly Gly Gly Gly Ser Gly Gly Gly Gly
1               5

<210> SEQ ID NO 37
<211> LENGTH: 7
<212> TYPE: PRT
<213> ORGANISM: Artificial Sequence
<220> FEATURE:
<223> OTHER INFORMATION: Artificial Sequence created by rational design

<400> SEQUENCE: 37

Lys Arg Arg Arg Arg His Arg
1               5
```